United States Patent
Kamlage et al.

(10) Patent No.: US 10,168,333 B2
(45) Date of Patent: Jan. 1, 2019

(54) MEANS AND METHODS FOR DIAGNOSING PANCREATIC CANCER IN A SUBJECT BASED ON A METABOLITE PANEL

(71) Applicant: METANOMICS HEALTH GMBH, Berlin (DE)

(72) Inventors: Beate Kamlage, Berlin (DE); Regina Reszka, Panektal (DE); Erik Peter, Potsdam (DE); Jürgen Kastler, Berlin (DE); Philipp Schatz, Berlin (DE); Holger Kalthoff, Kiel (DE); Bodo Schniewind, Kiel (DE); Julia Mayerle, Greifwald (DE); Markus Lerch, Greifwald (DE); Christian Pilarsky, Dresden (DE); Robert Grützmann, Dresden (DE)

(73) Assignee: METANOMICS HEALTH GMBH, Berlin (DE)

( * ) Notice: Subject to any disclaimer, the term of this patent is extended or adjusted under 35 U.S.C. 154(b) by 0 days.

(21) Appl. No.: 15/105,970

(22) PCT Filed: Dec. 19, 2014

(86) PCT No.: PCT/EP2014/078765
§ 371 (c)(1),
(2) Date: Jun. 17, 2016

(87) PCT Pub. No.: WO2015/091962
PCT Pub. Date: Jun. 25, 2015

(65) Prior Publication Data
US 2016/0313338 A1 Oct. 27, 2016

(30) Foreign Application Priority Data
Dec. 20, 2013 (EP) ..................................... 13198959

(51) Int. Cl.
*G01N 33/574* (2006.01)
*G01N 33/49* (2006.01)
*G01N 33/92* (2006.01)

(52) U.S. Cl.
CPC ....... *G01N 33/57438* (2013.01); *G01N 33/49* (2013.01); *G01N 33/92* (2013.01); *G01N 2400/00* (2013.01); *G01N 2405/00* (2013.01); *G01N 2405/04* (2013.01); *G01N 2405/08* (2013.01)

(58) Field of Classification Search
CPC ....... G01N 33/57434; G01N 33/57484; G01N 2800/7028
See application file for complete search history.

(56) References Cited

U.S. PATENT DOCUMENTS 4,540,884 A 9/1985 Stafford et al.
5,397,894 A 3/1995 Wells et al.
7,196,323 B2 3/2007 Walk et al.
2012/0202188 A1 8/2012 Pastural et al.
2015/0104816 A1 4/2015 Noda et al.

FOREIGN PATENT DOCUMENTS

| WO | WO-03/073464 A1 | 9/2003 | |
| WO | WO-2011/101330 A1 | 8/2011 | |
| WO | WO-2011/151252 A2 | 12/2011 | |
| WO | WO 2011163332 A2 * | 12/2011 | ....... G01N 33/57488 |
| WO | WO-2013/079594 A1 | 6/2013 | |
| WO | WO-2013/172105 A1 | 11/2013 | |

OTHER PUBLICATIONS

Matyash, Vitali et al. "Lipid extraction by methyl-tert-butyl ether for high-throughput lipidomics." J. Lip. Res. (2008) 49 1137-1146. (Year: 2008).*
Brand et al., Advances in counselling and surveillance of patients at risk for pancreatic cancer, Gut, 56(10):1460-9 (2007).
Christie, Rapid separation and quantification of lipid classes by high performance liquid chromatography and mass (light-scattering) detection, J. Lipid Res., 26(4):507-12 (1985).
Dewitt et al., Comparison of endoscopic ultrasound and computed tomography for the preoperative evaluation of pancreatic cancer: a systematic review, Clin. Gastroenterol. Hepatol., 4(6):717-25 (2006).
European Search Report, European Patent Application No. EP13198959, completed Apr. 7, 2014.
Everhart et al., Burden of digestive diseases in the United States Part III: Liver, biliary tract, and pancreas, Gastroenterology, 136(4):1134-44 (2009).
Fry et al., Molecular markers of pancreatic cancer: development and clinical relevance, Langenbecks Arch. Surg., 393(6):883-9 (2008).
Howes et al., Clinical and genetic characteristics of hereditary pancreatitis in Europe, Clin. Gastroenterol. Hepatol., 2(3):252-61 (2004).
Hruban et al., An illustrated consensus on the classification of pancreatic intraepithelial neoplasia and intraductal papillary mucinous neoplasms, Am.J. Surg. Pathol., 28(8):977-87 (2004).
International Preliminary Report on Patentability, International Application No. PCT/EP2014/078765, dated Jun. 21, 2016.
International Search Report and Written Opinion, International Application No. PCT/EP2014/078765, dated Mar. 18, 2015.
Liaw et al., Classification and regression by random Forest, R News, vol. 2/3:18-22 (Dec. 2002).
Lowenfels et al., Cigarette smoking as a risk factor for pancreatic cancer in patients with hereditary pancreatitis, JAMA, 286(2):169-70 (2001).

(Continued)

*Primary Examiner* — Christopher Adam Hixson
(74) *Attorney, Agent, or Firm* — Marshall, Gerstein & Borun LLP

(57) ABSTRACT

The present invention relates to the field of diagnostic methods. Specifically, the present invention contemplates a method for diagnosing pancreas cancer in a subject and, preferably for differentiating between pancreatic cancer and pancreatitis and a method for identifying whether a subject is in need for a therapy of pancreatic cancer. The invention also relates to tools for carrying out the aforementioned methods, such as diagnostic devices.

9 Claims, No Drawings

(56) References Cited

OTHER PUBLICATIONS

Lowenfels et al., Hereditary pancreatitis and the risk of pancreatic cancer. International Hereditary Pancreatitis Study Group, J. Natl. Cancer Inst., 89(6):442-6 (1997).

Lowenfels et al., Pancreatitis and the risk of pancreatic cancer. International Pancreatitis Study Group, N. Engl. J. Med., 328(20)1433-7 (1993).

Modrak et al., Ceramide regulates gemcitabine-induced senescence and apoptosis in human pancreatic cancer cell lines, Mol. Cancer Res., 7(6):890-6 (2009).

Mutch et al., Metabolite profiling identifies candidate markers reflecting the clinical adaptations associated with Roux-en-Y gastric bypass surgery, PLoS One, 4(11):e7905 (2009).

Nissen et al., Liquid chromatography-mass spectrometry General principles and instrumentation, J. Chromatography A, 703:37-57 (1995).

Pitson, Regulation of sphingosine kinase and sphingolipid signaling, Trends Biochem. Sci., 36(2):97-107 (2011).

Roessner et al., Technical advance: simultaneous analysis of metabolites in potato tuber by gas chromatography-mass spectrometry, Plant J., 23(1):131-42 (2000).

Schmidt et al., LC-MS/MS-analysis of sphingosine-1-phosphate and related compounds in plasma samples, Prostaglandins Other Lipid Mediat., 81(3-4):162-70 (2006).

Schrader et al., Amino acid malnutrition in patients with chronic pancreatitis and pancreatic carcinoma, Pancreas, 38(4):416-21 (2009).

Van Ravenzwaay et al., The use of metabolomics for the discovery of new biomarkers of effect, Toxicol. Lett., 172(1-2):21-8 (2007).

Zhou et al., Chapter 2: Measures of Diagnostic Accuracy, In: Zhou et al., *Statistical Methods in Diagnostic Medicine*, 2nd ed. (2011).

Zou et al., Regularization and variable selection via the elastic net, J.R. Statist. Soc. B, 67(Part 2):301-20 (2005).

Zweig et al., Receiver-operating characteristic (ROC) plots: a fundamental evaluation tool in clinical medicine, Clin. Chem., 39(4):561-77 (1993).

Notification of Reasons for Refusal for Japanese Application No. 2016-541297, dated Sep. 20, 2018.

* cited by examiner

MEANS AND METHODS FOR DIAGNOSING PANCREATIC CANCER IN A SUBJECT BASED ON A METABOLITE PANEL

This application is a National Stage application of International Application No. PCT/EP2014/078765, filed Dec. 19, 2014, which claims the benefit under 35 U.S.C. § 119 of European Patent Application No. 13198959.2, filed Dec. 20, 2013.

The present invention relates to the field of diagnostic methods. Specifically, the present invention contemplates a method for diagnosing pancreas cancer in a subject and, preferably for differentiating between pancreatic cancer and pancreatitis and a method for identifying whether a subject is in need for a therapy of pancreatic cancer. The invention also relates to tools for carrying out the aforementioned methods, such as diagnostic devices.

Pancreatic cancer has the worst prognosis of all solid tumors with 5-year survival rates of less than 5% but an increasing incidence (Everhart 2009, Gastroenterology 136: 1134-11449). There is a widely acknowledged demand for the establishment of innovative tools and technologies for point-of-care utilization of specific biomarkers and novel molecular imaging tools for early diagnosis, prognostic stratification and differential diagnosis of pancreatic cancer. Advances in these areas are pivotal to improve the prognosis of this malignancy, since timely surgical resection of early stage tumors is currently the only effective means of treatment of this dismal disease.

The mortality of this cancer type is the highest of any cancer type in Europe and the western world. People die soon after diagnosis due to the lack of means for early detection. Early symptoms are rare and uncharacteristic. Thus, pancreatic adenocarcinomas (PDACs) are commonly diagnosed in an advanced stage of the disease. To date, the best imaging technologies to detect PDAC are endoscopic ultrasound (EUS), spiral computer tomography (CT), magnetic resonance cholangiopancreatography (MRCP) or endoscopic retrograde cholangiopancreatography (ERCP) (Dewitt 2006, Gastroenterol Hepatol. (4):717-25). Unfortunately, the resolution of these technologies for detecting neoplastic lesions within the pancreas is in the range of 3-10 mm. Thus, they are not able to detect pancreatic neoplasia at a curable stage. The serum concentration of conventional tumor markers such as CA19-9 is increased in a subset of pancreatic cancer patients (Fry 2008, Langenbecks Arch Surg. (393): 883-90). However, so far all available markers lack sensitivity and tumor specificity. Thus, new approaches are urgently needed to increase the diagnostic sensitivity towards the detection of very small, early stage PDAC and its precursor lesions (PanINs and IPMNs) as well as prognostic subgroups of advanced tumors.

The association between chronic inflammation and the development of malignancies has been recognized for many years. For pancreatic cancer this association was only recently confirmed and a consensus conference agreed upon a new classification for pancreatic intraepithelial neoplasia as noninvasive precursor lesions (Hruban 2004, Am J Surg Path (28): 977-987). Chronic pancreatitis is defined as recurrent bouts of a sterile inflammatory disease characterized by often progressive and irreversible morphological changes, typically causing pain and permanent impairment of pancreatic function. With an incidence of 8.2, a prevalence of 27.4 per 100 000 population and a 0.04% to 5% frequency in unselected autopsy specimens chronic pancreatitis represents a frequent disorder of the gastrointestinal tract. Various etiologies are responsible for the development of chronic pancreatitis. An increased risk of patients suffering from of chronic pancreatitis to die from pancreatic cancer was shown in an international cooperative investigation conducted by AB Lowenfels and coworkers as a multicenter historical cohort study of 2015 patients with chronic pancreatitis recruited from clinical centres in 6 countries in 1993. This study found a cumulative risk of pancreatic cancer in patients with chronic pancreatitis of 1.8% after 10 years and of 4% after 20 years with a standardized incidence ratio of 14.4. For patients with a minimum of two years follow up the risk of pancreatic cancer was 16.5 fold higher than that of the general population (Lowenfels 1993, N Engl J Med (328): 1433-1437). The search for an association between chronic pancreatitis and pancreatic cancer intensified when in 1996 a single point mutation in the third exon of the cationic trypsinogen gene on chromosome 7 (7q35) was found to be associated with hereditary pancreatitis and multiple kindreds were subsequently identified and reported. Only very recently the EUROPAC study group presented their work on clinical and genetic characteristics in hereditary pancreatitis. In a multilevel proportional hazard model employing data obtained from the European Registry of Hereditary Pancreatitis this group presented 112 families in 14 countries (418 affected individuals) (Howes 2004, Clinical Gastroenterology and Hepatology (2): 252-261). The cumulative risk (95% CI) of pancreatic cancer was 44.0% (8.0%-80.0%) at 70 years from symptom onset with a standardized incidence ratio of 67% (50%-82%). A previous study had also shown an estimated lifetime risk of pancreatic cancer of 40% (Lowenfels 2001, JAMA 286: 169-170, Lowenfels 1997, J Natl Cancer Inst 89: 442-44656).

In pancreatic cancer imaging studies fail to detect early pancreatic malignancies in a curable stage, however in the background of chronic pancreatitis imaging studies such as EUS, CT or MRI drop sensitivity and specificity to a degree where tossing a coin is equally reliable. Thus, the detection of pancreatic malignancy in a high risk cohort would be highly desired.

There are a few reports of metabolic changes in patients suffering from pancreas-associated diseases. Schrader et al (Schrader 2009, Pancreas 38: 416-421) suggests that patients with pancreatic cancer and chronic pancreatitis show significant changes in serum aminoacid levels. It has been suggested that sphingolipids on the cell surface of cells takes actively part in cell signalling (Pitson 2011, Trend Biochem Sci 36:97-107). Ceramides are known to induce apoptosis in cancer cells. Low levels of sphingomyelin suggest less responsiveness to gemcitabine treatment (Modrak 2009, Mol Cancer Res 7:890-896). Further single metabolic biomarkers have been reported in WO 2011/151252 and WO 2013/079594.

In conclusion with a 5-year survival rate of 0.5-5%, pancreatic cancer carries the most dismal prognosis of all human tumors and represents the 4th leading cause in cancer-related deaths worldwide. It is thus a disease with a major socioeconomic impact. Accurate diagnosis including its differentiation from pancreatitis and timely surgical resection of early tumors currently offer the only realistic prospect for the improvement of patient prognosis.

The technical problem underlying the present invention can be seen as the provision of means and methods for complying with the aforementioned needs. The technical problem is solved by the embodiments characterized in the claims and herein below.

Thus, the present invention relates to a method for diagnosing pancreas cancer in a subject comprising the steps of:

(a) determining in a sample of a subject suspected to suffer from pancreas cancer the amounts of a group of biomarkers said group comprising at least the biomarkers of one of the combinations shown in Table 1a or comprising at least the biomarkers shown in any one of Table 17 to 26 and (b) comparing the said amounts of the biomarkers with references, whereby pancreas cancer is to be diagnosed.

The method as referred to in accordance with the present invention includes a method which essentially consists of the aforementioned steps or a method which includes further steps. However, it is to be understood that the method, in a preferred embodiment, is a method carried out ex vivo, i.e. not practised on the human or animal body. The method, preferably, can be assisted by automation.

The term "diagnosing" as used herein refers to assessing whether a subject suffers from the pancreatic cancer, or not. As will be understood by those skilled in the art, such an assessment, although preferred to be, may usually not be correct for 100% of the investigated subjects. The term, however, requires that a statistically significant portion of subjects can be correctly assessed and, thus, diagnosed. Whether a portion is statistically significant can be determined without further ado by the person skilled in the art using various well known statistic evaluation tools, e.g., determination of confidence intervals, p-value determination, Student's t-test, MannWhitney test, etc. Details are found in Dowdy and Wearden, Statistics for Research, John Wiley & Sons, New York 1983. Preferred confidence intervals are at least 50%, at least 60%, at least 70%, at least 80%, at least 90% or at least 95%. The p-values are, preferably, 0.2, 0.1, or 0.05.

The term includes individual diagnosis of pancreatic cancer or its symptoms as well as continuous monitoring of a patient. Monitoring, i.e. diagnosing the presence or absence of pancreatic cancer or the symptoms accompanying it at various time points, includes monitoring of patients known to suffer from pancreatic cancer as well as monitoring of subjects known to be at risk of developing pancreatic cancer. Furthermore, monitoring can also be used to determine whether a patient is treated successfully or whether at least symptoms of pancreatic cancer can be ameliorated over time by a certain therapy.

Moreover, the term also, preferably, comprises differentially diagnosing pancreatic cancer and, more preferably, differentiating between pancreatic cancer and pancreatitis. Pancreatitis as used herein refers to an inflammation of the pancreas. Usually, the cause of pancreatitis is an activation of the pancreatic enzymes, e.g., trypsin, in the pancreas rather than the small intestine. Pancreatitis may occur as an acute disease which occurs suddenly and lasts a few days or as a chronic disease which persists over many years. Preferably, pancreatitis referred to in accordance with the present invention is chronic pancreatitis. Typical symptoms of pancreatitis can be found in the aforementioned standard text books and encompass severe upper abdominal pain radiating to the back, nausea and vomiting. Differentiating between pancreatic cancer and pancreatitis is preferably achieved by applying the methods of the present invention to a sample of a subject known or suspected to suffer from pancreatitis and comparing the measured amounts of the biomarkers with references, whereby pancreatic cancer is diagnosed. In a further preferred embodiment, said diagnosis of pancreatic cancer leads to the differentiation whether the person known or suspected to suffer from pancreatitis additionally suffers from pancreatic cancer.

The term "pancreatic cancer" or "pancreas cancer" as used herein relates to neoplasms which are derived from pancreatic cells and, preferably, from the pancreatic epithelial cells. Thus, preferably, pancreatic cancer as used herein is pancreatic adenocarcinoma. The symptoms accompanying pancreatic cancer are well known from standard text books of medicine such as Stedmen or Pschyrembl and include severe abdominal pain, lower back pain, and in some cases jaundice.

The term "biomarker" as used herein refers to a molecular species which serves as an indicator for a disease or effect as referred to in this specification. Said molecular species can be a metabolite itself which is found in a sample of a subject. Moreover, the biomarker may also be a molecular species which is derived from said metabolite. In such a case, the actual metabolite will be chemically modified in the sample or during the determination process and, as a result of said modification, a chemically different molecular species, i.e. the analyte, will be the determined molecular species. It is to be understood that in such a case, the analyte represents the actual metabolite and has the same potential as an indicator for the respective medical condition.

Moreover, a biomarker according to the present invention is not necessarily corresponding to one molecular species. Rather, the biomarker may comprise stereoisomers or enantiomeres of a compound. Further, a biomarker can also represent the sum of isomers of a biological class of isomeric molecules. Said isomers shall exhibit identical analytical characteristics in some cases and are, therefore, not distinguishable by various analytical methods including those applied in the accompanying Examples described below. However, the isomers will share at least identical sum formula parameters and, thus, in the case of, e.g., lipids an identical chain length and identical numbers of double bonds in the fatty acid and/or sphingo base moieties.

A metabolite as used herein refers to at least one molecule of a specific metabolite up to a plurality of molecules of the said specific metabolite. It is to be understood further that a group of metabolites means a plurality of chemically different molecules wherein for each metabolite at least one molecule up to a plurality of molecules may be present. A metabolite in accordance with the present invention encompasses all classes of organic or inorganic chemical compounds including those being comprised by biological material such as organisms. Preferably, the metabolite in accordance with the present invention is a small molecule compound. More preferably, in case a plurality of metabolites is envisaged, said plurality of metabolites representing a metabolome, i.e. the collection of metabolites being comprised by an organism, an organ, a tissue, a body fluid or a cell at a specific time and under specific conditions.

In Table 1a, core biomarker panels are shown which can be advantageously applied in the method of the present invention (the so-called "core panels"). In a preferred embodiment, lysophosphatidylethanolamine (C22:5) is determined instead of or in addition to lysophosphatidylethanolamine (C18:2), and the direction of change of lysophosphatidylethanolamine (C22:5) in pancreatic cancer relative to pancreatitis is down. In a further preferred embodiment, sphingolipids, including sphingomyelins and ceramides, comprise a sphingobase comprising two hydroxyl-moieties (i.e., comprise a d-sphingobase), of which both or, preferably, one may be esterified, e.g., preferably, to a phosphoric acid moiety or a chemical group comprising the same. In a preferred embodiment, the ceramide is a ceramide of Table 1b and the sphingomyelin is a sphingomyelin of Table 1 b. In a further preferred embodiment, the phosphorylated sphingobase is sphingosine-1-phosphate (d16:1), sphingosine-1-phosphate (d17:1), sphingadienine-1-phosphate (dl 8:2), or a phosphorylated sphingobase of Table 1b, and the direction of change in pancreatic cancer relative to pancreatitis is down, respectively. Preferred sphingomyelins, ceramides and/or phosphorylated sphingobases to be used are listed in Table 1b.

Preferred groups (panels) of biomarkers which comprise the aforementioned biomarkers of the core panels are shown in any one of Tables 2 to 15. These groups of biomarkers may be preferably determined as biomarker groups in accordance with the present invention.

Moreover, in Tables 17 to 26 further biomarker groups are shown which may also be preferably determined in accordance with the present invention and which allow also for an efficient diagnosis.

In addition to the specific biomarkers recited in the specification, other biomarkers may be, preferably, determined as well in the methods of the present invention. Such biomarkers may be metabolite biomarkers and preferably those shown in Table 16 or may include peptide or polypeptide biomarkers or glycosides such as the CA 19-9 antigen. Preferably, the CA 19-9 antigen may be determined in accordance with the present invention numerically, i.e. by taking into account its absolute amounts, or categorically, i.e. by determining whether the amount found in a patient is below or above a certain threshold level, preferably, a threshold as specified in the Examples below. How CA 19-9 can be determined numerically or categorically is, preferably, described in the accompanying Examples, below.

The term "sample" as used herein refers to samples from body fluids, preferably, blood, plasma, serum, saliva or urine, or samples derived, e.g., by biopsy, from cells, tissues or organs, in particular from the pancreas. More preferably, the sample is a blood, plasma or serum sample, most preferably, a plasma sample. Biological samples can be derived from a subject as specified elsewhere herein. Techniques for obtaining the aforementioned different types of biological samples are well known in the art. For example, blood samples may be obtained by blood taking while tissue or organ samples are to be obtained, e.g., by biopsy.

The aforementioned samples are, preferably, pre-treated before they are used for the method of the present invention. As described in more detail below, said pre-treatment may include treatments required to release or separate the compounds or to remove excessive material or waste. Suitable techniques comprise centrifugation, extraction, fractioning, ultrafiltration, protein precipitation followed by filtration and purification and/or enrichment of compounds. Moreover, other pre-treatments are carried out in order to provide the compounds in a form or concentration suitable for compound analysis. For example, if gas-chromatography coupled mass spectrometry is used in the method of the present invention, it will be required to derivatize the compounds prior to the said gas chromatography. Suitable and necessary pre-treatments depend on the means used for carrying out the method of the invention and are well known to the person skilled in the art. Pre-treated samples as described before are also comprised by the term "sample" as used in accordance with the present invention.

The sample may also, preferably, be pre-treated by lipid fractionation. Lipid fractionation as used in this context refers to a process as, preferably, described in the accompanying Examples below. In particular, lipid fractionation can be achieved by extracting the total lipids from serum or, preferably, plasma by liquid/liquid extraction using chloroform/methanol. The lipid extracts obtained thereby are subsequently fractionated by normal phase liquid chromatography (NPLC) into eleven different lipid groups according to Christie (Journal of Lipid Research (26), 1985, 507-512). The fractions were analyzed by LC-MS/MS using electrospray ionization (ESI) and atmospheric pressure chemical ionization (APCI) with detection of specific multiple reaction monitoring (MRM) transitions for cholesterol esters (CE), free sterols (FS), sphingoymelins (SM), and ceramides (CER) respectively. Sphingosines and sphingosine-1-phosphates (SP) were analyzed by LC-MS/MS using electrospray ionization (ESI) with detection of specific multiple reaction monitoring (MRM) transitions as described by Schmidt H et. al., Prostaglandins & other Lipid Mediators 81(2006), 162-170. The fractions are further analyzed by GC-MS after derivatization with TMSH (Trimethyl sulfonium hydroxide), yielding the fatty acid methyl esters (FAME) corresponding to the acyl moieties of the class-separated lipids. The concentrations of FAME from C14 to C24 are determined in each fraction. Preferably, lipid fractionation is used for determining ceramides and/or sphingomyelins as biomarkers in accordance with the present invention.

The term "subject" as used herein relates to animals and, preferably, to mammals. More preferably, the subject is a primate and, most preferably, a human. The subject, preferably, is suspected to suffer from pancreatic cancer, i.e. it may already show some or all of the symptoms associated with the disease. Moreover, the subject may also preferably suffer from or shall be suspected to suffer from pancreatitis and, preferably, shows an increase in CA 19-9 relative to healthy controls. Preferably, the subject, however, is besides the aforementioned diseases and disorders apparently healthy. The said subject, preferably, is at increased risk of developing pancreatic cancer (Brand R E et al, Gut. 2007; 56:1460-9). More preferably, such a subject being at increased risk has one or more relatives suffering from pancreatic cancer, has a defined genetic predisposition for developing pancreatic cancer, including but not exclusive to Peutz-Jeghers Syndrome, has one or more relatives suffering from pancreatitis, and/or has a defined genetic predisposition for developing pancreatitis. In another preferred embodiment, the "subject" as used herein is a Lewis blood type negative human.

The term "determining the amount" as used herein refers to determining at least one characteristic feature of a biomarker to be determined by the method of the present invention in the sample. Characteristic features in accordance with the present invention are features which characterize the physical and/or chemical properties including biochemical properties of a biomarker. Such properties include, e.g., molecular weight, viscosity, density, electrical charge, spin, optical activity, colour, fluorescence, chemoluminescence, elementary composition, chemical structure, capability to react with other compounds, capability to elicit a response in a biological read out system (e.g., induction of a reporter gene) and the like. Values for said properties may serve as characteristic features and can be determined by techniques well known in the art. Moreover, the characteristic feature may be any feature which is derived from the values of the physical and/or chemical properties of a biomarker by standard operations, e.g., mathematical calculations such as multiplication, division or logarithmic calculus. Most preferably, the at least one characteristic feature allows the determination and/or chemical identification of the said biomarker and its amount. Accordingly, the characteristic value, preferably, also comprises information relating to the abundance of the biomarker from which the characteristic value is derived. For example, a characteristic value of a biomarker may be a peak in a mass spectrum. Such a peak contains characteristic information of the biomarker, i.e. the m/z information, as well as an intensity value being related to the abundance of the said biomarker (i.e. its amount) in the sample.

As discussed before, each biomarker comprised by a sample may be, preferably, determined in accordance with the present invention quantitatively or semi-quantitatively. For quantitative determination, either the absolute or precise amount of the biomarker will be determined or the relative amount of the biomarker will be determined based on the value determined for the characteristic feature(s) referred to herein above. The relative amount may be determined in a case were the precise amount of a biomarker can or shall not be determined. In said case, it can be determined whether the amount in which the biomarker is present is enlarged or diminished with respect to a second sample comprising said biomarker in a second amount. In a preferred embodiment said second sample comprising said biomarker shall be a calculated reference as specified elsewhere herein. Quantitatively analysing a biomarker, thus, also includes what is sometimes referred to as semi-quantitative analysis of a biomarker.

Moreover, determining as used in the method of the present invention, preferably, includes using a compound separation step prior to the analysis step referred to before. Preferably, said compound separation step yields a time resolved separation of the metabolites comprised by the sample. Suitable techniques for separation to be used preferably in accordance with the present invention, therefore, include all chromatographic separation techniques such as liquid chromatography (LC), high performance liquid chromatography (HPLC), gas chromatography (GC), thin layer chromatography, size exclusion or affinity chromatography. These techniques are well known in the art and can be applied by the person skilled in the art without further ado. Most preferably, LC and/or GC are chromatographic techniques to be envisaged by the method of the present invention. Suitable devices for such determination of biomarkers are well known in the art. Preferably, mass spectrometry is used in particular gas chromatography mass spectrometry (GC-MS), liquid chromatography mass spectrometry (LC-MS), direct infusion mass spectrometry or Fourier transform ion-cyclotrone-resonance mass spectrometry (FT-ICR-MS), capillary electrophoresis mass spectrometry (CE-MS), high-performance liquid chromatography coupled mass spectrometry (HPLC-MS), quadrupole mass spectrometry, any sequentially coupled mass spectrometry, such as MS-MS or MS-MS-MS, inductively coupled plasma mass spectrometry (ICP-MS), pyrolysis mass spectrometry (Py-MS), ion mobility mass spectrometry or time of flight mass spectrometry (TOF). Most preferably, LC-MS and/or GC-MS are used as described in detail below. Said techniques are disclosed in, e.g., Nissen 1995, Journal of Chromatography A, 703: 37-57, U.S. Pat. No. 4,540,884 or U.S. Pat. No. 5,397,894, the disclosure content of which is hereby incorporated by reference. As an alternative or in addition to mass spectrometry techniques, the following techniques may be used for compound determination: nuclear magnetic resonance (NMR), magnetic resonance imaging (MRI), Fourier transform infrared analysis (FTIR), ultraviolet (UV) spectroscopy, refraction index (RI), fluorescent detection, radiochemical detection, electrochemical detection, light scattering (LS), dispersive Raman spectroscopy or flame ionisation detection (FID). These techniques are well known to the person skilled in the art and can be applied without further ado. The method of the present invention shall be, preferably, assisted by automation. For example, sample processing or pre-treatment can be automated by robotics. Data processing and comparison is, preferably, assisted by suitable computer programs and databases. Automation as described herein before allows using the method of the present invention in high-throughput approaches.

Moreover, the at least one biomarker can also be determined by a specific chemical or biological assay. Said assay shall comprise means which allow to specifically detect the at least one biomarker in the sample. Preferably, said means are capable of specifically recognizing the chemical structure of the biomarker or are capable of specifically identifying the biomarker based on its capability to react with other compounds or its capability to elicit a response in a biological read out system (e.g., induction of a reporter gene). Means which are capable of specifically recognizing the chemical structure of a biomarker are, preferably, antibodies or other proteins which specifically interact with chemical structures, such as receptors or enzymes, or aptamers. Specific antibodies, for instance, may be obtained using the biomarker as antigen by methods well known in the art. Antibodies as referred to herein include both polyclonal and monoclonal antibodies, as well as fragments thereof, such as Fv, Fab and F(ab)$_2$ fragments that are capable of binding the antigen or hapten. The present invention also includes humanized hybrid antibodies wherein amino acid sequences of a non-human donor antibody exhibiting a desired antigen-specificity are combined with sequences of a human acceptor antibody. Moreover, encompassed are single chain antibodies. The donor sequences will usually include at least the antigen-binding amino acid residues of the donor but may comprise other structurally and/or functionally relevant amino acid residues of the donor antibody as well. Such hybrids can be prepared by several methods well known in the art. Suitable proteins which are capable of specifically recognizing the biomarker are, preferably, enzymes which are involved in the metabolic conversion of the said biomarker. Said enzymes may either use the biomarker as a substrate or may convert a substrate into the biomarker. Moreover, said antibodies may be used as a basis to generate oligopeptides which specifically recognize the biomarker. These oligopeptides shall, for example, comprise the enzyme's binding domains or pockets for the said biomarker. Suitable antibody and/or enzyme based assays may be RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA) or solid phase immune tests. Moreover, the biomarker may also be determined based on its capability to react with other compounds, i.e. by a specific chemical reaction. Further, the biomarker may be determined in a sample due to its capability to elicit a response in a biological read out system. The biological response shall be detected as read out indicating the presence and/or the amount of the biomarker comprised by the sample. The biological response may be, e.g., the induction of gene expression or a phenotypic response of a cell or an organism. In a preferred embodiment the determination of the least one biomarker is a quantitative process, e.g., allowing also the determination of the amount of the at least one biomarker in the sample As described above, said determining of the at least one biomarker can, preferably, comprise mass spectrometry (MS). Mass spectrometry as used herein encompasses all techniques which allow for the determination of the molecular weight (i.e. the mass) or a mass variable corresponding to a compound, i.e. a biomarker, to be determined in accordance with the present invention. Preferably, mass spectrometry as used herein relates to GC-MS, LC-MS, direct infusion mass spectrometry, FT-ICR-MS, CE-MS, HPLC-MS, quadrupole mass spectrometry, any sequentially coupled mass spectrometry such as MS-MS or MS-MS-MS, ICP-MS, Py-MS, TOF or any combined approaches using the aforementioned techniques. How to apply these techniques is well known to the person skilled in the art. Moreover, suitable devices are commercially available. More preferably, mass spectrometry as used herein relates to LC-MS and/or GC-MS, i.e. to mass spectrometry being operatively linked to a prior chromatographic separation step. More preferably, mass spectrometry as used herein encompasses quadrupole MS. Most preferably, said quadrupole MS is carried out as follows: a) selection of a mass/charge quotient (m/z) of an ion created by ionisation in a first analytical quadrupole of the mass spectrometer, b) fragmentation of the ion selected in step a) by applying an acceleration voltage in an additional subsequent quadrupole which is filled with a collision gas and acts as a collision chamber, c) selection of a mass/charge quotient of an ion created by the fragmentation process in step b) in an additional subsequent quadrupole, whereby steps a) to c) of the method are carried out at least once and analysis of the mass/charge quotient of all the ions present in the mixture of substances as a result of the ionisation process, whereby the quadrupole is filled with collision gas but no acceleration voltage is applied during the analysis. Details on said most preferred mass spectrometry to be used in accordance with the present invention can be found in WO 03/073464.

More preferably, said mass spectrometry is liquid chromatography (LC) MS and/or gas chromatography (GC) MS. Liquid chromatography as used herein refers to all techniques which allow for separation of compounds (i.e. metabolites) in liquid or supercritical phase. Liquid chromatography is characterized in that compounds in a mobile phase are passed through the stationary phase. When compounds pass through the stationary phase at different rates they become separated in time since each individual compound has its specific retention time (i.e. the time which is required by the compound to pass through the system). Liquid chromatography as used herein also includes HPLC. Devices for liquid chromatography are commercially available, e.g. from Agilent Technologies, USA. Gas chromatography as applied in accordance with the present invention, in principle, operates comparable to liquid chromatography. However, rather than having the compounds (i.e. metabolites) in a liquid mobile phase which is passed through the stationary phase, the compounds will be present in a gaseous volume. The compounds pass the column which may contain solid support materials as stationary phase or the walls of which may serve as or are coated with the stationary phase. Again, each compound has a specific time which is required for passing through the column. Moreover, in the case of gas chromatography it is preferably envisaged that the compounds are derivatised prior to gas chromatography. Suitable techniques for derivatisation are well known in the art. Preferably, derivatisation in accordance with the present invention relates to methoxymation and trimethylsilylation of, preferably, polar compounds and transmethylation, methoxymation and trimethylsilylation of, preferably, non-polar (i.e. lipophilic) compounds.

The term "reference" refers to values of characteristic features of each of the biomarkers which can be correlated to a medical condition, i.e. the presence or absence of the disease, diseases status or an effect referred to herein. Preferably, a reference is a threshold value (e.g., an amount or ratio of amounts) for a biomarker whereby values found in a sample to be investigated which are higher than or essentially identical to the threshold are indicative for the presence of a medical condition while those being lower are indicative for the absence of the medical condition. It will be understood that also preferably, a reference may be a threshold value for a biomarker whereby values found in a sample to be investigated which are lower or identical than the threshold are indicative for the presence of a medical condition while those being higher are indicative for the absence of the medical condition.

In accordance with the aforementioned method of the present invention, a reference is, preferably, a reference obtained from a sample from a subject or group of subjects known to suffer from pancreatic cancer. In such a case, a value for the at least one biomarker found in the test sample being essentially identical is indicative for the presence of the disease.

Moreover, the reference, also preferably, could be from a subject or group of subjects known not to suffer from pancreatic cancer, preferably, an apparently healthy subject or a group thereof or a subject which is known to suffer from pancreatitis or a group thereof. In such a case, a value for the at least one biomarker found in the test sample being altered with respect to the reference is indicative for the presence of the disease. The same applies mutatis mutandis for a calculated reference being, most preferably, the average or median for the relative value or the value for a degree of change of the at least one biomarker in a population of individuals (comprising the subject to be investigated). The relative values or degrees of changes of the at least one biomarker of said individuals of the population can be determined as specified elsewhere herein. How to calculate a suitable reference value, preferably, the average or median, is well known in the art. The population of subjects referred to before shall comprise a plurality of subjects, preferably, at least 5, 10, 50, 100, 1,000 or 10,000 subjects. It is to be understood that the subject to be diagnosed by the method of the present invention and the subjects of the said plurality of subjects are of the same species.

The value for a biomarker of the test sample and the reference value is essentially identical, if the values for the characteristic features and, in the case of quantitative determination, the intensity values are essentially identical. Essentially identical means that the difference between two values is, preferably, not significant and shall be characterized in that the values for the intensity are within at least the interval between $1^{st}$ and $99^{th}$ percentile, $5^{th}$ and $95^{th}$ percentile, $10^{th}$ and $90^{th}$ percentile, $20^{th}$ and $80^{th}$ percentile, $30^{th}$ and $70^{th}$ percentile, $40^{th}$ and $60^{th}$ percentile of the reference value, preferably, the $50^{th}$, $60^{th}$, $70^{th}$, $80^{th}$, $90^{th}$ or $95^{th}$ percentile of the reference value. Statistical test for determining whether two amounts are essentially identical are well known in the art and are also described elsewhere herein.

An observed difference for two values, on the other hand, shall be statistically significant. A difference in the relative or absolute value is, preferably, significant outside of the interval between $45^{th}$ and $55^{th}$ percentile, $40^{th}$ and $60^{th}$ percentile, $30^{th}$ and $70^{th}$ percentile, $20^{th}$ and $80^{th}$ percentile, $10^{th}$ and $90^{th}$ percentile, $5^{th}$ and $95^{th}$ percentile, $1^{st}$ and $99^{th}$ percentile of the reference value. Preferred relative changes of the medians or degrees of changes are described in the accompanying Tables as well as in the Examples. In the Tables below, a preferred relative change for the biomarkers is indicated as "up" for an increase and "down" for a decrease. The degree of the change is expressed as area under curve value (AUC) in the tables, below. The preferred references for the aforementioned relative changes or degrees of changes are indicated in the Tables below as well. It will be understood that these changes are, preferably, observed in comparison to the references indicated in the respective Tables, below.

More preferably, a "reference" for a biomarker will be obtained by determining the values for the at least one characteristic feature for the said biomarker of the group of biomarkers in a group of reference subjects, i.e. a group of subjects known to suffer from the disease or condition, a group of subjects known not to suffer from said disease or condition, a population comprising the subject to be investigated or a group of tissue biopsy samples of disease afflicted tissue or apparently healthy tissue and calculating the reference by appropriate statistic measures including those referred to elsewhere herein, such as median, average, quantiles, PLS-DA, logistic regression methods, ANOVA, random forest classification or others that give a threshold value. The threshold value should take the desired clinical settings of sensitivity and specificity of the diagnostic and prognostic test into consideration. Threshold amounts to be used as references may be, preferably, determined by applying receiver-operating characteristics (ROC) (see especially Zweig 1993, Clin. Chem. 39:561-577). The ROC graph is a plot of all of the sensitivity/specificity pairs resulting from continuously varying the decision threshold over the entire range of data observed. The clinical performance of a diagnostic method depends on its accuracy, i.e. its ability to correctly allocate subjects to a certain prognosis or diagnosis. The ROC plot indicates the overlap between the two distributions by plotting the sensitivity versus 1-specificity for the complete range of thresholds suitable for making a distinction. On the y-axis is sensitivity, or the true-positive fraction, which is defined as the ratio of number of true-positive test results to the product of number of true-positive and number of false-negative test results. This has also been referred to as positivity in the presence of a disease or condition. It is calculated solely from the affected subgroup. On the x-axis is the false-positive fraction, or 1-specificity, which is defined as the ratio of number of false-positive results to the product of number of true-negative and number of false-positive results. It is an index of specificity and is calculated entirely from the unaffected subgroup. Because the true- and false-positive fractions are calculated entirely separately, by using the test results from two different subgroups, the ROC plot is independent of the prevalence of the event in the cohort. Each point on the ROC plot represents a sensitivity/-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. If the ROC plot falls completely below the 45° diagonal, this is easily remedied by reversing the criterion for "positivity" from "greater than" to "less than" or vice versa. Qualitatively, the closer the plot is to the upper left corner, the higher the overall accuracy of the test. Dependent on a desired confidence interval, a threshold can be derived from the ROC curve allowing for the diagnosis or prediction for a given event with a proper balance of sensitivity and specificity, respectively. Accordingly, the reference to be used for the aforementioned method of the present invention, i.e. a threshold which allows to discriminate between subjects being at increased risk for mortality or those which have a normal risk among a cohort of subjects suffering from acute inflammation can be generated, preferably, by establishing a ROC for said cohort as described above and deriving a threshold amount therefrom. Dependent on a desired sensitivity and specificity for a diagnostic method, the ROC plot allows deriving suitable thresholds.

Preferably, the reference, i.e. values for at least one characteristic feature of the biomarker or ratios thereof, will be stored in a suitable data storage medium such as a database and are, thus, also available for future assessments.

The term "comparing" refers to determining whether the determined value of a biomarker is essentially identical to a reference or differs there from. Preferably, a value for a biomarker is deemed to differ from a reference if the observed difference is statistically significant which can be determined by statistical techniques referred to elsewhere in this description. If the difference is not statistically significant, the biomarker value and the reference are essentially identical.

Based on the comparison referred to above, a subject can be assessed to suffer from the disease, or not.

The comparison is, preferably, assisted by automation. For example, a suitable computer program comprising algorithms for the comparison of two different data sets (e.g., data sets comprising the values of the characteristic feature(s)) may be used. Such computer programs and algorithms are well known in the art. Notwithstanding the above, a comparison can also be carried out manually.

In a preferred embodiment, the amounts of a group of biomarkers as referred to herein of the methods of the present invention shall be compared to a reference or references; thus, the presence or absence of a disease as referred to herein is diagnosed by individual comparison of each biomarker to a corresponding reference. In another preferred embodiment, it is also envisaged to calculate a score (in particular a single score) based on the amounts of several, preferably all biomarkers determined in the method of the present invention, and to compare this score to a reference score calculated from corresponding references, and wherein, preferably, the calculated score combines information on the amounts of the biomarkers. Preferably, the score can be regarded as a classifier parameter for diagnosing pancreatic cancer. The reference score is preferably a value, in particular a cut-off value which allows for differentiating between the presence of disease and the absence of disease in the subject to be tested. Preferably, the reference is a single value, such that, preferably, the person interpreting the data does not have to interpret the information on the amounts of the biomarkers for each biomarker individually.

In light of the above, the method of the invention more typically, is a method for diagnosing pancreas cancer or for distinguishing between pancreatic cancer and pancreatitis in a subject comprising the steps of:

(a) selecting a subject which is suspected to suffer from pancreatic cancer;
(b) obtaining a test sample from said subject;
(c) pre-treating said test sample for analysis of the biomarkers comprised therein;
(d) determining the amounts of a group of biomarkers said group comprising at least the biomarkers of one of the combinations shown in Table 1a or comprising at least the biomarkers shown in any one of Table 17 to 26, preferably, by contacting the sample with detection agents, such as antibodies or aptameres, which specifically bind to the biomarkers of the group of biomarkers and which upon binding can be detected such that the amounts of the biomarker are determined;

(e) comparing the said amounts of the biomarkers with references for each of the biomarkers; and (f) based on the comparison of step (e), diagnose the presence or absence of pancreatic cancer or distinguish between pancreatic cancer and pancreatitis.

A suitable detection agent may be, preferably, an antibody which specifically binds to the biomarker in a sample of a subject to be investigated by the method of the invention. Another detection agent that can be applied, preferably, may be an aptamere which specifically binds to the biomarker in the sample. In yet a preferred embodiment, the sample is removed from the complex formed between the detection agent and the at least one biomarker prior to the measurement of the amount of formed complex. Accordingly, in a preferred embodiment, the detection agent may be immobilized on a solid support. In yet a preferred embodiment, the sample can be removed from the formed complex on the solid support by applying a washing solution. The formed complex shall be proportional to the amount of the at least one biomarker present in the sample. It will be understood that the specificity and/or sensitivity of the detection agent to be applied defines the degree of proportion of at least one biomarker comprised in the sample which is capable of being specifically bound. Further details on how the determination can be carried out are also found elsewhere herein. The amount of formed complex shall be transformed into an amount of at least one biomarker reflecting the amount indeed present in the sample. Such an amount, preferably, may be essentially the amount present in the sample or may be, preferably, an amount which is a certain proportion thereof due to the relationship between the formed complex and the amount present in the original sample.

In yet a preferred embodiment of the aforementioned method, step d) may be carried out by an analyzing unit, in an aspect, an analyzing unit as defined elsewhere herein.

In a preferred embodiment of the method of the invention, the amount determined in step d) is compared to a reference. Preferably, the reference is a reference as defined elsewhere herein. In yet another preferred embodiment, the reference takes into account the proportional relationship between the measured amount of complex and the amount present in the original sample. Thus, the references applied in a preferred embodiment of the method of the invention are artificial references which are adopted to reflect the limitations of the detection agent that has been used. In another preferred embodiment, said relationship can be also taken into account when carrying out the comparison, e.g., by including a normalization and/or correction calculation step for the determined amount prior to actually comparing the value of the determined amount and the reference. Again, the normalization and/or correction calculation step for the determined amount adopts the comparison step such that the limitations of the detection agent that has been used are reflected properly. Preferably, the comparison is carried out automatically, e.g., assisted by a computer system or the like.

The aid for diagnosing is established based on the comparison carried out in step b) by allocating the subject (i) either into a group of subjects suffering from pancreatic cancer with certain likelihood or a group not suffering therefrom, or (ii) a group of subjects suffering pancreatic cancer or a group suffering from pancreatitis. As discussed elsewhere herein already, the allocation of the investigated subject must not be correct in 100% of the investigated cases. Moreover, the groups of subjects into which the investigated subject is allocated are artificial groups in that they are established based on statistical considerations, i.e. a certain preselected degree of likelihood based on which the method of the invention shall operate. Thus, the method may establish an aid of diagnosis which may, in an aspect, require further strengthening of the diagnosis by other techniques. Preferably, the aid for diagnosing is established automatically, e.g., assisted by a computer system or the like.

In a preferred embodiment of the method of the invention, the determination of the at least one biomarker is achieved by mass spectroscopy techniques (preferably GCMS and/or LCMS), NMR or others referred to herein above. In such cases, preferably, the sample to be analyzed is pretreated. Said pretreatment, preferably, includes obtaining of the at least one biomarker from sample material, e.g., plasma or serum may be obtained from whole blood or the at least one biomarker may even be specifically extracted from sample material. Moreover, for GCMS, further sample pretreatment such as derivatization of the at least one biomarker is, preferably, required. Furthermore, pretreatment also, preferably, includes diluting sample material and adjusting or normalizing the concentration of the components comprised therein. To this end, preferably, normalization standards may be added to the sample in predefined amounts which allow for making a comparison of the amount of the at least one biomarker and the reference and/or between different samples to be analyzed.

The method of the present invention, in a preferred embodiment, furthermore further comprises a step of recommending and/or managing the subject according to the result of the aid of diagnosis established in step c). Such a recommendation may, in an aspect, be an adaptation of life style, nutrition and the like aiming to improve the life circumstances, the application of therapeutic measures as set forth elsewhere herein in detail, and/or a regular disease monitoring.

In another preferred embodiment of the aforementioned method, steps e) and/or f) are carried out by an evaluation unit as set forth elsewhere herein.

Advantageously, it has been found in the study underlying the present invention that the amounts of the specific biomarkers comprised in the group of biomarkers referred to herein above are indicators for pancreatic cancer and, in particular, allow for differentiating pancreatic cancer from pancreatitis. This is particularly helpful for an efficient diagnosis of the disease as well as for improving of the pre-clinical and clinical management of pancreatic cancer as well as an efficient monitoring of patients. Moreover, the findings underlying the present invention will also facilitate the development of efficient drug-based therapies or other interventions against pancreatic cancer as set forth in detail below.

The definitions and explanations of the terms made above apply mutatis mutandis for the following embodiments of the present invention except specified otherwise herein below.

In a preferred embodiment of the method of the invention, said subject is suspected to suffer from pancreas cancer or from chronic pancreatitis.

In another preferred embodiment of the method of the present invention, said references are derived from a sample of a subject or a group of subjects known to suffer from pancreatic cancer.

In yet another embodiment of the method of the present invention, said references are derived from a sample of a subject or a group of subjects known not to suffer from pancreatic cancer.

In a further embodiment of the method of the present invention, said group of biomarkers comprises at least one further biomarker selected from Table 16.

In another preferred embodiment of the method of the present invention, said group of biomarkers is the group shown in any one of Tables 2 to 15.

Moreover, in a preferred embodiment of the method of the invention, the said group of biomarkers further comprises CA19-9.

Yet, in a preferred embodiment of the method of the present invention, said diagnosing comprises differentiating between pancreatic cancer and pancreatitis.

The present invention also relates to a method for identifying whether a subject is in need of a pancreas cancer therapy comprising the steps of the aforementioned method of the invention and the further step of identifying a subject in need of a pancreas cancer therapy if said subject is to be diagnosed to suffer from pancreas cancer.

The phrase "in need for a therapy of pancreatic cancer" as used herein means that the disease in the subject is in a status where therapeutic intervention is necessary or beneficial in order to ameliorate or treat pancreatic cancer or the symptoms associated therewith. Accordingly, the findings of the studies underlying the present invention do not only allow diagnosing pancreatic cancer in a subject but also allow for identifying subjects which should be treated by a pancreatic cancer therapy or whose pancreatic cancer therapy needs adjustment. Once the subject has been identified, the method may further include a step of making recommendations for a therapy of pancreatic cancer.

Moreover, in a preferred embodiment of the aforementioned method of the invention, said method further comprises the step of recommending a therapeutic or patient health management measure for the subject based on whether the subject is diagnosed to suffer from pancreatic cancer or from pancreatitis.

The term "recommending" as used herein refers to making suggestions for therapeutic measures and/or patient health management measures which are specifically applicable to the patient. Recommending does, preferably, not encompass the actual application of the recommended therapeutic or patient health management measure.

The term "therapeutic or patient health management measure" as used herein refers to therapeutic measures aiming to cure or ameliorate pancreatic cancer or pancreatitis or aiming at preventing progression of the said diseases as well as patient health management measures such as monitoring including selection of monitoring measures and monitoring frequency and hospitalization. Preferably, the said therapeutic or patient health management measure is selected from the group consisting of: surgery, administration of anti-cancer drugs, patient monitoring, active surveillance, and hospitalization. Suitable cancer therapies include surgery, low- and high-dose irradiation, and systemic chemotherapy, e.g., cytostatic drugs, alone, or in combination with other drugs. Preferred surgery-based therapies include resection of the pancreas or parts thereof, such as pancreaticoduodenectomy, tail pancreatectomy, total or partial pancreatoctomy, palliative bridging procedures. Drug-based therapies, preferably, include the administration of one or more drugs with anti-tumour properties including but not exclusive to platinum derivatives, e.g., oxaliplatin, fluoropyrimidines, pyrimidine analogues, Gemcitabine, antimetabolites, alkylating agents, anthracyclines, plant alkaloids, topoisomerase inhibitors, targeted antibodies and tryosine kinase inhibitors. Particular preferred drugs include but are not limited to gemcitabine alone or in combination with erlotinib and/or oxaliplatin. It will be understood that the method can also be applied to determine whether a subject will benefit from or is in need of a therapy against the aforementioned diseases. Such a method can be applied in therapeutic approaches like "active surveillance". In this approach, a subject suffering from, e.g., less advanced pancreatitis is subjected to a method for diagnosing pancreatic cancer as set forth above on a short regular basis in order to detect the early onset of progression. Only after the progression becomes detectable, the subject will be treated by a suitable therapy, such as surgery or irradiation. Thus, "active surveillance" prevents the harmful side effects of a therapy in subjects which are not in an immediate need for a therapy. By avoiding the therapy at this stage, it will be understood that the harmful side effects of the therapy can be avoided as well. In a more preferred embodiment of the method of the present invention, said method also comprises the step of applying the said therapeutic or patient health management measure as identified by the aforementioned method to the subject.

The present invention contemplates a device for diagnosing pancreas cancer in a sample of a subject comprising:

a) an analyzing unit for the said sample of the subject comprising a detector the amounts of a group of biomarkers said group comprising at least the biomarkers of one of the combinations shown in Table 1a or comprising at least the biomarkers shown in any one of Table 17 to 26, said detector allowing for the determination of the amounts of the biomarkers of the said group of biomarkers in the sample; and operatively linked thereto, (b) an evaluation unit comprising a data processing unit and a data base, said data base comprising a stored reference and said data processing unit having tangibly embedded an algorithm for carrying out a comparison of the amounts of the biomarkers of the group of biomarkers determined by the analyzing unit and the stored reference and for generating an output information based on which the diagnosis can be established.

A device as used herein shall comprise at least the aforementioned units. The units of the device are operatively linked to each other. How to link the means in an operating manner will depend on the type of units included into the device. For example, where the detector allows for automatic qualitative or quantitative determination of the biomarker, the data obtained by said automatically operating analyzing unit can be processed by, e.g., a computer program in order to facilitate the assessment in the evaluation unit. Preferably, the units are comprised by a single device in such a case. Said device may accordingly include an analyzing unit for the biomarker and a computer or data processing device as evaluation unit for processing the resulting data for the assessment and for stabling the output information. Preferred devices are those which can be applied without the particular knowledge of a specialized clinician, e.g., electronic devices which merely require loading with a sample. The output information of the device, preferably, is a numerical value which allows drawing conclusions on the presence or absence of pancreatic cancer and, thus, is an aid for diagnosis. More preferably, the output information is a preliminary diagnosis or an aid for diagnosis based on the aforementioned numerical value, i.e. a classifier which indicates whether the subject suffers from pancreatic cancer or not. Such a preliminary diagnosis may need the evaluation of further information which can be provided in the device of the invention by including an expert knowledge database system.

A preferred reference to be used as a stored reference in accordance with the device of the present invention is an amount for the at least one biomarker to be analyzed or values derived therefrom which are derived from a subject or group of subjects known to suffer from pancreatic cancer as referred to elsewhere herein. In such a case, the algorithm tangibly embedded, preferably, compares the determined amount for the at least one biomarker with the reference wherein an identical or essentially identical amount or value shall be indicative for the presence of pancreatic cancer in the subject.

Alternatively, another preferred reference to be used as a stored reference in accordance with the device of the present invention is an amount for the at least one biomarker to be analyzed or values derived therefrom which are derived from a subject or group of subjects known not to suffer from pancreatic cancer as referred to elsewhere herein. In such a case, the algorithm tangibly embedded, preferably, compares the determined amount for the at least one biomarker with the reference wherein an amount or value which differs from the reference shall be indicative for the presence of pancreatic cancer in the subject. Preferred differences are those indicated as relative changes or degrees of changes for the individual biomarkers in the Tables below.

The units of the device, also preferably, can be implemented into a system comprising several devices which are operatively linked to each other. Depending on the units to be used for the system of the present invention, said means may be functionally linked by connecting each mean with the other by means which allow data transport in between said means, e.g., glass fiber cables, and other cables for high throughput data transport. Nevertheless, wireless data transfer between the means is also envisaged by the present invention, e.g., via LAN (Wireless LAN, W-LAN). A preferred system comprises means for determining biomarkers. Means for determining biomarkers as used herein encompass means for separating biomarkers, such as chromatographic devices, and means for metabolite determination, such as mass spectrometry devices. Suitable devices have been described in detail above. Preferred means for compound separation to be used in the system of the present invention include chromatographic devices, more preferably devices for liquid chromatography, HPLC, and/or gas chromatography. Preferred devices for compound determination comprise mass spectrometry devices, more preferably, GC-MS, LC-MS, direct infusion mass spectrometry, FT-ICR-MS, CE-MS, HPLC-MS, quadrupole mass spectrometry, sequentially coupled mass spectrometry (including MS-MS or MS-MS-MS), ICP-MS, Py-MS or TOF. The separation and determination means are, preferably, coupled to each other. Most preferably, LC-MS and/or GC-MS are used in the system of the present invention as described in detail elsewhere in the specification. Further comprised shall be means for comparing and/or analyzing the results obtained from the means for determination of biomarkers. The means for comparing and/or analyzing the results may comprise at least one databases and an implemented computer program for comparison of the results. Preferred embodiments of the aforementioned systems and devices are also described in detail below.

Furthermore, the present invention relates to a data collection comprising characteristic values of the biomarkers of the group of biomarkers being indicative for a medical condition or effect as set forth above (i.e. diagnosing pancreatic cancer in a subject, identifying whether a subject is in need for a therapy of pancreatic cancer).

The term "data collection" refers to a collection of data which may be physically and/or logically grouped together. Accordingly, the data collection may be implemented in a single data storage medium or in physically separated data storage media being operatively linked to each other. Preferably, the data collection is implemented by means of a database. Thus, a database as used herein comprises the data collection on a suitable storage medium. Moreover, the database, preferably, further comprises a database management system. The database management system is, preferably, a network-based, hierarchical or object-oriented database management system. Furthermore, the database may be a federal or integrated database. More preferably, the database will be implemented as a distributed (federal) system, e.g. as a Client-Server-System. More preferably, the database is structured as to allow a search algorithm to compare a test data set with the data sets comprised by the data collection. Specifically, by using such an algorithm, the database can be searched for similar or identical data sets being indicative for a medical condition or effect as set forth above (e.g. a query search). Thus, if an identical or similar data set can be identified in the data collection, the test data set will be associated with the said medical condition or effect. Consequently, the information obtained from the data collection can be used, e.g., as a reference for the methods of the present invention described above. More preferably, the data collection comprises characteristic values of all biomarkers comprised by any one of the groups recited above.

In light of the foregoing, the present invention encompasses a data storage medium comprising the aforementioned data collection.

The term "data storage medium" as used herein encompasses data storage media which are based on single physical entities such as a CD, a CD-ROM, a hard disk, optical storage media, or a diskette. Moreover, the term further includes data storage media consisting of physically separated entities which are operatively linked to each other in a manner as to provide the aforementioned data collection, preferably, in a suitable way for a query search.

The present invention also relates to a system comprising:
(a) means for comparing characteristic values of the biomarkers of the group of biomarkers comprised in a sample operatively linked to
(b) a data storage medium as described above.

The term "system" as used herein relates to different means which are operatively linked to each other. Said means may be implemented in a single device or may be physically separated devices which are operatively linked to each other. The means for comparing characteristic values of biomarkers, preferably, based on an algorithm for comparison as mentioned before. The data storage medium, preferably, comprises the aforementioned data collection or database, wherein each of the stored data sets being indicative for a medical condition or effect referred to above. Thus, the system of the present invention allows identifying whether a test data set is comprised by the data collection stored in the data storage medium. Consequently, the methods of the present invention can be implemented by the system of the present invention.

In a preferred embodiment of the system, means for determining characteristic values of biomarkers of a sample are comprised. The term "means for determining characteristic values of biomarkers" preferably relates to the aforementioned devices for the determination of metabolites such as mass spectrometry devices, NMR devices or devices for carrying out chemical or biological assays for the biomarkers.

Moreover, the present invention relates to a diagnostic means comprising means for the determination of the biomarkers comprised in the group of biomarkers referred to above.

The term "diagnostic means", preferably, relates to a diagnostic device, system or biological or chemical assay as specified elsewhere in the description in detail.

The expression "means for the determination of the biomarkers" refers to devices or detection agents which are capable of specifically recognizing the biomarker. Suitable devices may be spectrometric devices such as mass spectrometry, NMR devices or devices for carrying out chemical or biological assays for the biomarkers. Suitable detection agents may be compounds which specifically detect the biomarkers. Detection as used herein may be a two-step process, i.e. the compound may first bind specifically to the biomarker to be detected and subsequently generate a detectable signal, e.g., fluorescent signals, chemiluminescent signals, radioactive signals and the like. For the generation of the detectable signal further compounds may be required which are all comprised by the term "means for determination of the at least one biomarker". Compounds which specifically bind to the biomarker are described elsewhere in the specification in detail and include, preferably, enzymes, antibodies, aptameres, ligands, receptors or other biological molecules or chemicals which specifically bind to the biomarkers.

Further, the present invention relates to a diagnostic composition comprising the biomarkers comprised in the group of biomarkers referred to above.

The group of biomarkers will be an indicator molecule for a medical condition or effect in the subject as set for the elsewhere herein. Thus, the biomarker molecules itself may serve as diagnostic compositions, preferably, upon visualization or detection by the means referred to in herein. Thus, a diagnostic composition which indicates the presence of a biomarker according to the present invention may also comprise the said biomarker physically, e.g., a complex of an antibody and the biomarker to be detected may serve as the diagnostic composition. Accordingly, the diagnostic composition may further comprise means for detection of the metabolites as specified elsewhere in this description. Alternatively, if detection means such as MS or NMR based techniques are used, the molecular species which serves as an indicator for the risk condition will be the at least one biomarker comprised by the test sample to be investigated. Thus, the at least one biomarker referred to in accordance with the present invention shall serve itself as a diagnostic composition due to its identification as a biomarker.

In general, the present invention contemplates the use a group of biomarkers said group comprising at least the biomarkers of one of the combinations shown in Table 1a or comprising at least the biomarkers shown in any one of Table 17 to 26 or a detection agent therefor in a sample of a subject suspected to suffer from pancreatic cancer for diagnosing pancreatic cancer or for distinguishing between pancreatic cancer and pancreatitis. Moreover, the present invention relates to the use of a group of biomarkers said group comprising at least the biomarkers of one of the combinations shown in Table 1a or comprising at least the biomarkers shown in any one of Table 17 to 26 or a detection agent therefor for the manufacture of a diagnostic or pharmaceutical composition for diagnosing pancreatic cancer or for distinguishing between pancreatic cancer and pancreatitis.

Further, the present invention relates to a method for diagnosing pancreas cancer in a subject comprising the steps of:
(a) determining in a sample of a subject suspected to suffer from pancreas cancer the amount of at least one biomarker from Table 28; and
(b) comparing the said amount of the at least one biomarker with a reference, whereby pancreas cancer is to be diagnosed.

More typically, the said method for diagnosing pancreas cancer in a subject comprises the steps of:
(a) selecting a subject which is suspected to suffer from pancreatic cancer;
(b) obtaining a test sample from said subject;
(c) pre-treating said test sample for analysis of the biomarkers comprised therein;
(d) determining the amount of at least one biomarker shown in Table 28, preferably, by contacting the sample with a detection agent, such as an antibody or aptamer, which specifically binds to said biomarker (and which upon binding can be detected such that the amount of said biomarker is determined;
(e) comparing the said amount of the biomarker with a reference for the biomarker; and
(f) based on the comparison of step (e), diagnose the presence or absence of pancreatic cancer.

The present invention also relates to a device or system for diagnosing pancreas cancer in a sample of a subject comprising:
(a) an analyzing unit for the said sample of the subject comprising a detector for at least one biomarker of Table 28 said detector allowing for the determination of the amount of the said at least one biomarker in the sample; and operatively linked thereto,
(b) an evaluation unit comprising a data processing unit and a data base, said data base comprising a stored reference, preferably a reference as specified above in connection with the method of the invention and, more preferably, a reference derived from a subject or group of subjects known to suffer from pancreas cancer, and said data processing unit having tangibly embedded an algorithm for carrying out a comparison, preferably as specified above in connection with the method of the invention, of the amount of the at least one biomarker determined by the analyzing unit and the stored reference and for generating an output information based on which the diagnosis can be established.

Finally, in general, the present invention contemplates the use of at least one biomarker of Table 28 or a detection agent therefor for diagnosing pancreatic cancer in a sample of a subject. Moreover the invention relates to the use of at least one biomarker of Table 28 in a sample of a subject or a detection agent therefor for the manufacture of a diagnostic or pharmaceutical composition for diagnosing pancreatic cancer.

Further, the present invention relates to a method for differentiating between pancreas cancer and pancreatitis in a subject comprising the steps of:
(a) determining in a sample of a subject suspected to suffer from pancreas cancer the amount of at least one biomarker from Table 29, 30, 31, 30a, or 38; and
(b) comparing the said amount of the at least one biomarker with a reference, whereby it is differentiated between pancreas cancer and pancreatitis.

More typically, the said method for differentiating between pancreas cancer and pancreatitis in a subject comprises the steps of:
(a) selecting a subject which is suspected to suffer from pancreatic cancer and/or pancreatitis;
(b) obtaining a test sample from said subject;
(c) pre-treating said test sample for analysis of the biomarkers comprised therein;
(d) determining the amount of at least one biomarker shown in Table 29, 30, 31, 30a, or 38, preferably, by contacting the sample with a detection agent, such as an antibody or aptamer, which specifically binds to the biomarker and which upon binding can be detected such that the amount of the biomarker is determined;
(e) comparing the said amount of the biomarker with a reference; and
(f) based on the comparison of step (e), differentiate between pancreatic cancer and pancreatitis.

Preferably, the sample is a serum sample if the at least one biomarker is from Table 29. Preferably, the sample is a plasma sample if the at least one biomarker is from Table 30, or, in a preferred embodiment, Table 30a. Moreover, the sample is preferably a plasma or serum sample if the at least one biomarker is from Table 31. In a preferred embodiment, the at least one biomarker is from Table 38 and the pancreatic cancer is pancreatic cancer stage I or II, i.e., preferably, resectable pancreatic cancer, wherein the sample, preferably, is a plasma sample.

The present invention also relates to a device or system for differentiating between pancreas cancer and pancreatitis in a sample of a subject comprising:
(a) an analyzing unit for the said sample of the subject comprising a detector for at least one biomarker of Table 29, 30, 31, 30a, or 38, said detector allowing for the determination of the amount of the said at least one biomarker in the sample; and operatively linked thereto,
(b) an evaluation unit comprising a data processing unit and a data base, said data base comprising a stored reference, preferably a reference as specified above in connection with the method of the invention and, more preferably, a reference derived from a subject or group of subjects known to suffer from pancreas cancer or pancreatitis, and said data processing unit having tangibly embedded an algorithm for carrying out a comparison, preferably as specified above in connection with the method of the invention, of the amount of the at least one biomarker determined by the analyzing unit and the stored reference and for generating an output information based on which the diagnosis can be established.

Finally, in general, the present invention contemplates the use of at least one biomarker of Table 29, 30, 31, 30a, or 38, or a detection agent therefor in a sample of a subject for differentiating between pancreas cancer and pancreatitis. Moreover the invention relates to the use of at least one biomarker of Table 29, 30, 31, 30a, or 38, in a sample of a subject or a detection agent therefor for the manufacture of a diagnostic or pharmaceutical composition for differentiating between pancreas cancer and pancreatitis.

Further, the present invention relates to a method for diagnosing pancreas cancer in a subject comprising the steps of:
(a) determining in a sample of a subject suspected to suffer from pancreas cancer the amount of at least one biomarker from Table 32, 33, 33a, or 39, and
(b) comparing the said amount of the at least one biomarker with a reference, whereby pancreas cancer is to be diagnosed.

More typically, the said method for diagnosing pancreas cancer in a subject comprising the steps of:
(a) selecting a subject which is suspected to suffer from pancreatic cancer;
(b) obtaining a test sample from said subject;
(c) pre-treating said test sample for analysis of the biomarkers comprised therein;
(d) determining the amount of at least one biomarker shown in Table 32, 33, 33a, or 39, preferably, by contacting the sample with a detection agent, such as an antibody or aptamer, which specifically binds to said biomarker and which upon binding can be detected such that the amount of the biomarker is determined;
(e) comparing the said amount of said group of biomarkers with a reference; and
(f) based on the comparison of step (e), diagnose the presence or absence of pancreatic cancer.

The present invention also relates to a device or system for diagnosing pancreas cancer in a sample of a subject comprising:
(a) an analyzing unit for the said sample of the subject comprising a detector for at least one biomarker of Table 32, 33, 33a, or 39 said detector allowing for the determination of the amount of the said at least one biomarker in the sample; and operatively linked thereto,
(b) an evaluation unit comprising a data processing unit and a data base, said data base comprising a stored reference, preferably a reference as specified above in connection with the method of the invention and, more preferably, a reference derived from a subject or group of subjects known to suffer from pancreas cancer, and said data processing unit having tangibly embedded an algorithm for carrying out a comparison, preferably as specified above in connection with the method of the invention, of the amount of the at least one biomarker determined by the analyzing unit and the stored reference and for generating an output information based on which the diagnosis can be established.

Finally, in general, the present invention contemplates the use of at least one biomarker of Table 32, 33, 33a, or 39, or a detection agent therefor for diagnosing pancreatic cancer in a sample of a subject. Moreover the invention relates to the use of at least one biomarker of Table 32, 33, 33a, or 39 in a sample of a subject or a detection agent therefor for the manufacture of a diagnostic or pharmaceutical composition for diagnosing pancreatic cancer.

Preferably, the sample is a serum sample if the at least one biomarker is from Table 32. Preferably, the sample is a plasma sample if the at least one biomarker is from Table 33 or 33a. In a preferred embodiment, the at least one biomarker is from Table 39 and the pancreatic cancer is pancreatic cancer stage I or II, i.e., preferably, resectable pancreatic cancer and the sample, preferably, is a plasma sample.

Further, the present invention relates to a method for differentiating between pancreas cancer and critical controls (i.e. subjects suffering from pancreatitis and liver cirrhosis) in a subject comprising the steps of:
(a) determining in a sample of a subject suspected to suffer from pancreas cancer the amount of at least one biomarker from Table 34 or 35; and (b) comparing the said amount of the at least one biomarker with a reference, whereby it is differentiated between pancreas cancer and critical controls (pancreatitis and liver cirrhosis)

More typically, the said method for differentiating between pancreas cancer and critical controls in a subject is comprising the steps of:
(a) selecting a subject which is suspected to suffer from pancreatic cancer or from pancreatitis or liver cirrhosis;
(b) obtaining a test sample from said subject;
(c) pre-treating said test sample for analysis of the biomarkers comprised therein;
(d) determining the amount of at least one biomarker shown in Table 34 or 35, preferably, by contacting the sample with a detection agent, such as an antibody or aptamer, which specifically binds to the biomarker and which upon binding can be detected such that the amount for the biomarker is determined;
(e) comparing the said amount of the biomarker with a reference; and
(f) based on the comparison of step (e), differentiate between pancreatic cancer and critical controls.

Preferably, the sample is a serum sample if the at least one biomarker is from Table 35. Preferably, the sample is a plasma sample if the at least one biomarker is from Table 34. The present invention also relates to a device or system for differentiating between pancreas cancer and critical controls (pancreatitis and liver cirrhosis) in a sample of a subject comprising:
(a) an analyzing unit for the said sample of the subject comprising a detector for at least one biomarker of Table 34 or 35 said detector allowing for the determination of the amount of the said at least one biomarker in the sample; and operatively linked thereto,
(b) an evaluation unit comprising a data processing unit and a data base, said data base comprising a stored reference, preferably a reference as specified above in connection with the method of the invention and, more preferably, a reference derived from a subject or group of subjects known to suffer from pancreas cancer or from pancreatitis or liver cirrhosis (critical controls), and said data processing unit having tangibly embedded an algorithm for carrying out a comparison, preferably as specified above in connection with the method of the invention, of the amount of the at least one biomarker determined by the analyzing unit and the stored reference and for generating an output information based on which the diagnosis can be established.

Finally, in general, the present invention contemplates the use of at least one biomarker of Table 34 or 35 or a detection agent therefor for differentiating between pancreas cancer and critical controls in a sample of a subject. Moreover the invention relates to the use of at least one biomarker of Table 34 or 35 in a sample of a subject or a detection agent therefor for the manufacture of a diagnostic or pharmaceutical composition for differentiating between pancreas cancer and critical controls (pancreatitis and liver cirrhosis)

Further, the present invention relates to a method for differentiating between pancreatic cancer and liver cirrhosis in a subject comprising the steps of:
(a) determining in a sample of a subject suspected to suffer from pancreas cancer or liver cirrhosis the amount of at least one biomarker from Table 36 or 37; and
(b) comparing the said amount of the at least one biomarker with a reference, whereby it is differentiated between pancreas cancer and liver cirrhosis.

More typically, the said method for differentiating between pancreas cancer and liver cirrhosis in a subject is comprising the steps of:
(a) selecting a subject which is suspected to suffer from pancreatic cancer and/or liver cirrhosis;
(b) obtaining a test sample from said subject;
(c) pre-treating said test sample for analysis of the biomarkers comprised therein;
(d) determining the amount of at least one biomarker shown in Table 36 or 37, preferably, by contacting the sample with a detection agent, such as an antibody or aptamer, which specifically binds to the biomarker and which upon binding can be detected such that the amount for the biomarker is determined;
(e) comparing the said amount of the biomarker with a reference s; and
(f) based on the comparison of step (e), differentiate between pancreatic cancer and liver cirrhosis.

Preferably, the sample is a serum sample if the at least one biomarker is from Table 36. Preferably, the sample is a plasma sample if the at least one biomarker is from Table 37.

The present invention also relates to a device or system for differentiating between pancreas cancer and liver cirrhosis in a sample of a subject comprising:
(a) an analyzing unit for the said sample of the subject comprising a detector for at least one biomarker of Table 36 or 37 said detector allowing for the determination of the amount of the said at least one biomarker in the sample; and operatively linked thereto,
(b) an evaluation unit comprising a data processing unit and a data base, said data base comprising a stored reference, preferably a reference as specified above in connection with the method of the invention and, more preferably, a reference derived from a subject or group of subjects known to suffer from pancreas cancer or liver cirrhosis, and said data processing unit having tangibly embedded an algorithm for carrying out a comparison, preferably as specified above in connection with the method of the invention, of the amount of the at least one biomarker determined by the analyzing unit and the stored reference and for generating an output information based on which the diagnosis can be established.

Finally, in general, the present invention contemplates the use of at least one biomarker of Table 36 or 37 or a detection agent therefor for differentiating between pancreas cancer and liver cirrhosis in a sample of a subject. Moreover the invention relates to the use of at least one biomarker of Table 36 or 37 in a sample of a subject or a detection agent therefor for the manufacture of a diagnostic or pharmaceutical composition for differentiating between pancreas cancer and liver cirrhosis.

In view of the above, the following embodiments are preferred:

Embodiment 1

A method for diagnosing pancreas cancer in a subject comprising the steps of:
a) determining in a sample of a subject suspected to suffer from pancreas cancer the amounts of a group of biomarkers said group comprising at least the biomarkers of one of the combinations shown in Table 1a or comprising at least the biomarkers shown in any one of Table 17 to 26 and b) comparing the said amounts of the biomarkers with references, whereby pancreas cancer is to be diagnosed.

Embodiment 2

The method of embodiment 1, wherein said subject is suspected to suffer from pancreas cancer or from chronic pancreatitis.

Embodiment 3

The method of embodiment 1 or 2, wherein said references are derived from a sample of a subject or a group of subjects known to suffer from pancreatic cancer.

Embodiment 4

The method of embodiment 1 or 2, wherein said references are derived from a sample of a subject or a group of subjects known not to suffer from pancreatic cancer.

Embodiment 5

The method of any one of embodiments 1 to 4, wherein said group of biomarkers comprises at least one further biomarker selected from Table 16.

Embodiment 6

The method of any one of embodiments 1 to 4, wherein said group of biomarkers is a group shown in any one of Tables 2 to 15.

Embodiment 7

The method of any one of embodiments 1 to 6, wherein the said group of biomarkers further comprises CA19-9.

Embodiment 8

The method of any one of embodiments 1 to 7, wherein said diagnosing comprises differentiating between pancreatic cancer and pancreatitis.

Embodiment 9

A method for identifying whether a subject is in need of a pancreas cancer therapy comprising the steps of the method of any one of embodiments 1 to 8 and the further step of identifying a subject in need of a pancreas cancer therapy if said subject is to be diagnosed to suffer from pancreas cancer.

Embodiment 10

The method of embodiment 9, wherein said pancreas cancer therapy comprises surgery, radiotherapy or drug treatment.

Embodiment 11

The method of any one of embodiments 1 to 10, wherein said sample is a plasma, blood or serum sample.

Embodiment 12

The method of any one of embodiments 1 to 11, wherein said sphingomyelin, ceramide and/or phosphorylated sphingobase is selected from those listed in Table 1b.

Embodiment 13

The method of any one of embodiments 1 to 12, wherein said pancreas cancer is pancreas adenocarcinoma.

Embodiment 14

The method of any one of embodiments 1 to 13, wherein said method is an ex vivo method.

Embodiment 15

The method of any one of embodiments 1 to 14, wherein said method comprises determining the amounts of a group of biomarkers as listed in one of Tables 2 to 15.

Embodiment 16

The method of any one of embodiments 1 to 15, wherein said method comprises, preferably is preceded by, determining the blood glucose level in said subject.

Embodiment 17

A device for diagnosing pancreas cancer in a sample of a subject comprising:
  a) an analyzing unit for the said sample of the subject comprising a detector for the amounts of a group of biomarkers said group comprising at least the biomarkers of one of the combinations shown in Table 1a or comprising at least the biomarkers shown in any one of Tables 17 to 26, said detector allowing for the determination of the amounts of the biomarkers of the said group of biomarkers in the sample; and operatively linked thereto,
  b) an evaluation unit comprising a data processing unit and a data base, said data base comprising a stored reference and said data processing unit having tangibly embedded an algorithm for carrying out a comparison of the amounts of the biomarkers of the group of biomarkers determined by the analyzing unit and the stored reference and for generating an output information based on which the diagnosis can be established.

Embodiment 18

A method for diagnosing pancreas cancer or for distinguishing between pancreatic cancer and pancreatitis in a subject comprising the steps of:
  a) selecting a subject which is suspected to suffer from pancreatic cancer;
  b) obtaining a test sample from said subject;
  c) pre-treating said test sample for analysis of the biomarkers comprised therein;
  d) determining the amounts of a group of biomarkers said group comprising at least the biomarkers of one of the combinations shown in Table 1a or comprising at least the biomarkers shown in any one of Table 17 to 26, preferably, by contacting the sample with detection agents, such as antibodies or aptamers, which specifically bind to the biomarkers of the group of biomarkers and which upon binding can be detected such that the amounts of the biomarker are determined;

e) comparing the said amounts of the biomarkers with references for each of the biomarkers; and
f) based on the comparison of step (e), diagnose the presence or absence of pancreatic cancer or distinguish between pancreatic cancer and pancreatitis.

Embodiment 19

The method of embodiment 18, wherein step d) is carried out by an analyzing unit of a device according to embodiment 17.

Embodiment 20

The method of embodiment 18 or 19, wherein step(s) e) and/or f) is (are) carried out by an analyzing unit of a device according to embodiment 17.

Embodiment 21

Use of a group of biomarkers, said group comprising at least the biomarkers of one of the combinations shown in Table 1a or comprising at least the biomarkers shown in any one of Table 17 to 26 or a detection agent therefor in a sample of a subject suspected to suffer from pancreatic cancer for diagnosing pancreatic cancer.

Embodiment 22

A method for identifying whether a subject is in need of a pancreas cancer therapy comprising the steps of one of the methods of any one of embodiments 1 to 20 and the further step of identifying a subject in need of a pancreas cancer therapy if said subject is to be diagnosed to suffer from pancreas cancer.

Embodiment 23

The method of embodiment 22, further comprising the step of recommending a therapeutic or patient health management measure for the subject based on whether the subject is diagnosed to suffer from pancreatic cancer or from pancreatitis.

Embodiment 24

A data collection comprising characteristic values of the biomarkers of the group of biomarkers being indicative for diagnosing pancreatic cancer in a subject or for identifying whether a subject is in need for a therapy of pancreatic cancer.

Embodiment 25

A data storage medium comprising the data collection of embodiment 24.

Embodiment 26

A system comprising:
a) means for comparing characteristic values of the biomarkers of the group of biomarkers comprised in a sample operatively linked to
b) a data storage medium according to embodiment 25.

Embodiment 27

A diagnostic composition comprising the biomarkers comprised in a group of biomarkers of any of the aforementioned embodiments.

Embodiment 28

A method for diagnosing pancreas cancer in a subject comprising the steps of:
a) determining in a sample of a subject suspected to suffer from pancreas cancer the amount of at least one biomarker from Table 28; and
b) comparing the said amount of the at least one biomarker with a reference, whereby pancreas cancer is to be diagnosed.

Embodiment 29

The method of embodiment 28, comprising the steps of:
a) selecting a subject which is suspected to suffer from pancreatic cancer;
b) obtaining a test sample from said subject;
c) pre-treating said test sample for analysis of the biomarkers comprised therein;
d) determining the amount of at least one biomarker shown in Table 28;
e) comparing the said amount of the biomarker with a reference for the biomarker; and
f) based on the comparison of step (e), diagnose the presence or absence of pancreatic cancer.

Embodiment 30

A device or system for diagnosing pancreas cancer in a sample of a subject comprising:
a) an analyzing unit for the said sample of the subject comprising a detector for at least one biomarker of Table 28 said detector allowing for the determination of the amount of the said at least one biomarker in the sample; and operatively linked thereto,
b) an evaluation unit comprising a data processing unit and a data base, said data base comprising a stored reference and said data processing unit having tangibly embedded an algorithm for carrying out a comparison of the amount of the at least one biomarker determined by the analyzing unit and the stored reference and for generating an output information based on which the diagnosis can be established.

Embodiment 31

Use of at least one biomarker of Table 28 or a detection agent therefor for diagnosing pancreatic cancer in a sample of a subject.

Embodiment 32

Use of at least one biomarker of Table 28 in a sample of a subject or a detection agent therefor for the manufacture of a diagnostic or pharmaceutical composition for diagnosing pancreatic cancer.

Embodiment 33

A method for differentiating between pancreas cancer and pancreatitis in a subject comprising the steps of:
a) determining in a sample of a subject suspected to suffer from pancreas cancer the amount of at least one biomarker from Table 29, 30, 31, 30a, or 38; and
b) comparing the said amount of the at least one biomarker with a reference, whereby it is differentiated between pancreas cancer and pancreatitis.

Embodiment 34

The method of embodiment 33, comprising the steps of:
a) selecting a subject which is suspected to suffer from pancreatic cancer;
b) obtaining a test sample from said subject;
c) pre-treating said test sample for analysis of the biomarkers comprised therein;
d) determining the amount of at least one biomarker shown in Table 29, 30, 31, 30a, or 38;
e) comparing the said amount of the biomarker with a reference for the biomarker; and
f) based on the comparison of step (e), diagnose the presence or absence of pancreatic cancer.

Embodiment 35

A device or system for diagnosing pancreas cancer in a sample of a subject comprising:
a) an analyzing unit for the said sample of the subject comprising a detector for at least one biomarker of Table 29, 30, 31, 30a, or 38, said detector allowing for the determination of the amount of the said at least one biomarker in the sample; and operatively linked thereto,
b) an evaluation unit comprising a data processing unit and a data base, said data base comprising a stored reference and said data processing unit having tangibly embedded an algorithm for carrying out a comparison of the amount of the at least one biomarker determined by the analyzing unit and the stored reference and for generating an output information based on which the diagnosis can be established.

Embodiment 36

Use of at least one biomarker of Table 29, 30, 31, 30a, or 38, or a detection agent therefor in a sample of a subject for differentiating between pancreas cancer and pancreatitis.

Embodiment 37

Use of at least one biomarker of Table 29, 30, 31, 30a, or 38, in a sample of a subject or a detection agent therefor for the manufacture of a diagnostic or pharmaceutical composition for differentiating between pancreas cancer and pancreatitis.

Embodiment 38

The method of embodiment 33 or 34, the device of embodiment 35, or the use of embodiment 36 or 37, wherein
(i) the sample is a serum sample and the at least one biomarker is from Table 29;
(ii) the sample is a plasma sample and the at least one biomarker is from Table 30 or Table 30a;
(iii) the sample is a plasma or a serum sample and the at least one biomarker is from Table 31, or
(iv) the pancreas cancer is pancreas cancer stage I or II (resectable pancreas cancer) and the at least one biomarker is from Table 38 and, preferably, the sample is a plasma sample.

Embodiment 39

A method for diagnosing pancreas cancer in a subject comprising the steps of:
a) determining in a sample of a subject suspected to suffer from pancreas cancer the amount of at least one biomarker from Table 32, 33, 33a, or 39, and
b) comparing the said amount of the at least one biomarker with a reference, whereby pancreas cancer is to be diagnosed.

Embodiment 40

The method of embodiment 39, comprising the steps of:
a) selecting a subject which is suspected to suffer from pancreatic cancer;
b) obtaining a test sample from said subject;
c) pre-treating said test sample for analysis of the biomarkers comprised therein;
d) determining the amount of at least one biomarker shown in Table 32, 33, 33a, or 39, preferably, by contacting the sample with a detection agent, such as an antibody or aptamer, which specifically binds to said biomarker and which upon binding can be detected such that the amount of the biomarker is determined;
e) comparing the said amount of said group of biomarkers with a reference; and
f) based on the comparison of step (e), diagnose the presence or absence of pancreatic cancer.

Embodiment 41

A device or system for diagnosing pancreas cancer in a sample of a subject comprising:
a) an analyzing unit for the said sample of the subject comprising a detector for at least one biomarker of Table 32, 33, 33a, or 39 said detector allowing for the determination of the amount of the said at least one biomarker in the sample; and operatively linked thereto,
b) an evaluation unit comprising a data processing unit and a data base, said data base comprising a stored reference, and said data processing unit having tangibly embedded an algorithm for carrying out a comparison of the amount of the at least one biomarker determined by the analyzing unit and the stored reference and for generating an output information based on which the diagnosis can be established.

Embodiment 42

Use of at least one biomarker of Table 32, 33, 33a, or 39, or a detection agent therefor for diagnosing pancreatic cancer in a sample of a subject.

Embodiment 43

Use of at least one biomarker of Table 32, 33, 33a, or 39 in a sample of a subject or a detection agent therefor for the manufacture of a diagnostic or pharmaceutical composition for diagnosing pancreatic cancer.

Embodiment 44

The method of embodiment 39 or 40, the device of embodiment 41, or the use of embodiment 42 or 43, wherein
(i) the sample is a serum sample and the at least one biomarker is from Table 32;
(ii) the sample is a plasma sample and the at least one biomarker is from Table 33a;

(iii) the sample is a plasma or a serum sample and the at least one biomarker is from Table 33; or
(iv) the pancreas cancer is pancreas cancer stage I or II (resectable pancreas cancer) and the at least one biomarker is from Table 39 and, preferably, the sample is a plasma sample.

Embodiment 45

A method for differentiating between pancreas cancer and critical controls in a subject comprising the steps of:
a) determining in a sample of a subject suspected to suffer from pancreas cancer the amount of at least one biomarker from Table 34 or 35; and
b) comparing the said amount of the at least one biomarker with a reference, whereby it is differentiated between pancreas cancer and critical controls (pancreatitis and liver cirrhosis).

Embodiment 46

The method of embodiment 45, comprising the steps of:
a) selecting a subject which is suspected to suffer from pancreatic cancer or from pancreatitis or liver cirrhosis;
b) obtaining a test sample from said subject;
c) pre-treating said test sample for analysis of the biomarkers comprised therein;
d) determining the amount of at least one biomarker shown in Table 34 or 35;
e) comparing the said amount of the biomarker with a reference; and
f) based on the comparison of step (e), differentiate between pancreatic cancer and critical controls.

Embodiment 47

A device or system for differentiating between pancreas cancer and critical controls in a sample of a subject comprising:
a) an analyzing unit for the said sample of the subject comprising a detector for at least one biomarker of Table 34 or 35 said detector allowing for the determination of the amount of the said at least one biomarker in the sample; and operatively linked thereto,
b) an evaluation unit comprising a data processing unit and a data base, said data base comprising a stored reference and said data processing unit having tangibly embedded an algorithm for carrying out a comparison of the amount of the at least one biomarker determined by the analyzing unit and the stored reference and for generating an output information based on which the diagnosis can be established.

Embodiment 48

Use of at least one biomarker of Table 34 or 35 or a detection agent therefor for differentiating between pancreas cancer and critical controls in a sample of a subject.

Embodiment 49

Use of at least one biomarker of Table 34 or 35 in a sample of a subject or a detection agent therefor for the manufacture of a diagnostic or pharmaceutical composition for differentiating between pancreas cancer and critical controls.

Embodiment 50

The method of embodiment 45 or 46, the device or system of embodiment 47, or the use of embodiment 48 or 49, wherein
(i) the sample is a serum sample and the at least one biomarker is from Table 35; or
(ii) the sample is a plasma sample and the at least one biomarker is from Table 34.

Embodiment 51

The method of embodiment 45 or 46, the device or system of embodiment 47, or the use of embodiment 48 or 49, wherein said critical controls are pancreatitis and liver cirrhosis.

Embodiment 52

A method for differentiating between pancreatic cancer and liver cirrhosis in a subject comprising the steps of:
a) determining in a sample of a subject suspected to suffer from pancreas cancer or liver cirrhosis the amount of at least one biomarker from Table 36 or 37; and
b) comparing the said amount of the at least one biomarker with a reference, whereby it is differentiated between pancreas cancer and liver cirrhosis.

Embodiment 53

The method of embodiment 52, comprising the steps of:
a) selecting a subject which is suspected to suffer from pancreatic cancer and/or liver cirrhosis;
b) obtaining a test sample from said subject;
c) pre-treating said test sample for analysis of the biomarkers comprised therein;
d) determining the amount of at least one biomarker shown in Table 36 or 37;
e) comparing the said amount of the biomarker with a reference s; and
f) based on the comparison of step (e), differentiate between pancreatic cancer and liver cirrhosis.

Embodiment 54

A device or system for differentiating between pancreas cancer and liver cirrhosis in a sample of a subject comprising:
a) an analyzing unit for the said sample of the subject comprising a detector for at least one biomarker of Table 36 or 37 said detector allowing for the determination of the amount of the said at least one biomarker in the sample; and operatively linked thereto,
b) an evaluation unit comprising a data processing unit and a data base, said data base comprising a stored reference and said data processing unit having tangibly embedded an algorithm for carrying out a comparison of the amount of the at least one biomarker determined by the analyzing unit and the stored reference and for generating an output information based on which the diagnosis can be established.

Embodiment 55

Use of at least one biomarker of Table 36 or 37 or a detection agent therefor for differentiating between pancreas cancer and liver cirrhosis in a sample of a subject.

Embodiment 56

Use of at least one biomarker of Table 36 or 37 in a sample of a subject or a detection agent therefor for the manufacture of a diagnostic or pharmaceutical composition for differentiating between pancreas cancer and liver cirrhosis.

Embodiment 57

The method of embodiment 52 or 53, the device or system of embodiment 54, or the use of embodiment 55 or 56, wherein
(i) the sample is a serum sample and the at least one biomarker is from Table 36; or
(ii) the sample is a plasma sample if the at least one biomarker is from Table 37.

All references cited herein are herewith incorporated by reference with respect to their disclosure content in general or with respect to the specific disclosure contents indicated above.

EXAMPLES

The invention will now be illustrated by the following Examples which are not intended to restrict or limit the scope of this invention.

Example 1: Patients, Plasma and Serum Preparation

A total of 474 patients with pancreatic cancer, chronic pancreatitis, liver cirrhosis and healthy blood donors were enrolled in the clinical study. In this retrospective case control study samples of: 158 patients suffering from pancreatic ductal adenocarcinoma (PDAC), 159 samples of chronic pancreatitis (CP) patients, samples of 80 patients suffering from liver cirrhosis (LC) and 77 samples of healthy volunteers (blood donors, BD) were included. All patients or their legal representatives gave their written informed consent and the local ethics review boards approved the protocol. Patients were consecutively recruited from two centers. After blood drawing and centrifugation, plasma or serum samples were collected in Eppendorf tubes and stored at −80° C. for further analysis. Sample processing was performed according to the institutional standard operating procedure. Exclusion criteria were a concomitant malignant disease, curative treatment of malignant disease less than 2 years of recruitment to the trial, concomitant cystic diseases of the pancreas, pregnancy or patients unable to give informed consent Example 2: Metabolite Profiling MxP® Broad and MxP® Steroids Three types of mass spectrometry analyses were applied to all samples. GC-MS (gas chromatography-mass spectrometry; Agilent 6890 GC coupled to an Agilent 5973 MSSystem, Agilent, Waldbronn, Germany) and LC-MS/MS [liquid chromatography-MS/MS; Agilent 1100 HPLCSystem (Agilent, Waldbronn, Germany) coupled to an Applied Biosystems API4000 MS/MSSystem (Applied Biosystems, Darmstadt, Germany)] were used for broad profiling [van Ravenzwaay, B. et al. The use of metabolomics for the discovery of new biomarkers of effect. *Toxicol Lett* 172, 21-8 (2007]. Solid phase extraction-LC-MS/MS [SPE-LC-MS/MS; Symbiosis Pharma (Spark, Emmen, Netherlands) coupled to an Applied Biosystems API4000 MS/MSSystem (Applied Biosystems, Darmstadt, Germany)] was used for the determination steroid levels. Fractionation and derivatisation of samples and detection technologies have been previously described [van Ravenzwaay, B. et al. The use of metabolomics for the discovery of new biomarkers of effect. *Toxicol Lett* 172, 21-8 (2007, Roessner, U., Wagner, C., Kopka, J., Trethewey, R. N. & Willmitzer, L. Technical advance: simultaneous analysis of metabolites in potato tuber by gas chromatography-mass spectrometry. *Plant J*23, 131-42 (2000), Mutch, D. M. et al. Metabolite profiling identifies candidate markers reflecting the clinical adaptations associated with Roux-en-Y gastric bypass surgery. *PLoS One* 4, e7905 (2009)]. Proteins were removed from plasma samples by precipitation. Subsequently polar and non-polar fractions were separated for both GC-MS and LC-MS/MS analyses by adding water and a mixture of ethanol and dichloromethane. For GC-MS analyses, the non-polar fraction was treated with methanol under acidic conditions to yield the fatty acid methyl esters derived from both free fatty acids and hydrolyzed complex lipids. The polar and non-polar fractions were further derivatized with O-methyl-hydroxyamine hydrochloride (20 mg/ml in pyridine, 50 II) to convert oxo-groups to O-methyloximes and subsequently with a silylating agent (MSTFA, 50 II) before GC-MS analysis. For LC-MS/MS analyses, both fractions were reconstituted in appropriate solvent mixtures. High performance LC (HPLC) was performed by gradient elution using methanol/water/formic acid on reversed phase separation columns. Mass spectrometric detection technology was applied as described in the U.S. Pat. No. 7,196,323, which allows targeted and high sensitivity "Multiple Reaction Monitoring" profiling in parallel to a full screen analysis. Steroids and their related metabolites were measured by online SPE-LC-MS/MS.

MxP® Lipids

Total lipids were extracted from plasma or serum by liquid/liquid extraction using chloroform/methanol. The lipid extracts were subsequently fractionated by normal phase liquid chromatography (NPLC) into eleven different lipid groups according to [Christie, W. W. Rapid separation and quantification of lipid classes by high performance liquid chromatography and mass (light-scattering) detection. *J Lipid Res* 26, 507-12 (1985)]. The fractions were analyzed by LCMS/MS using electrospray ionization (ESI) and atmospheric pressure chemical ionization (APCI) with detection of specific multiple reaction monitoring (MRM) transitions for cholesterol esters (CE), free sterols (FS), sphingoymelins (SM), and ceramides (CER) respectively. Sphingosines and sphingosine-1-phosphates (SP) were analyzed by LC-MS/MS using electrospray ionization (ESI) with detection of specific multiple reaction monitoring (MRM) transitions as described by [Schmidt, H., Schmidt, R. & Geisslinger, G. LC-MS/MS-analysis of sphingosine-1-phosphate and related compounds in plasma samples. *Prostaglandins Other Lipid Mediat* 81, 162-70 (2006)]. The lipid classes Monoacylglycerides (MAG), Triacylglycerides (TAG), Phosphatidylcholines (PC), Phosphatidylserines (PS), Phosphatidylinositoles (PI), Lysophosphatidylcholines (LPC), Diacylglycerols (DAG), Free fatty acids (FFA) were measured by GC-MS. The fractions are analyzed by GC-MS after derivatization with TMSH (Trimethyl sulfonium hydroxide), yielding the fatty acid methyl esters (FAME) corresponding to the acyl moieties of the class-separated lipids. The concentrations of FAME from C14 to C24 are determined in each fraction. In the tables below, any of the abbreviations above is used as prefix for a metabolite to indicate that the respective metabolite has been derived from the respective lipid or lipid fraction.

Example 3: Data Set Analysis and Normalization

Prior to statistical analysis, log 10 transformation of ratios was conducted to assure normaldistribution of data. The software R 2.8.1 (package nlme) was used for data analyses and visualizations. Statistical analysis was done by a simple linear model (ANOVA) with "disease", "age", "gender", "BMI", and "sample storage time", and "sample type" (plasma or serum), if appropriate, as fixed effects. Classification analysis with Random Forest (Liaw and Wiener (2002). Classification and Regression by random Forest. R News 2(3), 18-22.) and Elastic Net (Zou and Hastie (2005) Regularization and variable selection via the elastic net, Journal of the Royal Statistical Society, Series B) was done on log 10 transformed data including CA 19-9 or excluding CA19-9, as indicated in the panels. Feature selection was done by a forward search approach where the metabolite best correlating with the residuals of the last model is added to the next model. The inbuilt feature selection of Elastic Net was not applied. We used 10-fold crossvalidation with the feature selection embedded to repeatedly build a model on nine out of ten training folds to then estimate the AUC in an unbiased way on the test fold.

Afterwards the final set of metabolites was determined by retraining the classifier on the entire data. We analyzed three different data sets: (1) data of plasma samples, (2) data of serum samples, and (3) data of plasma and serum samples together. In the case (3), the sample type was used as fixed effect in the ANOVA analysis as described.

To analyse the performance of our selected panels, a classifier was built with a random forest or elastic net analysis with these sets of metabolites and the cross validated classification performance was estimated with the area under the curve (AUC) of a receiver operating characteristic (ROC) analysis. Performance calculations were carried out with or without prior ANOVA correction of metabolite data for confounding factors (age, gender, BMI, and sample type (if appropriate)).

All 95% confidence intervals for the AUC were derived upon the basis of the binormal model as described in Zhou, Obuchowski and McClish [Statistical Methods in Diagnostic Medicine (2011), 2nd Edition, by Zhou, Obuchowski and McClish.] The assumption of binormality was visually checked with a QQ-Plot.

The core panel was selected from results of multivariate analyses (Random Forest=RF)) and univariate analyses (ANOVA, ROC) for differential diagnosis between pancreatic cancer and pancreatitis as follows:

TABLE 1a

Combinations of biomarkers forming biomarker groups (core panels)

| Combination | Lysophosphatidylethanolamine (C18:2) | Sphingomyelin | Ceramide | Phosphorylated sphingobase |
|---|---|---|---|---|
| 1 | + | + | + | + |
| 2 | + | + | + |   |
| 3 | + | + |   | + |
| 4 | + | + |   |   |
| 5 | + |   | + | + |
| 6 | + |   | + |   |
| 7 | + |   |   | + |

+ = biomarker present in the combination; the sphingolipid shall have two hydroxyl groups, therefore denoted with the "d" nomenclature, and a sphingobase chain length of ≥7 C-atoms;;

In cases the biomarker candidates include CA19-9, this data may be applied as numerical or categorical data. Numerical CA19-9 data refer to the measured CA19-9 concentrations (U/ml) per subject. For the categorical data, a defined cut-off of 37 U/ml was used for dichotomization of the data into a low CA19-9 group 37 U/ml) and a high CA19-9 group (>37 U/ml); The analyses were done on the data of plasma samples, the data of serum samples and on a combined analysis of plasma and serum.

TABLE 1b

Directions of biomarker regulation, preferred ceramides, sphingomyelins, and phosphorylated sphingobases

| Metabolite | Direction in pancreatic cancer relative to pancreatitis |
|---|---|
| Lysophosphatidylethanolamine (C18:2) | down |
| Ceramide (d17:1,C16:0) | up |
| Ceramide (d18:1,C18:0) | up |
| Ceramide (d18:1,C24:0) | down |
| Sphinganine-1-phosphate (d18:0) | down |
| Sphingomyelin (d17:1,C16:0) | up |
| Sphingomyelin (d17:1,C16:0) | up |
| Sphingomyelin (d17:1,C16:0) | up |
| Sphingomyelin (d17:1,C18:0) | up |
| Sphingomyelin (d17:1,C18:0) | up |
| Sphingomyelin (d17:1,C20:0) | up |
| Sphingomyelin (d17:1,C24:1) | up |
| Sphingomyelin (d18:1,C18:0) | up |
| Sphingomyelin (d18:1,C18:1) | up |
| Sphingomyelin (d18:1,C19:0) | up |
| Sphingomyelin (d18:1,C20:1) | up |
| Sphingomyelin (d18:1,C22:1) | up |
| Sphingomyelin (d18:1,C23:1) | up |
| Sphingomyelin (d18:1,C24:1) | up |
| Sphingomyelin (d18:1,C24:2) | up |
| Sphingomyelin (d18:2,C17:0) | up |
| Sphingomyelin (d18:2,C19:0) | up |
| Sphingomyelin (d18:2,C20:1) | up |
| Sphingomyelin (d18:2,C21:0) | up |
| Sphingomyelin (d18:2,C22:1) | up |
| Sphingomyelin (d18:2,C24:2) | up |
| Sphingosine-1-phosphate (d18:1) | down |

TABLE 2

Panel Number 3, Algorithm ROC, Matrix Serum and plasma, CA19-9 excluded, no ANOVA Correction of data

| Metabolite | AUC estimate | direction from ANOVA |
|---|---|---|
| Sphingomyelin (d18:1,C19:0) | 0.7851 | up |
| Sphingomyelin (d18:2,C19:0) | 0.7719 | up |
| Sphingomyelin (d17:1,C18:0) | 0.7743 | up |
| Sphingomyelin (d17:1,C20:0) | 0.7511 | up |
| Sphingomyelin (d17:1,C24:1) | 0.7323 | up |
| Ceramide (d17:1,C16:0) | 0.7278 | up |
| 1-Hydroxy-2-amino-(cis,trans)-3,5-octadecadiene (from sphingolipids) | 0.7259 | up |
| Lysophosphatidylethanolamine (C18:2) | 0.7362 | down |
| Sphingomyelin (d17:1,C16:0) | 0.735 | up |
| Sphingomyelin (d17:1,C18:0) | 0.7286 | up |

TABLE 3

Panel Number 6, Algorithm RF, Matrix Serum and plasma, CA19-9 excluded, with ANOVA correction of data

| Metabolite | AUC estimate | direction from ANOVA |
|---|---|---|
| Sphingomyelin (d18:1,C19:0) | 0.8 | up |
| Sphingomyelin (d18:2,C22:1) | 0.8 | up |
| Citrulline | 0.8 | down |
| Glycocholic acid | 0.8 | up |

TABLE 3-continued

Panel Number 6, Algorithm RF, Matrix Serum and plasma, CA19-9 excluded, with ANOVA correction of data

| Metabolite | AUC estimate | direction from ANOVA |
|---|---|---|
| O-Acetylcarnitine | 0.8 | down |
| Eicosapentaenoic acid (C20:cis[5,8,11,14,17]5) | 0.8 | down |
| Sphinganine-1-phosphate (d18:0) | 0.8 | down |
| Serine | 0.8 | down |
| Sphingomyelin (d17:1,C16:0) | 0.8 | up |
| Lysophosphatidylethanolamine (C18:2) | 0.8 | down |

TABLE 4

Panel Number 7, Algorithm RF, Matrix Serum and plasma, CA19-9 numerical included, with ANOVA correction of data

| Metabolite | AUC estimate | direction from ANOVA |
|---|---|---|
| Sphingomyelin (d18:2,C22:1) | 0.9 | up |
| Aspartate | 0.9 | down |
| O-Acetylcarnitine | 0.9 | down |
| Hexanoylcarnitine | 0.9 | up |
| Eicosapentaenoic acid (C20:cis[5,8,11,14,17]5) | 0.9 | down |
| Sphinganine-1-phosphate (d18:0) | 0.9 | down |
| Proline | 0.9 | down |
| Sphingomyelin (d17:1,C16:0) | 0.9 | up |
| Lysophosphatidylethanolamine (C18:2) | 0.9 | down |
| CA19-9 | 0.9 | up |

TABLE 5

Panel Number 8, Algorithm RF, Matrix Plasma, CA19-9 excluded, with ANOVA correction of data

| Metabolite | AUC estimate | direction from ANOVA |
|---|---|---|
| Sphingomyelin (d18:2,C21:0) | 0.87 | up |
| gamma-Tocopherol | 0.87 | down |
| Sorbitol | 0.87 | down |
| Citrulline | 0.87 | down |
| Pregnenolone sulfate | 0.87 | down |
| Pipecolic acid | 0.87 | down |
| Propionylcarnitine | 0.87 | down |
| alpha-Ketoglutarate | 0.87 | up |
| Sphingomyelin (d17:1,C16:0) | 0.87 | up |
| Lysophosphatidylethanolamine (C18:2) | 0.87 | down |

TABLE 6

Panel Number 9, Algorithm RF, Matrix Plasma, CA19-9 numerical included, with ANOVA correction of data

| Metabolite | AUC estimate | direction from ANOVA |
|---|---|---|
| Propionylcarnitine | 0.95 | down |
| Eicosapentaenoic acid (C20:cis[5,8,11,14,17]5) | 0.95 | down |
| alpha-Ketoglutarate | 0.95 | up |
| Proline | 0.95 | down |
| Sphingomyelin (d18:1,C24:1) | 0.95 | up |
| Phosphatidylcholine (C18:0,C22:6) | 0.95 | up |
| Sphingomyelin (d17:1,C16:0) | 0.95 | up |
| Lysophosphatidylethanolamine (C18:2) | 0.95 | down |
| Sphingomyelin (d18:2,C17:0) | 0.95 | up |
| CA19-9 | 0.95 | up |

TABLE 7

Panel Number 12, Algorithm RF, Matrix Plasma, CA19-9 categorical included, with ANOVA correction of data

| Metabolite | AUC estimate | direction from ANOVA |
|---|---|---|
| Sphingomyelin (d18:2,C21:0) | 0.94 | up |
| gamma-Tocopherol | 0.94 | down |
| Citrulline | 0.94 | down |
| Creatinine | 0.94 | up |
| Propionylcarnitine | 0.94 | down |
| alpha-Ketoglutarate | 0.94 | up |
| Proline | 0.94 | down |
| Sphingomyelin (d17:1,C16:0) | 0.94 | up |
| Lysophosphatidylethanolamine (C18:2) | 0.94 | down |
| CA19-9 | 0.94 | up |

TABLE 8

Panel Number 14, Algorithm RF, Matrix Plasma, CA19-9 categorical included, no ANOVA correction of data

| Metabolite | AUC estimate | direction from ANOVA |
|---|---|---|
| gamma-Tocopherol | 0.93 | down |
| Palmitoleic acid (C16:cis[9]1) | 0.93 | down |
| Proline | 0.93 | down |
| Ketoleucine | 0.93 | down |
| Isocitrate | 0.93 | up |
| Phosphatidylcholine (C18:0,C22:6) | 0.93 | up |
| Sphingomyelin (d17:1,C16:0) | 0.93 | up |
| Lysophosphatidylethanolamine (C18:2) | 0.93 | down |
| Sphingomyelin (d18:2,C17:0) | 0.93 | up |
| CA19-9 | 0.93 | up |

TABLE 9

Panel Number 15, Algorithm RF, Matrix Serum and plasma, CA19-9 excluded, with ANOVA correction of data

| Metabolite | AUC estimate | direction from ANOVA |
|---|---|---|
| Sphingomyelin (d18:1,C19:0) | 0.8 | up |
| Sphingomyelin (d18:2,C22:1) | 0.8 | up |
| Citrulline | 0.8 | down |
| Glycocholic acid | 0.8 | up |
| O-Acetylcarnitine | 0.8 | down |
| Eicosapentaenoic acid (C20:cis[5,8,11,14,17]5) | 0.8 | down |
| Sphinganine-1-phosphate (d18:0) | 0.8 | down |
| Serine | 0.8 | down |
| Sphingomyelin (d17:1,C16:0) | 0.8 | up |
| Lysophosphatidylethanolamine (C18:2) | 0.8 | down |

TABLE 10

Panel Number 16, Algorithm RF, Matrix Serum and plasma, CA19-9 excluded, no ANOVA correction of data

| Metabolite | AUC estimate | direction from ANOVA |
|---|---|---|
| Sphingomyelin (d18:1,C19:0) | 0.85 | up |
| Coenzyme Q10 | 0.85 | down |
| Glycocholic acid | 0.85 | up |
| Docosahexaenoic acid (C22:cis[4,7,10,13,16,19]6) | 0.85 | up |
| Palmitoleic acid (C16:cis[9]1) | 0.85 | down |
| Lignoceric acid (C24:0) | 0.85 | down |
| 1,5-Anhydrosorbitol | 0.85 | down |

TABLE 10-continued

Panel Number 16, Algorithm RF, Matrix Serum and plasma, CA19-9 excluded, no ANOVA correction of data

| Metabolite | AUC estimate | direction from ANOVA |
| --- | --- | --- |
| Dehydroepiandrosterone sulfate | 0.85 | down |
| Lysophosphatidylethanolamine (C18:2) | 0.85 | down |

TABLE 11

Panel Number 17, Algorithm RF, Matrix Serum and plasma, CA19-9 categorical included, with ANOVA correction of data

| Metabolite | AUC estimate | direction from ANOVA |
| --- | --- | --- |
| Sphingomyelin (d18:2,C22:1) | 0.88 | up |
| Cryptoxanthin | 0.88 | up |
| Aspartate | 0.88 | down |
| O-Acetylcarnitine | 0.88 | down |
| Eicosapentaenoic acid (C20:cis[5,8,11,14,17]5) | 0.88 | down |
| Sphinganine-1-phosphate (d18:0) | 0.88 | down |
| Histidine | 0.88 | down |
| Sphingomyelin (d17:1,C16:0) | 0.88 | up |
| Lysophosphatidylethanolamine (C18:2) | 0.88 | down |
| CA19-9 | 0.88 | up |

TABLE 12

Panel Number 18, Algorithm RF, Matrix Serum and plasma, CA19-9 categorical included, no ANOVA correction of data

| Metabolite | AUC estimate | direction from ANOVA |
| --- | --- | --- |
| Sphingomyelin (d18:2,C19:0) | 0.91 | up |
| Ceramide (d18:1,C24:0) | 0.91 | down |
| Coenzyme Q10 | 0.91 | down |
| Sphinganine-1-phosphate (d18:0) | 0.91 | down |
| Histidine | 0.91 | down |
| Dehydroepiandrosterone sulfate | 0.91 | down |
| TAG (C18:2,C18:2) | 0.91 | up |
| Lysophosphatidylethanolamine (C18:2) | 0.91 | down |
| Sphingomyelin (d17:1,C16:0) | 0.91 | up |
| CA19-9 | 0.91 | up |

TABLE 13

Panel Number 19, Algorithm RF, Matrix Serum and plasma, CA19-9 excluded, with ANOVA correction of data

| Metabolite | AUC estimate | direction from ANOVA |
| --- | --- | --- |
| Sphingomyelin (d18:1, C19:0) | 0.81 | up |
| Sphingomyelin (d18:2, C22:1) | 0.81 | up |
| Coenzyme Q9 | 0.81 | down |
| O-Acetylcarnitine | 0.81 | down |
| Hexanoylcarnitine | 0.81 | up |
| Palmitoleic acid (C16:cis[9]1) | 0.81 | down |
| Histidine | 0.81 | down |
| Uric acid | 0.81 | down |
| TAG (C16:0, C18:1, C18:3) | 0.81 | up |
| Lysophosphatidylethanolamine (C18:2) | 0.81 | down |

TABLE 14

Panel Number 20, Algorithm RF, Matrix Serum and plasma, CA19-9 excluded, no ANOVA correction of data

| Metabolite | AUC estimate | direction from ANOVA |
| --- | --- | --- |
| Sphingomyelin (d18:1, C19:0) | 0.83 | up |
| Coenzyme Q10 | 0.83 | down |
| Uridine | 0.83 | down |
| Trimethylamine-N-oxide (TMAO) | 0.83 | down |
| Docosahexaenoic acid (C22:cis[4,7,10,13,16,19]6) | 0.83 | up |
| Palmitoleic acid (C16:cis[9]1) | 0.83 | down |
| Threonine | 0.83 | down |
| Uric acid | 0.83 | down |
| Lysophosphatidylethanolamine (C18:2) | 0.83 | down |

TABLE 15

Panel Number 22, Algorithm RF, Matrix Serum and plasma, CA19-9 categorical included, no ANOVA correction of data

| Metabolite | AUC estimate | direction from ANOVA |
| --- | --- | --- |
| Sphingomyelin (d18:2, C19:0) | 0.91 | up |
| Sorbitol | 0.91 | down |
| Coenzyme Q9 | 0.91 | down |
| Uridine | 0.91 | down |
| Proline | 0.91 | down |
| Uric acid | 0.91 | down |
| Phosphatidylcholine (C18:0, C22:6) | 0.91 | up |
| Lysophosphatidylethanolamine (C18:2) | 0.91 | down |
| CA19-9 | 0.91 | up |

TABLE 16

Additional Biomarkers for Panel Composition gamma-Tocopherol
Coenzyme Q10
Sorbitol
Aspartate
Citrulline
Coenzyme Q9
Pregnenolone sulfate
Creatinine
Creatine
Glycocholic acid
Trimethylamine-N-oxide (TMAO)
Pipecolic acid
Proline betaine
O-Acetylcarnitine
Carnosine
Propionylcarnitine
Hexanoylcarnitine
Eicosapentaenoic acid (C20:cis[5,8,11,14,17]5)
Docosahexaenoic acid (C22:cis[4,7,10,13,16,19]6)
Palmitoleic acid (C16:cis[9]1)
Lignoceric acid (C24:0)
1-Hydroxy-2-amino-(cis,trans)-3,5-octadecadiene (from sphingolipids)
Pyruvate
Threonine
Mannose
alpha-Ketoglutarate
Serine
Proline
3-Hydroxybutyrate
1,5-Anhydrosorbitol
Histidine
Ketoleucine
2-Hydroxybutyrate
Isocitrate
Dehydroepiandrosterone sulfate
TAG (C18:2, C18:2)

TABLE 16-continued

Additional Biomarkers for Panel Composition

TAG (C16:0, C18:1, C18:3)
Sphingosine-1-phosphate (d18:1)
Kynurenine
Tryptophan

TABLE 17

Panel Number 1, Algorithm ANOVA, Matrix Serum and plasma, CA19-9 excluded, with ANOVA correction of data

| Metabolite | AUC estimate | direction from ANOVA |
|---|---|---|
| Sphingomyelin (d18:1, C20:1) | 0.68 | up |
| Sphingomyelin (d18:1, C22:1) | 0.67 | up |
| Sphingomyelin (d18:1, C23:1) | 0.71 | up |
| Sphingomyelin (d18:1, C24:2) | 0.66 | up |
| Citrulline | 0.63 | down |
| Coenzyme Q9 | 0.62 | down |
| Mannose | 0.63 | up |
| Proline | 0.66 | down |
| Histidine | 0.66 | down |
| Uric acid | 0.67 | down |

TABLE 18

Panel Number 2, Algorithm ANOVA, Matrix Serum and plasma, CA19-9 excluded, with ANOVA correction of data

| Metabolite | AUC estimate | direction from ANOVA |
|---|---|---|
| Sphingomyelin (d18:1, C18:0) | 0.80 (Plasma, excl. CA19-9) | up |
| Sphingomyelin (d18:1, C18:1) | 0.80 (Plasma, excl. CA19-9) | up |
| Sphingomyelin (d18:1, C20:1) | 0.80 (Plasma, excl. CA19-9) | up |
| Sphingomyelin (d18:1, C22:1) | 0.80 (Plasma, excl. CA19-9) | up |
| Sphingomyelin (d18:1, C23:1) | 0.80 (Plasma, excl. CA19-9) | up |
| Sphingomyelin (d18:1, C24:2) | 0.80 (Plasma, excl. CA19-9) | up |
| Ceramide (d18:1, C18:0) | 0.80 (Plasma, excl. CA19-9) | up |
| Ceramide (d17:1, 016:0) | 0.80 (Plasma, excl. CA19-9) | up |
| Coenzyme Q9 | 0.80 (Plasma, excl. CA19-9) | down |
| Proline | 0.80 (Plasma, excl. CA19-9) | down |

TABLE 19

Panel Number 4, Algorithm ROC, Matrix Plasma, CA19-9 excluded, no ANOVA correction of data

| Metabolite | AUC estimate | direction from ANOVA |
|---|---|---|
| Sphingomyelin (d18:1, C19:0) | 0.7819 | up |
| Sphingomyelin (d18:2, C19:0) | 0.7862 | up |
| Sphingomyelin (d18:2, C20:1) | 0.7537 | up |
| Sphingomyelin (d17:1, C16:0) | 0.7325 | up |
| Sphingomyelin (d17:1, C18:0) | 0.8133 | up |
| Sphingomyelin (d17:1, C20:0) | 0.7545 | up |
| 2-Hydroxybutyrate | 0.7065 | up |
| Phosphatidylcholine (C18:0, C22:6) | 0.7769 | up |
| Sphingomyelin (d17:1, C16:0) | 0.7652 | up |
| Sphingomyelin (d18:2, C17:0) | 0.7657 | up |

TABLE 20

Panel Number 5, Algorithm ROC, Matrix Serum, CA19-9 excluded, no ANOVA correction of data

| Metabolite | AUC estimate | direction from ANOVA |
|---|---|---|
| Sphingomyelin (d18:1, C19:0) | 0.781 | up |
| Sphingomyelin (d18:2, C19:0) | 0.7577 | up |
| Sphingomyelin (d18:2, C21:0) | 0.7217 | up |
| Sphingomyelin (d17:1, C18:0) | 0.7406 | up |
| Sphingomyelin (d17:1, C20:0) | 0.7478 | up |
| Sphingomyelin (d17:1, C24:1) | 0.7427 | up |
| Ceramide (d17:1, C16:0) | 0.7469 | up |
| Coenzyme Q10 | 0.7397 | down |
| Uric acid | 0.7133 | down |
| Sphingomyelin (d17:1, C18:0) | 0.7023 | up |

TABLE 21

Panel Number 10, Algorithm RF, Matrix Serum, CA19-9 excluded, with ANOVA correction of data

| Metabolite | AUC estimate | direction from ANOVA |
|---|---|---|
| Sphingomyelin (d18:1, C19:0) | 0.75 | up |
| Sphingomyelin (d18:2, C24:2) | 0.75 | up |
| Coenzyme Q10 | 0.75 | down |
| Coenzyme Q9 | 0.75 | down |
| Uridine | 0.75 | down |
| Carnosine | 0.75 | down |
| Sphinganine-1-phosphate (d18:0) | 0.75 | down |
| 3-Hydroxybutyrate | 0.75 | down |
| Histidine | 0.75 | down |

TABLE 22

Panel Number 11, Algorithm RF, Matrix Serum, CA19-9 numerical included, with ANOVA correction of data

| Metabolite | AUC estimate | direction from ANOVA |
|---|---|---|
| Sphingomyelin (d18:2, C22:1) | 0.91 | up |
| Proline betaine | 0.91 | up |
| O-Acetylcarnitine | 0.91 | down |
| Sphinganine-1-phosphate (d18:0) | 0.91 | down |
| Uric acid | 0.91 | down |
| TAG (C18:2, C18:2) | 0.91 | up |
| Phosphatidylcholine (C16:0, C20:5) | 0.91 | down |
| CA19-9 | 0.91 | up |

TABLE 23

Panel Number 13, Algorithm RF, Matrix Plasma, CA19-9 categorical included, no ANOVA correction of data

| Metabolite | AUC estimate | direction from ANOVA |
|---|---|---|
| Sphingomyelin (d17:1, C18:0) | 0.96 | up |
| Ceramide (d18:1, C24:0) | 0.96 | down |
| Sphinganine-1-phosphate (d18:0) | 0.96 | down |
| Pyruvate | 0.96 | down |
| Proline | 0.96 | down |
| Histidine | 0.96 | down |
| Isocitrate | 0.96 | up |
| Phosphatidylcholine (C18:0, C22:6) | 0.96 | up |
| Sphingomyelin (d18:2, C17:0) | 0.96 | up |
| CA19-9 | 0.96 | up |

TABLE 24

Panel Number 21, Algorithm RF, Matrix Serum and Plasma, CA19-9 categorical included, with ANOVA correction of data

| Metabolite | AUC estimate | direction from ANOVA |
|---|---|---|
| Sphingomyelin (d18:1, C19:0) | 0.88 | up |
| Sphingomyelin (d18:2, C22:1) | 0.88 | up |
| Coenzyme Q9 | 0.88 | down |
| Creatine | 0.88 | down |
| O-Acetylcarnitine | 0.88 | down |
| Hexanoylcarnitine | 0.88 | up |
| Proline | 0.88 | down |
| Uric acid | 0.88 | down |
| TAG (C18:2, C18:2) | 0.88 | up |
| CA19-9 | 0.88 | up |

TABLE 25

Panel Number 23, Algorithm ANOVA, Matrix Serum and Plasma, CA19-9 excluded, with ANOVA correction of data

| Metabolite | AUC estimate | direction from ANOVA |
|---|---|---|
| Sphingomyelin (d18:1, C18:0) | 0.76 | up |
| Sphingomyelin (d18:1, C18:1) | 0.76 | up |
| Sphingomyelin (d18:1, C20:1) | 0.76 | up |
| Sphingomyelin (d18:1, C22:1) | 0.76 | up |
| Sphingomyelin (d18:1, C23:1) | 0.76 | up |
| Lysophosphatidylethanolamine (C18:2) | 0.76 | down |
| Coenzyme Q9 | 0.76 | down |
| Ceramide (d17:1, C16:0) | 0.76 | up |
| Ceramide (d18:1, C18:0) | 0.76 | up |
| Prolin | 0.76 | down |

TABLE 26

Panel Number 24, Algorithm elastic net, Matrix Plasma, CA19-9 included, no ANOVA Correction of data

| Metabolite | AUC estimate | direction from ANOVA |
|---|---|---|
| CA19-9 | 0.93 | up |
| Sphingomyelin (d17:1, C18:0) | 0.93 | up |
| Phosphatidylcholine (C18:0, C22:6) | 0.93 | up |
| Proline | 0.93 | down |
| Sphingosine-1-phosphate (d18:1) | 0.93 | down |
| alpha-Ketoglutarate | 0.93 | up |
| Palmitoleic acid (C16:cis[9]1) | 0.93 | down |
| Kynurenine | 0.93 | up |
| Tryptophan | 0.93 | down |
| Serine | 0.93 | down |

TABLE 27

ANOVA Data for all Metabolites listed in any of Tables 1 to 26 for all matrices

| Matrix | Metabolite | Direction | ANOVA result of pancreatic cancer relative to pancreatitis Ratio | p-value | t-value |
|---|---|---|---|---|---|
| Plasma | 1,5-Anhydrosorbitol | down | 0.70 | 0.112184 | −1.60 |
| Plasma | 1-Hydroxy-2-amino-(cis,trans)-3,5-octadecadiene (from sphingolipids) | up | 1.42 | 0.001078 | 3.33 |
| Plasma | 2-Hydroxybutyrate | up | 1.37 | 0.02006 | 2.35 |
| Plasma | 3-Hydroxybutyrate | up | 1.56 | 0.162013 | 1.41 |
| Plasma | alpha-Ketoglutarate | up | 1.82 | 2.83E−05 | 4.32 |
| Plasma | Aspartate | down | 0.98 | 0.803054 | −0.25 |
| Plasma | CA19-9 | up | 18.36 | 6.89E−09 | 6.18 |
| Plasma | Carnosine | down | 0.61 | 0.140206 | −1.49 |
| Plasma | Ceramide (d17:1, C16:0) | up | 1.33 | 0.00966 | 2.62 |
| Plasma | Ceramide (d18:1, C18:0) | up | 1.44 | 0.010846 | 2.58 |
| Plasma | Ceramide (d18:1, C24:0) | down | 0.79 | 0.001509 | −3.23 |
| Plasma | Citrulline | down | 0.76 | 0.000856 | −3.40 |
| Plasma | Coenzyme Q10 | down | 0.85 | 0.165097 | −1.39 |
| Plasma | Coenzyme Q9 | down | 0.58 | 0.003463 | −2.97 |
| Plasma | Creatine | down | 0.75 | 0.004049 | −2.92 |
| Plasma | Creatinine | up | 1.03 | 0.63821 | 0.47 |
| Plasma | Cryptoxanthin | down | 0.87 | 0.553268 | −0.59 |
| Plasma | Dehydroepiandrosterone sulfate | down | 0.77 | 0.221202 | −1.23 |
| Plasma | Docosahexaenoic acid (C22:cis[4,7,10,13,16,19]6) | up | 1.47 | 0.000276 | 3.72 |
| Plasma | Eicosapentaenoic acid (C20:cis[5,8,11,14,17]5) | down | 0.68 | 0.006485 | −2.76 |
| Plasma | gamma-Tocopherol | down | 0.68 | 0.004717 | −2.87 |
| Plasma | Glycocholic acid | up | 6.15 | 0.000353 | 3.66 |
| Plasma | Hexanoylcarnitine | up | 1.14 | 0.295431 | 1.05 |
| Plasma | Histidine | down | 0.77 | 0.000324 | −3.68 |
| Plasma | Isocitrate | up | 1.26 | 0.008074 | 2.68 |
| Plasma | Ketoleucine | down | 0.83 | 0.146653 | −1.46 |
| Plasma | Lignoceric acid (C24:0) | down | 0.93 | 0.420195 | −0.81 |
| Plasma | Lysophosphatidylethanolamine (C18:2) | down | 0.61 | 1.44E−06 | −5.02 |
| Plasma | Mannose | up | 1.33 | 0.023498 | 2.29 |
| Plasma | O-Acetylcarnitine | up | 1.07 | 0.547685 | 0.60 |

TABLE 27-continued

ANOVA Data for all Metabolites listed in any of Tables 1 to 26 for all matrices

| Matrix | Metabolite | Direction | ANOVA result of pancreatic cancer relative to pancreatitis | | |
|---|---|---|---|---|---|
| | | | Ratio | p-value | t-value |
| Plasma | Palmitoleic acid (C16:cis[9]1) | down | 0.85 | 0.288324 | −1.07 |
| Plasma | Phosphatidylcholine (C16:0, C20:5) | down | 0.90 | 0.032376 | −2.16 |
| Plasma | Phosphatidylcholine (C18:0, C22:6) | up | 1.26 | 8.59E−05 | 4.04 |
| Plasma | Pipecolic acid | down | 0.74 | 0.001085 | −3.33 |
| Plasma | Pregnenolone sulfate | down | 0.84 | 0.204908 | −1.27 |
| Plasma | Proline | down | 0.69 | 2.24E−05 | −4.38 |
| Plasma | Proline betaine | down | 0.87 | 0.585038 | −0.55 |
| Plasma | Propionylcarnitine | down | 0.69 | 0.00053 | −3.54 |
| Plasma | Pyruvate | down | 0.93 | 0.367408 | −0.90 |
| Plasma | Serine | down | 0.96 | 0.4496 | −0.76 |
| Plasma | Sorbitol | down | 0.55 | 0.000401 | −3.63 |
| Plasma | Sphinganine-1-phosphate (d18:0) | down | 0.79 | 0.025867 | −2.25 |
| Plasma | Sphingomyelin (d17:1, C16:0) | up | 1.39 | 0.002201 | 3.11 |
| Plasma | Sphingomyelin (d17:1, C16:0) | up | 1.20 | 0.004553 | 2.88 |
| Plasma | Sphingomyelin (d17:1, C16:0) | up | 1.28 | 0.000338 | 3.67 |
| Plasma | Sphingomyelin (d17:1, C18:0) | up | 1.36 | 4.86E−05 | 4.18 |
| Plasma | Sphingomyelin (d17:1, C18:0) | up | 1.21 | 0.001593 | 3.22 |
| Plasma | Sphingomyelin (d17:1, C20:0) | up | 1.34 | 0.001219 | 3.30 |
| Plasma | Sphingomyelin (d17:1, C24:1) | up | 1.59 | 4.28E−05 | 4.21 |
| Plasma | Sphingomyelin (d18:1, C18:0) | up | 1.29 | 0.00202 | 3.14 |
| Plasma | Sphingomyelin (d18:1, C18:1) | up | 1.39 | 0.00092 | 3.38 |
| Plasma | Sphingomyelin (d18:1, C19:0) | up | 1.44 | 7.72E−05 | 4.06 |
| Plasma | Sphingomyelin (d18:1, C20:1) | up | 1.62 | 0.000148 | 3.89 |
| Plasma | Sphingomyelin (d18:1, C22:1) | up | 1.77 | 5.47E−05 | 4.15 |
| Plasma | Sphingomyelin (d18:1, C23:1) | up | 1.67 | 4.69E−05 | 4.19 |
| Plasma | Sphingomyelin (d18:1, C24:1) | up | 1.19 | 0.017318 | 2.41 |
| Plasma | Sphingomyelin (d18:1, C24:2) | up | 1.58 | 0.000702 | 3.46 |
| Plasma | Sphingomyelin (d18:2, C17:0) | up | 1.15 | 0.005612 | 2.81 |
| Plasma | Sphingomyelin (d18:2, C19:0) | up | 1.37 | 0.000937 | 3.37 |
| Plasma | Sphingomyelin (d18:2, C20:1) | up | 1.39 | 0.000229 | 3.78 |
| Plasma | Sphingomyelin (d18:2, C21:0) | up | 1.29 | 0.007497 | 2.71 |
| Plasma | Sphingomyelin (d18:2, C22:1) | up | 1.62 | 3.12E−06 | 4.84 |
| Plasma | Sphingomyelin (d18:2, C24:2) | up | 1.33 | 0.001829 | 3.17 |
| Plasma | TAG (C16:0, C18:1, C18:3) | up | 1.12 | 0.254012 | 1.14 |
| Plasma | TAG (C18:2, C18:2) | up | 1.03 | 0.787305 | 0.27 |
| Plasma | Threonine | down | 0.88 | 0.105825 | −1.63 |
| Plasma | Trimethylamine-N-oxide (TMAO) | up | 1.45 | 0.211712 | 1.25 |
| Plasma | Uric acid | down | 0.81 | 0.039553 | −2.08 |
| Plasma | Uridine | down | 0.93 | 0.36906 | −0.90 |
| Serum | 1,5-Anhydrosorbitol | down | 0.72 | 0.129242 | −1.53 |
| Serum | 1-Hydroxy-2-amino-(cis,trans)-3,5-octadecadiene (from sphingolipids) | up | 1.24 | 0.086788 | 1.72 |
| Serum | 2-Hydroxybutyrate | down | 0.97 | 0.849631 | −0.19 |
| Serum | 3-Hydroxybutyrate | down | 0.54 | 0.085235 | −1.73 |
| Serum | alpha-Ketoglutarate | down | 0.86 | 0.577279 | −0.56 |
| Serum | Aspartate | down | 0.78 | 0.081011 | −1.76 |
| Serum | CA19-9 | up | 8.33 | 9.03E−05 | 4.02 |
| Serum | Carnosine | down | 0.67 | 0.054001 | −1.94 |
| Serum | Ceramide (d17:1, C16:0) | up | 1.39 | 0.00898 | 2.65 |
| Serum | Ceramide (d18:1, C18:0) | up | 1.42 | 0.018761 | 2.38 |
| Serum | Ceramide (d18:1, C24:0) | down | 0.93 | 0.306255 | −1.03 |
| Serum | Citrulline | down | 0.67 | 0.000306 | −3.73 |
| Serum | Coenzyme Q10 | down | 0.64 | 0.001002 | −3.35 |
| Serum | Coenzyme Q9 | down | 0.64 | 0.0233 | −2.29 |
| Serum | Creatine | up | 1.01 | 0.947844 | 0.07 |
| Serum | Creatinine | down | 0.85 | 0.118716 | −1.57 |
| Serum | Cryptoxanthin | up | 1.50 | 0.086784 | 1.72 |
| Serum | Dehydroepiandrosterone sulfate | down | 0.75 | 0.173751 | −1.37 |
| Serum | Docosahexaenoic acid (C22:cis[4,7,10,13,16,19]6) | up | 1.02 | 0.878814 | 0.15 |
| Serum | Eicosapentaenoic acid (C20:cis[5,8,11,14,17]5) | down | 0.73 | 0.048572 | −1.99 |
| Serum | gamma-Tocopherol | down | 0.89 | 0.459956 | −0.74 |
| Serum | Glycocholic acid | up | 1.37 | 0.455023 | 0.75 |
| Serum | Histidine | down | 0.72 | 0.006032 | −2.78 |
| Serum | Isocitrate | down | 0.86 | 0.075543 | −1.79 |
| Serum | Ketoleucine | down | 0.93 | 0.558542 | −0.59 |
| Serum | Lignoceric acid (C24:0) | down | 0.90 | 0.286922 | −1.07 |

TABLE 27-continued

ANOVA Data for all Metabolites listed in any of Tables 1 to 26 for all matrices

| Matrix | Metabolite | Direction | ANOVA result of pancreatic cancer relative to pancreatitis | | |
|---|---|---|---|---|---|
| | | | Ratio | p-value | t-value |
| Serum | Lysophosphatidylethanolamine (C18:2) | down | 0.83 | 0.097566 | −1.67 |
| Serum | Mannose | up | 1.75 | 0.028419 | 2.21 |
| Serum | O-Acetylcarnitine | down | 0.64 | 0.001349 | −3.27 |
| Serum | Palmitoleic acid (C16:cis[9]1) | down | 0.68 | 0.019995 | −2.35 |
| Serum | Phosphatidylcholine (C16:0, C20:5) | down | 0.85 | 0.055291 | −1.93 |
| Serum | Phosphatidylcholine (C18:0, C22:6) | up | 1.05 | 0.513731 | 0.65 |
| Serum | Pipecolic acid | up | 1.07 | 0.521609 | 0.64 |
| Serum | Pregnenolone sulfate | down | 0.69 | 0.031915 | −2.17 |
| Serum | Proline | down | 0.75 | 0.004589 | −2.88 |
| Serum | Proline betaine | up | 1.16 | 0.556731 | 0.59 |
| Serum | Pyruvate | down | 0.76 | 0.266689 | −1.11 |
| Serum | Serine | down | 0.86 | 0.081561 | −1.75 |
| Serum | Sorbitol | up | 1.16 | 0.519633 | 0.65 |
| Serum | Sphinganine-1-phosphate (d18:0) | down | 0.74 | 0.031159 | −2.18 |
| Serum | Sphingomyelin (d17:1, C16:0) | up | 1.25 | 0.053968 | 1.94 |
| Serum | Sphingomyelin (d17:1, C16:0) | up | 1.16 | 0.143493 | 1.48 |
| Serum | Sphingomyelin (d17:1, C16:0) | up | 1.14 | 0.301942 | 1.04 |
| Serum | Sphingomyelin (d17:1, C18:0) | up | 1.33 | 0.008979 | 2.65 |
| Serum | Sphingomyelin (d17:1, C18:0) | up | 1.79 | 0.126103 | 1.54 |
| Serum | Sphingomyelin (d17:1, C20:0) | up | 1.36 | 0.00399 | 2.92 |
| Serum | Sphingomyelin (d17:1, C24:1) | up | 1.18 | 0.043725 | 2.03 |
| Serum | Sphingomyelin (d18:1, C18:0) | up | 1.28 | 0.047624 | 2.00 |
| Serum | Sphingomyelin (d18:1, C18:1) | up | 1.33 | 0.012649 | 2.52 |
| Serum | Sphingomyelin (d18:1, C19:0) | up | 1.33 | 0.000409 | 3.61 |
| Serum | Sphingomyelin (d18:1, C20:1) | up | 1.25 | 0.021854 | 2.32 |
| Serum | Sphingomyelin (d18:1, C22:1) | up | 1.31 | 0.020283 | 2.35 |
| Serum | Sphingomyelin (d18:1, C23:1) | up | 1.18 | 0.048637 | 1.99 |
| Serum | Sphingomyelin (d18:1, C24:1) | up | 1.07 | 0.305724 | 1.03 |
| Serum | Sphingomyelin (d18:1, C24:2) | up | 1.27 | 0.036538 | 2.11 |
| Serum | Sphingomyelin (d18:2, C17:0) | up | 1.07 | 0.54147 | 0.61 |
| Serum | Sphingomyelin (d18:2, C19:0) | up | 1.45 | 0.000637 | 3.49 |
| Serum | Sphingomyelin (d18:2, C20:1) | up | 1.38 | 0.002494 | 3.08 |
| Serum | Sphingomyelin (d18:2, C21:0) | up | 1.34 | 0.00694 | 2.74 |
| Serum | Sphingomyelin (d18:2, C22:1) | up | 1.32 | 0.001103 | 3.33 |
| Serum | Sphingomyelin (d18:2, C24:2) | up | 1.22 | 0.004057 | 2.92 |
| Serum | TAG (C16:0, C18:1, C18:3) | up | 1.52 | 0.003144 | 3.00 |
| Serum | TAG (C18:2, C18:2) | up | 1.49 | 0.00169 | 3.20 |
| Serum | Threonine | down | 0.81 | 0.026945 | −2.23 |
| Serum | Trimethylamine-N-oxide (TMAO) | down | 0.68 | 0.255352 | −1.14 |
| Serum | Uric acid | down | 0.66 | 0.001044 | −3.34 |
| Serum | Uridine | down | 0.79 | 0.025021 | −2.26 |
| Serum + Plasma | 1,5-Anhydrosorbitol | down | 0.68 | 0.010301 | −2.58 |
| Serum + Plasma | 1-Hydroxy-2-amino-(cis,trans)-3,5-octadecadiene (from sphingolipids) | up | 1.28 | 0.002321 | 3.07 |
| Serum + Plasma | 2-Hydroxybutyrate | up | 1.10 | 0.372449 | 0.89 |
| Serum + Plasma | 3-Hydroxybutyrate | down | 0.78 | 0.289097 | −1.06 |
| Serum + Plasma | alpha-Ketoglutarate | up | 1.19 | 0.245593 | 1.16 |
| Serum + Plasma | Aspartate | down | 0.85 | 0.046851 | −2.00 |
| Serum + Plasma | CA19-9 | up | 11.88 | 3.93E−12 | 7.24 |
| Serum + Plasma | Carnosine | down | 0.68 | 0.020215 | −2.34 |
| Serum + Plasma | Ceramide (d17:1, C16:0) | up | 1.34 | 0.000362 | 3.61 |
| Serum + Plasma | Ceramide (d18:1, C18:0) | up | 1.43 | 0.000256 | 3.70 |
| Serum + Plasma | Ceramide (d18:1, C24:0) | down | 0.89 | 0.020191 | −2.34 |
| Serum + Plasma | Citrulline | down | 0.71 | 1.55E−07 | −5.39 |
| Serum + Plasma | Coenzyme Q10 | down | 0.75 | 0.000589 | −3.47 |
| Serum + Plasma | Coenzyme Q9 | down | 0.62 | 0.000287 | −3.67 |
| Serum + Plasma | Creatine | down | 0.88 | 0.107085 | −1.62 |
| Serum + Plasma | Creatinine | down | 0.93 | 0.240945 | −1.17 |
| Serum + Plasma | Cryptoxanthin | up | 1.18 | 0.309544 | 1.02 |
| Serum + Plasma | Dehydroepiandrosterone sulfate | down | 0.74 | 0.042037 | −2.04 |
| Serum + Plasma | Docosahexaenoic acid (C22:cis[4,7,10,13,16,19]6) | up | 1.19 | 0.035833 | 2.11 |
| Serum + Plasma | Eicosapentaenoic acid (C20:cis[5,8,11,14,17]5) | down | 0.68 | 0.000267 | −3.69 |
| Serum + Plasma | gamma-Tocopherol | down | 0.81 | 0.033443 | −2.14 |
| Serum + Plasma | Glycocholic acid | up | 2.46 | 0.004039 | 2.90 |
| Serum + Plasma | Histidine | down | 0.73 | 5.28E−06 | −4.63 |
| Serum + Plasma | Isocitrate | up | 1.00 | 0.958958 | 0.05 |

TABLE 27-continued

ANOVA Data for all Metabolites listed in any of Tables 1 to 26 for all matrices

| Matrix | Metabolite | Direction | ANOVA result of pancreatic cancer relative to pancreatitis | | |
|---|---|---|---|---|---|
| | | | Ratio | p-value | t-value |
| Serum + Plasma | Ketoleucine | down | 0.89 | 0.198701 | −1.29 |
| Serum + Plasma | Lignoceric acid (C24:0) | down | 0.91 | 0.151 | −1.44 |
| Serum + Plasma | Lysophosphatidylethanolamine (C18:2) | down | 0.71 | 2.15E−06 | −4.85 |
| Serum + Plasma | Mannose | up | 1.51 | 0.003417 | 2.95 |
| Serum + Plasma | O-Acetylcarnitine | down | 0.78 | 0.005213 | −2.81 |
| Serum + Plasma | Palmitoleic acid (C16:cis[9]1) | down | 0.75 | 0.007319 | −2.70 |
| Serum + Plasma | Phosphatidylcholine (C16:0, C20:5) | down | 0.86 | 0.001625 | −3.18 |
| Serum + Plasma | Phosphatidylcholine (C18:0, C22:6) | up | 1.14 | 0.004201 | 2.88 |
| Serum + Plasma | Pipecolic acid | down | 0.90 | 0.113584 | −1.59 |
| Serum + Plasma | Pregnenolone sulfate | down | 0.78 | 0.01873 | −2.36 |
| Serum + Plasma | Proline | down | 0.73 | 1.61E−06 | −4.89 |
| Serum + Plasma | Proline betaine | down | 0.97 | 0.8797 | −0.15 |
| Serum + Plasma | Pyruvate | down | 0.84 | 0.199114 | −1.29 |
| Serum + Plasma | Serine | down | 0.89 | 0.019434 | −2.35 |
| Serum + Plasma | Sorbitol | down | 0.84 | 0.192819 | −1.31 |
| Serum + Plasma | Sphinganine-1-phosphate (d18:0) | down | 0.78 | 0.004251 | −2.88 |
| Serum + Plasma | Sphingomyelin (d17:1, C16:0) | up | 1.27 | 0.002065 | 3.11 |
| Serum + Plasma | Sphingomyelin (d17:1, C16:0) | up | 1.14 | 0.012593 | 2.51 |
| Serum + Plasma | Sphingomyelin (d17:1, C16:0) | up | 1.19 | 0.006193 | 2.76 |
| Serum + Plasma | Sphingomyelin (d17:1, C18:0) | up | 1.32 | 2.4E−05 | 4.29 |
| Serum + Plasma | Sphingomyelin (d17:1, C18:0) | up | 1.47 | 0.013879 | 2.48 |
| Serum + Plasma | Sphingomyelin (d17:1, C20:0) | up | 1.34 | 1.64E−05 | 4.38 |
| Serum + Plasma | Sphingomyelin (d17:1, C24:1) | up | 1.31 | 4E−05 | 4.17 |
| Serum + Plasma | Sphingomyelin (d18:1, C18:0) | up | 1.27 | 0.001083 | 3.30 |
| Serum + Plasma | Sphingomyelin (d18:1, C18:1) | up | 1.31 | 0.000203 | 3.76 |
| Serum + Plasma | Sphingomyelin (d18:1, C19:0) | up | 1.37 | 7.78E−08 | 5.50 |
| Serum + Plasma | Sphingomyelin (d18:1, C20:1) | up | 1.37 | 3.12E−05 | 4.23 |
| Serum + Plasma | Sphingomyelin (d18:1, C22:1) | up | 1.45 | 2.18E−05 | 4.31 |
| Serum + Plasma | Sphingomyelin (d18:1, C23:1) | up | 1.34 | 3.21E−05 | 4.22 |
| Serum + Plasma | Sphingomyelin (d18:1, C24:1) | up | 1.11 | 0.026027 | 2.24 |
| Serum + Plasma | Sphingomyelin (d18:1, C24:2) | up | 1.38 | 0.00011 | 3.92 |
| Serum + Plasma | Sphingomyelin (d18:2, C17:0) | up | 1.11 | 0.046649 | 2.00 |
| Serum + Plasma | Sphingomyelin (d18:2, C19:0) | up | 1.38 | 3.21E−06 | 4.74 |
| Serum + Plasma | Sphingomyelin (d18:2, C20:1) | up | 1.33 | 1.91E−05 | 4.34 |
| Serum + Plasma | Sphingomyelin (d18:2, C21:0) | up | 1.30 | 0.000168 | 3.81 |
| Serum + Plasma | Sphingomyelin (d18:2, C22:1) | up | 1.41 | 7.54E−08 | 5.51 |
| Serum + Plasma | Sphingomyelin (d18:2, C24:2) | up | 1.27 | 9.47E−06 | 4.50 |
| Serum + Plasma | TAG (C16:0, C18:1, C18:3) | up | 1.36 | 0.000333 | 3.63 |
| Serum + Plasma | TAG (C18:2, C18:2) | up | 1.31 | 0.000433 | 3.56 |
| Serum + Plasma | Threonine | down | 0.83 | 0.001967 | −3.12 |
| Serum + Plasma | Trimethylamine-N-oxide (TMAO) | down | 0.97 | 0.878188 | −0.15 |
| Serum + Plasma | Uric acid | down | 0.73 | 3.87E−05 | −4.18 |
| Serum + Plasma | Uridine | down | 0.86 | 0.029178 | −2.19 |
| Serum | Kynurenine | down | 0.96 | 0.711959 | −0.37 |
| Plasma | Kynurenine | up | 1.16 | 0.115984 | 1.58 |
| Serum + Plasma | Kynurenine | up | 1.08 | 0.308068 | 1.02 |
| Serum | Sphingosine-1-phosphate (d18:1) | down | 0.87 | 0.318297 | −1.00 |
| Plasma | Sphingosine-1-phosphate (d18:1) | down | 0.93 | 0.325758 | −0.99 |
| Serum + Plasma | Sphingosine-1-phosphate (d18:1) | down | 0.91 | 0.236226 | −1.19 |
| Serum | Tryptophan | down | 0.88 | 0.266443 | −1.12 |
| Plasma | Tryptophan | down | 0.86 | 0.129383 | −1.52 |
| Serum + Plasma | Tryptophan | down | 0.87 | 0.059412 | −1.89 |

TABLE 28

Single metabolite biomarkers for diagnosing pancreatic cancer

| Matrix | Metabolite | Direction | ANOVA result of pancreatic cancer relative to pancreatitis | | |
|---|---|---|---|---|---|
| | | | Ratio | p-value | t-value |
| Serum | Lysophosphatidyl-ethanolamine (C18:2) | down | 0.83 | 0.0975655 | -1.67 |
| Serum | Sphingomyelin (d17:1, C18:0) | up | 1.79 | 0.1261030 | 1.54 |
| Serum | Sphingomyelin (d17:1, C16:0) | up | 1.16 | 0.1434933 | 1.48 |
| Plasma | Lysophosphatidyl-ethanolamine (C18:2) | down | 0.61 | 0.0000014 | -5.02 |
| Plasma | Sphingomyelin (d17:1, C16:0) | up | 1.28 | 0.0003381 | 3.67 |
| Plasma | Sphingomyelin (d17:1, C18:0) | up | 1.21 | 0.0015925 | 3.22 |
| Plasma | Sphingomyelin (d17:1, C16:0) | up | 1.20 | 0.0045531 | 2.88 |
| Plasma | Sphingomyelin (d18:2, C17:0) | up | 1.15 | 0.0056123 | 2.81 |
| Plasma | Sphingomyelin (d18:2, C24:0) | up | 1.19 | 0.0173175 | 2.41 |
| Plasma | Cholesterolester, total | down | 0.99 | 0.0866887 | -1.72 |
| Plasma | Lysophosphatidyl-choline (C18:0) | down | 0.87 | 0.0957764 | -1.68 |
| Serum + Plasma | Lysophosphatidyl-ethanolamine (C18:2) | down | 0.71 | 0.0000021 | -4.85 |
| Serum + Plasma | Sphingomyelin (d17:1, C16:0) | up | 1.19 | 0.0061928 | 2.76 |
| Serum + Plasma | Sphingomyelin (d17:1, C16:0) | up | 1.14 | 0.0125930 | 2.51 |
| Serum + Plasma | Sphingomyelin (d17:1, C18:0) | up | 1.47 | 0.0138791 | 2.48 |
| Serum + Plasma | Sphingomyelin (d18:2, C24:0) | up | 1.11 | 0.0260273 | 2.24 |
| Serum + Plasma | Lysophosphatidyl-choline (C18:0) | down | 0.90 | 0.0375720 | -2.09 |
| Serum + Plasma | Sphingomyelin (d18:2, C17:0) | up | 1.11 | 0.0466493 | 2.00 |
| Serum + Plasma | TAG (C18:1, C18:2, C18:3) | up | 1.14 | 0.1343839 | 1.50 |

TABLE 29

List of identified biomarkers in serum for pancreatic cancer relative to pancreatitis

| Metabolite | Direction | ANOVA result of pancreatic cancer relative to pancreatitis in serum | | |
|---|---|---|---|---|
| | | Estimated fold change | p-value | t-value |
| Citrulline | down | 0.6659 | 0.000306024 | -3.72978 |
| Sphingomyelin (d18:1, C19:0) | up | 1.3323 | 0.000408675 | 3.61444 |
| Sphingomyelin (d18:2, C19:0) | up | 1.4549 | 0.000637255 | 3.487735 |
| Coenzyme Q10 | down | 0.644 | 0.001001669 | -3.35476 |
| Uric acid | down | 0.6634 | 0.001043796 | -3.3425 |
| Sphingomyelin (d18:2, C22:1) | up | 1.3202 | 0.001102996 | 3.326448 |
| O-Acetylcarnitine | down | 0.64 | 0.001348925 | -3.26542 |
| Cholesterylester C16:1 | down | 0.6485 | 0.001532724 | -3.22691 |
| Sphingomyelin (d18:2, C18:1) | up | 1.4172 | 0.001651561 | 3.203999 |
| Ceramide (d18:2, C20:0) | up | 1.4975 | 0.0019335 | 3.155992 |
| Sphingomyelin (d18:2, C20:1) | up | 1.3823 | 0.002494254 | 3.075278 |
| TAG (C16:0, C18:1, C18:3) | up | 1.5231 | 0.003143958 | 3.00091 |
| Sphingomyelin (d17:1, C20:0) | up | 1.3626 | 0.003989988 | 2.923562 |
| Sphingomyelin (d18:2, C24:2) | up | 1.2165 | 0.00405684 | 2.91809 |
| Sphingomyelin (d18:1, C21:0) | up | 1.3025 | 0.004503963 | 2.883483 |
| Proline | down | 0.748 | 0.004588723 | -2.877 |
| Sphingomyelin (d18:2, C20:0) | up | 1.2522 | 0.004755925 | 2.865343 |
| N,N-Dimethylarginine (ADMA) | down | 0.8133 | 0.005429519 | -2.82058 |
| Histidine | down | 0.7173 | 0.006031531 | -2.78489 |
| Sphingomyelin (d18:2, C18:0) | up | 1.2451 | 0.006065 | 2.783001 |
| FFA_Palmitoleic acid (C16:cis[9]1) | down | 0.5808 | 0.006354103 | -2.76734 |
| Pseudouridine | down | 0.6795 | 0.006517367 | -2.75838 |
| Sphingomyelin (d18:2, C21:0) | up | 1.3436 | 0.006940038 | 2.736985 |
| Ceramide (d18:1, C20:0) | up | 1.4129 | 0.007134217 | 2.727937 |
| Ceramide (d18:1, C21:0) | up | 1.4489 | 0.007309769 | 2.719503 |
| Cholesterylester C14:1 | down | 0.639 | 0.008019146 | -2.68671 |
| 7-Methylguanosine | down | 0.7758 | 0.008427974 | -2.66903 |
| Sphingomyelin (d17:1, C18:0) | up | 1.3307 | 0.008979082 | 2.646896 |
| Ceramide (d17:1, C16:0) | up | 1.3949 | 0.008979607 | 2.647335 |
| 1-Methylhistidine | down | 0.8072 | 0.009819775 | -2.61485 |
| Tetradecanoylcarnitine | down | 0.7371 | 0.010786698 | -2.58114 |
| Pantothenic acid | down | 0.7347 | 0.011898307 | -2.5456 |
| Sphingomyelin (d18:1, C18:1) | up | 1.3253 | 0.01264873 | 2.523445 |
| DAG_Palmitic acid (C16:0) | down | 0.42 | 0.013190989 | -2.50822 |
| Ceramide (d18:2, C18:0) | up | 1.4046 | 0.013880851 | 2.489579 |
| Sphingomyelin (d18:2, C23:1) | up | 1.2538 | 0.01514839 | 2.456672 |

TABLE 29-continued

List of identified biomarkers in serum for pancreatic cancer relative to pancreatitis

| Metabolite | Direction | Estimated fold change | ANOVA result of pancreatic cancer relative to pancreatitis in serum | |
|---|---|---|---|---|
| | | | p-value | t-value |
| PS__Palmitic acid (C16:0) | down | 0.3043 | 0.016545194 | −2.42371 |
| 3-Indoxylsulfate | down | 0.5227 | 0.016706631 | −2.41986 |
| Campesterol | down | 0.6904 | 0.016791704 | −2.41794 |
| Sphingomyelin (d18:2, C22:0) | up | 1.304 | 0.017927017 | 2.393099 |
| Sphingomyelin (d18:2, C18:0) | up | 1.3422 | 0.017980277 | 2.391968 |
| Ceramide (d18:1, C18:0) | up | 1.4163 | 0.018761431 | 2.376059 |
| Palmitoleic acid (C16:cis[9]1) | down | 0.6784 | 0.01999529 | −2.35122 |
| Sphingomyelin (d18:1, C22:1) | up | 1.3106 | 0.020282899 | 2.345704 |
| Sphingomyelin (d18:1, C20:0) | up | 1.2418 | 0.021769114 | 2.318246 |
| Sphingomyelin (d18:1, C20:1) | up | 1.2497 | 0.021853538 | 2.316737 |
| Phenylalanine | down | 0.8095 | 0.022717345 | −2.30142 |
| Coenzyme Q9 | down | 0.6369 | 0.023299502 | −2.29312 |
| Uridine | down | 0.7878 | 0.025020547 | −2.26335 |
| MAG__Stearic acid (C18:0) | down | 0.6947 | 0.025859529 | −2.25083 |
| Hexadecanoylcarnitine | down | 0.7697 | 0.026017925 | −2.24781 |
| Threonine | down | 0.8146 | 0.026945311 | −2.23382 |
| Mannose | up | 1.7485 | 0.028419125 | 2.212844 |
| Ceramide (d18:2, C16:0) | up | 1.2947 | 0.030380468 | 2.185808 |
| Ceramide (d18:1, C22:1) | up | 1.4072 | 0.031629333 | 2.169372 |
| Sphingomyelin (d17:1, C22:0) | up | 1.25 | 0.032365612 | 2.159677 |
| Ceramide (d18:2, C22:0) | up | 1.279 | 0.034401307 | 2.13481 |
| MAG__Oleic acid (C18:cis[9]1) | down | 0.5128 | 0.036301979 | −2.1126 |
| Sphingomyelin (d18:1, C24:2) | up | 1.2677 | 0.036538219 | 2.10952 |
| Cystine | down | 0.6627 | 0.03773506 | −2.09605 |
| Sphingomyelin (d17:1, C24:1) | up | 1.1767 | 0.043724822 | 2.033665 |
| Sarcosine | down | 0.783 | 0.04645201 | −2.0081 |
| Sphingomyelin (d18:1, C18:0) | up | 1.278 | 0.047624028 | 1.996875 |
| Sphingomyelin (d18:1, C23:1) | up | 1.18 | 0.048636538 | 1.987742 |
| Octadecanoylcarnitine | down | 0.8093 | 0.05113107 | −1.96581 |
| TAG__Linoleic acid (C18:cis[9,12]2) | up | 1.4741 | 0.053960198 | 1.942212 |
| Sphingomyelin (d17:1, C16:0) | up | 1.2523 | 0.053967727 | 1.942151 |
| Erythrol | down | 0.7977 | 0.055226592 | −1.93185 |
| N-Acetylcytidine | down | 0.784 | 0.055518717 | −1.92951 |
| Ceramide (d17:1, C22:0) | up | 1.2712 | 0.057891482 | 1.911159 |
| epsilon-Acetyllysine | down | 0.856 | 0.059138083 | −1.90134 |
| Quinic acid | down | 0.6024 | 0.060160786 | −1.89832 |
| Androstenedione | down | 0.7708 | 0.066836588 | −1.84609 |
| Isocitrate | down | 0.8568 | 0.075542806 | −1.78947 |
| Tyrosine | down | 0.8428 | 0.07659407 | −1.78285 |
| Phosphate (inorganic and from organic phosphates) | up | 0.7772 | 0.078319502 | −1.77271 |
| Sphingomyelin (d18:2, C24:1) | up | 1.2324 | 0.080227014 | 1.761131 |
| Aspartate | down | 0.7832 | 0.08101072 | −1.75646 |
| 3-Hydroxyisobutyrate | down | 0.7953 | 0.081406107 | −1.75423 |
| LPC__Arachidonic acid (C20:cis[5,8,11,14]4) | up | 0.6423 | 0.082693197 | −1.74679 |
| 3-Hydroxyisobutyrate | down | 0.5361 | 0.085234841 | −1.7323 |
| Ceramide (d17:1, C24:1) | up | 1.2125 | 0.086649647 | 1.724654 |
| 1-Hydroxy-2-amino-(cis,trans)-3,5-octadecadiene (from sphingolipids) | up | 1.2439 | 0.086787503 | 1.72367 |
| TAG (C16:0, C18:1, C18:2) | up | 1.2912 | 0.088582763 | 1.715218 |
| Glycerol, polar fraction | down | 0.7693 | 0.089390729 | −1.70947 |
| FFA__cis-Vaccenic acid | down | 0.7432 | 0.089534331 | −1.70877 |
| Cholesterylester C18:1 | up | 0.8639 | 0.092386252 | −1.69362 |
| TAG__dihomo-gamma-Linolenic acid (C20:cis[8,11,14]3) | up | 1.5331 | 0.097298227 | 1.668384 |
| Ceramide (d18:1, C23:1) | up | 1.2439 | 0.102085315 | 1.644896 |
| Ribonic acid | down | 0.8059 | 0.102980747 | −1.64038 |
| myo-Inositol | down | 0.8066 | 0.109457639 | −1.61001 |
| Ceramide (d16:1, C18:0) | up | 1.2392 | 0.116466943 | 1.578894 |
| Creatinine | down | 0.8516 | 0.118716065 | −1.56899 |
| Ceramide (d18:1, C22:0) | up | 1.1531 | 0.119495116 | 1.565832 |
| Ceramide (d16:1, C20:0) | up | 1.2218 | 0.119885873 | 1.564166 |
| Ceramide (d18:1, C24:2) | up | 1.209 | 0.122327836 | 1.553849 |
| LPC__cis-Vaccenic acid | up | 0.6524 | 0.127022566 | −1.53435 |
| 1,5-Anhydrosorbitol | down | 0.7163 | 0.129241821 | −1.52555 |
| Ornithine | down | 0.8494 | 0.132740006 | −1.51144 |
| Ceramide (d18:1, C16:0) | up | 1.2022 | 0.133614664 | 1.508169 |
| Furoylglycine | down | 0.5465 | 0.133825096 | −1.50966 |

TABLE 29-continued

List of identified biomarkers in serum for pancreatic cancer relative to pancreatitis

| Metabolite | Direction | Estimated fold change | ANOVA result of pancreatic cancer relative to pancreatitis in serum | |
|---|---|---|---|---|
| | | | p-value | t-value |
| Sphingomyelin (d16:1, C18:1) | up | 1.204 | 0.134773332 | 1.503545 |
| PI_Linoleic acid (C18:cis[9,12]2) | up | 0.5443 | 0.135615536 | −1.50028 |
| TAG_Arachidonic acid (C20:cis[5,8,11,14]4) | up | 1.2706 | 0.146199585 | 1.460562 |
| PS_Stearic acid (C18:0) | down | 0.5452 | 0.146600494 | −1.45915 |
| MAG_Palmitic acid (C16:0) | down | 0.6587 | 0.151089957 | −1.4431 |
| FFA_Palmitic acid (C16:0) | down | 0.8293 | 0.15122502 | −1.44248 |
| trans-4-Hydroxyproline | down | 0.8387 | 0.152106042 | −1.43931 |
| Sphingomyelin (d18:2, C16:0) | up | 1.1725 | 0.15961601 | 1.413287 |
| TAG_gamma-Linolenic acid (C18:cis[6,9,12]3) | up | 1.4255 | 0.162341079 | 1.404059 |
| Citrate | down | 0.8468 | 0.167390859 | −1.38919 |
| Dehydroepiandrosterone sulfate | up | 0.7467 | 0.173750506 | −1.36666 |
| Glycerol-3-phosphate, polar fraction | up | 0.804 | 0.179405454 | −1.34876 |
| Phosphatidylcholine (C18:0, C18:1) | down | 0.9044 | 0.18215668 | −1.34023 |
| Sphingomyelin (d16:1, C22:1) | up | 1.143 | 0.199694768 | 1.288025 |

TABLE 30

List of identified biomarkers in plasma for pancreatic cancer relative to pancreatitis

| Metabolite | Direction | Estimated fold change | ANOVA result of pancreatic cancer relative to pancreatitis in plasma | |
|---|---|---|---|---|
| | | | p-value | t-value |
| Sphingomyelin (d18:2, C22:1) | up | 1.6153 | 3.12104E−06 | 4.842932 |
| Proline | down | 0.6895 | 2.2408E−05 | −4.37545 |
| Sphingomyelin (d17:1, C24:1) | up | 1.587 | 4.27653E−05 | 4.214581 |
| Sphingomyelin (d18:1, C23:1) | up | 1.6747 | 4.68851E−05 | 4.191339 |
| Sphingomyelin (d17:1, C18:0) | up | 1.3615 | 4.85522E−05 | 4.182486 |
| Sphingomyelin (d18:1, C22:1) | up | 1.767 | 5.46547E−05 | 4.152388 |
| Sphingomyelin (d18:1, C19:0) | up | 1.4382 | 7.71969E−05 | 4.063708 |
| Phosphatidylcholine (C18:0, C22:6) | up | 1.2637 | 8.59408E−05 | 4.035873 |
| Sphingomyelin (d18:1, C20:1) | up | 1.6237 | 0.000147707 | 3.893232 |
| Sphingomyelin (d18:0, C18:0) | up | 1.7822 | 0.000205464 | 3.804441 |
| Sphingomyelin (d18:2, C20:1) | up | 1.3931 | 0.000228537 | 3.775489 |
| PC_Docosahexaenoic acid (C22:cis[4,7,10,13,16,19]6) | up | 1.4333 | 0.000235934 | 3.767399 |
| Docosahexaenoic acid (C22:cis[4,7,10,13,16,19]6) | up | 1.4727 | 0.000275587 | 3.724169 |
| Sphingomyelin (d18:1, C24:1) | up | 1.3496 | 0.000301678 | 3.699187 |
| Histidine | down | 0.7707 | 0.000324059 | −3.67934 |
| Nervonic acid (C24:cis[15]1) | up | 1.3554 | 0.000382933 | 3.632725 |
| Sphingomyelin (d18:1, C21:0) | up | 1.55 | 0.000666074 | 3.474936 |
| Sphingomyelin (d18:1, C24:2) | up | 1.5844 | 0.000702203 | 3.459606 |
| Cholesterylester C14:1 | down | 0.5891 | 0.000804669 | −3.41984 |
| Sphingomyelin (d16:1, C22:1) | up | 1.4853 | 0.000809878 | 3.417949 |
| Citrulline | down | 0.757 | 0.000855559 | −3.40183 |
| Sphingomyelin (d18:1, C18:1) | up | 1.3879 | 0.00092022 | 3.380335 |
| Sphingomyelin (d18:2, C19:0) | up | 1.3682 | 0.000937129 | 3.374948 |
| 1-Hydroxy-2-amino-(cis,trans-3,5-octadecadiene (from sphingolipids) | up | 1.4196 | 0.0010776 | 3.333412 |
| Sphingomyelin (d17:1, C20:0) | up | 1.3428 | 0.001218963 | 3.296437 |
| Ceramide (d18:1, C24:0) | up | 0.7909 | 0.001508765 | −3.23293 |
| Sphingomyelin (d18:2, C24:2) | up | 1.3335 | 0.001829315 | 3.172443 |
| Sphingomyelin (d18:1, C18:0) | up | 1.2858 | 0.002019719 | 3.141654 |
| Ceramide (d18:2, C24:0) | up | 0.7029 | 0.002259236 | −3.10761 |
| Sphingomyelin (d18:2, C24:1) | up | 1.364 | 0.00231516 | 3.098834 |
| erythro-Dihydrosphingosine (d18:0) | up | 1.6091 | 0.002479426 | 3.077168 |
| Cholesterol, free | up | 1.2431 | 0.002588129 | 3.063549 |
| Sphingomyelin (d18:2, C18:1) | up | 1.3772 | 0.002614513 | 3.060323 |

TABLE 30-continued

List of identified biomarkers in plasma for
pancreatic cancer relative to pancreatitis

|  | | ANOVA result of pancreatic cancer relative to pancreatitis in plasma | | |
| --- | --- | --- | --- | --- |
| Metabolite | Direction | Estimated fold change | p-value | t-value |
| Ceramide (d18:1, C22:1) | up | 1.5754 | 0.002820175 | 3.037171 |
| Sphingomyelin (d18:2, C23:1) | up | 1.3791 | 0.003127626 | 3.002909 |
| Coenzyme Q9 | down | 0.5759 | 0.00346341 | −2.96987 |
| Creatine | down | 0.7493 | 0.004048717 | −2.91875 |
| Sphingomyelin (d17:1, C16:0) | up | 1.2017 | 0.004553063 | 2.879876 |
| FS_Cholesterol, free | up | 1.3773 | 0.004696542 | 2.869538 |
| gamma-Tocopherol | down | 0.6819 | 0.004716719 | −2.86811 |
| 3-O-Methylsphingosine (d18:1) | up | 1.3826 | 0.006240872 | 2.773492 |
| Sphingomyelin (d18:2, C21:0) | up | 1.2945 | 0.007497189 | 2.710209 |
| Isocitrate | down | 1.2572 | 0.008073829 | 2.684331 |
| 5-O-Methylsphingosine (d18:1) | up | 1.3027 | 0.008078261 | 2.684139 |
| erythro-Sphingosine (d18:1) | up | 1.2569 | 0.00826139 | 2.676274 |
| Ornithine | down | 0.8191 | 0.008496731 | −2.6664 |
| Ceramide (d17:1, C16:0) | up | 1.3308 | 0.009659761 | 2.621604 |
| Sphingomyelin (d18:2, C16:0) | up | 1.1343 | 0.010189687 | 2.601829 |
| Ceramide (d18:1, C18:0) | up | 1.4369 | 0.010845552 | 2.580037 |
| gamma-Linolenic acid (C18:cis[6,9,12]3) | up | 0.666 | 0.011356235 | −2.56275 |
| Phosphatidylcholine (C16:0, C16:0) | down | 1.1645 | 0.012758272 | 2.520282 |
| Cholesterylester C16:3 | up | 0.7378 | 0.014873216 | −2.46352 |
| Glycochenodeoxycholic acid | down | 2.2659 | 0.015139856 | 2.457258 |
| Sphingomyelin (d18:2, C18:0) | up | 1.2097 | 0.015665452 | 2.444098 |
| Heptadecanoic acid (C17:0) | up | 1.21 | 0.015686666 | 2.44359 |
| Cortisol | up | 1.2751 | 0.016284634 | 2.429518 |
| Ceramide (d17:1, C24:0) | up | 0.7629 | 0.016965835 | −2.41458 |
| Sphingomyelin (d17:1, C22:0) | up | 1.3416 | 0.019550823 | 2.359887 |
| 2-Hydroxybutyrate | up | 1.367 | 0.020060225 | 2.353764 |
| threo-Sphingosine (d18:1) | up | 1.2126 | 0.02071436 | 2.337555 |
| Sphingomyelin (d18:2, C18:0) | up | 1.1295 | 0.021207257 | 2.328427 |
| epsilon-Acetyllysine | down | 0.8595 | 0.021629287 | −2.32076 |
| Sphingomyelin (d18:2, C20:0) | up | 1.2212 | 0.022143876 | 2.311584 |
| Mannose | up | 1.3289 | 0.023498047 | 2.288459 |
| Phosphatidylcholine (C18:0, C20:4) | up | 1.0459 | 0.026971731 | 2.233566 |
| trans-4-Hydroxyproline | down | 0.7803 | 0.027481551 | −2.22606 |
| Sphingomyelin (d18:1, C20:0) | up | 1.284 | 0.027583168 | 2.224575 |
| Ribonic acid | down | 0.8229 | 0.028209262 | −2.21658 |
| Sphingomyelin (d16:1, C18:1) | up | 1.2821 | 0.028763727 | 2.207696 |
| Androstenedione | down | 0.7491 | 0.030930675 | −2.17863 |
| Ceramide (d18:1, C24:2) | up | 1.3011 | 0.03270557 | 2.155788 |
| Ceramide (d18:2, C23:0) | up | 0.7619 | 0.033183627 | −2.14982 |
| Ceramide (d18:1, C23:1) | up | 1.2985 | 0.036735645 | 2.107649 |
| Uric acid | down | 0.8122 | 0.039553284 | −2.07626 |
| Arginine | up | 0.8407 | 0.039715907 | −2.07453 |
| Sphingomyelin (d16:1, C24:1) | up | 1.2967 | 0.040063403 | 2.070854 |
| Sphingomyelin (d18:1, C16:0) | up | 1.1089 | 0.041546222 | 2.055456 |
| Cholesterylester C16:1 | down | 0.7801 | 0.042152212 | −2.0493 |
| PC_cis-Vaccenic acid | up | 1.2837 | 0.043221693 | 2.038727 |
| Ceramide (d18:1, C16:0) | up | 1.2534 | 0.047153541 | 2.001505 |
| Ceramide (d18:1, C23:0) | up | 0.8451 | 0.04882378 | −1.98639 |
| PC_Arachidonic acid (C20:cis[5,8,11,14]4) | up | 1.1952 | 0.049342791 | 1.981572 |
| 2-Hydroxypalmitic acid (C16:0) | down | 1.1778 | 0.050970096 | 1.96729 |
| Quinic acid | down | 0.5999 | 0.053497846 | −1.94873 |
| PI_dihomo-gamma-Linolenic acid (C20:cis[8,11,14]3) | up | 0.6492 | 0.054295028 | −1.93948 |
| LPC_cis-Vaccenic acid | up | 0.5475 | 0.055303605 | −1.93142 |
| Ceramide (d18:1, C20:0) | up | 1.2401 | 0.060429827 | 1.892009 |
| Sphingomyelin (d16:1, C21:0) | up | 1.2423 | 0.061539773 | 1.883522 |
| Ceramide (d18:1, C21:0) | up | 1.2235 | 0.063534014 | 1.869369 |
| Arachidonic acid (C20:cis[5,8,11,14]4) | up | 1.175 | 0.068087223 | 1.83751 |
| PC_Palmitic acid (C16:0) | up | 1.181 | 0.078121305 | 1.773743 |
| Sphingomyelin (d16:1, C18:0) | up | 1.1273 | 0.083566982 | 1.741797 |
| TAG_Arachidonic acid (C20:cis[5,8,11,14]4) | up | 1.2579 | 0.085000353 | 1.733693 |
| Methionine | down | 0.9103 | 0.086723537 | −1.7241 |
| LPC_Arachidonic acid (C20:cis[5,8,11,14]4) | up | 0.6348 | 0.093194442 | −1.68946 |

TABLE 30-continued

List of identified biomarkers in plasma for
pancreatic cancer relative to pancreatitis

| Metabolite | Direction | ANOVA result of pancreatic cancer relative to pancreatitis in plasma | | |
|---|---|---|---|---|
| | | Estimated fold change | p-value | t-value |
| PS_Stearic acid (C18:0) | down | 0.4987 | 0.095853935 | −1.76307 |
| Sphingomyelin (d18:2, C16:0) | up | 1.1954 | 0.099579228 | 1.657014 |
| Ceramide (d18:2, C16:0) | up | 1.1785 | 0.102455467 | 1.643174 |
| Isoleucine | up | 0.8955 | 0.102682128 | −1.64188 |
| Phosphate (from Phospholipids) | up | 1.1238 | 0.104160102 | 1.634801 |
| Threonine | down | 0.8815 | 0.105824932 | −1.62692 |
| Ceramide (d18:2, C18:0) | up | 1.2113 | 0.108062148 | 1.616682 |
| PE_Docosahexaenoic acid (C22:cis[4,7,10,13,16,19]6) | up | 1.1609 | 0.109022294 | 1.612065 |
| 1,5-Anhydrosorbitol | down | 0.6971 | 0.112183948 | −1.5979 |
| Cholesterylester C22:6 | up | 1.157 | 0.131073284 | 1.518073 |
| Ceramide (d18:1, C24:1) | up | 1.1274 | 0.131395252 | 1.516961 |
| Furoylglycine | down | 0.4928 | 0.132771551 | −1.51142 |
| 1-Methylhistidine | down | 0.8842 | 0.134404228 | −1.50498 |
| PC_trans-Vaccenic acid (C18:trans[11]1) | up | 1.3081 | 0.148310589 | 1.452957 |
| PE_Arachidonic acid (C20:cis[5,8,11,14]4) | up | 0.8713 | 0.154525702 | −1.43085 |
| Tetradecanoylcarnitine | down | 1.1734 | 0.159197359 | 1.414715 |
| Ceramide (d16:1, C22:0) | up | 0.8501 | 0.159388736 | −1.4142 |
| 3-Hydroxybutyrate | down | 1.5634 | 0.162013144 | 1.405164 |
| Coenzyme Q10 | down | 0.8497 | 0.165096684 | −1.39485 |
| PC_conjugated Linoleic acid (C18:cis[9]trans[11]2) | up | 1.3348 | 0.165412272 | 1.393845 |
| Erythrol | down | 0.8866 | 0.16720991 | −1.38786 |
| Ceramide (d17:1, C23:0) | up | 0.8365 | 0.172373833 | −1.3712 |
| Sphingomyelin (d18:1, C22:0) | up | 1.1189 | 0.174992719 | 1.3627 |
| Ceramide (d17:1, C24:1) | up | 1.132 | 0.181487495 | 1.342464 |
| Citrate | down | 1.1266 | 0.183236849 | 1.336949 |
| DAG (C18:1, C18:2) | up | 1.1226 | 0.191678456 | 1.311464 |
| Corticosterone | up | 1.4104 | 0.193700627 | 1.305522 |
| Glucuronic acid | down | 1.2349 | 0.193825582 | 1.305193 |
| Cholesterylester C18:1 | up | 0.9192 | 0.198420102 | −1.2917 |
| Ceramide (d16:1, C18:0) | up | 1.168 | 0.198501603 | 1.291583 |

TABLE 30a

List of further biomarkers in plasma for pancreatic
cancer relative to pancreatitis

| Metabolite | Direction | ANOVA result of pancreatic cancer relative to pancreatitis in plasma | | |
|---|---|---|---|---|
| | | Estimated fold change | p-value | t-value |
| Allantoin | down | 0.91 | 0.010937785 | −2.58 |
| Glutamate | up | 1.19 | 0.199964208 | 1.29 |

TABLE 31

List of identified biomarkers in plasma combined with
serum for pancreatic cancer relative to pancreatitis

| Metabolite | Direction | ANOVA result of pancreatic cancer relative to pancreatitis in plasma combined with serum | | |
|---|---|---|---|---|
| | | Estimated fold change | p-value | t-value |
| Sphingomyelin (d18:2, C22:1) | up | 1.4051 | 7.54095E−08 | 5.510733 |
| Sphingomyelin (d18:1, C19:0) | up | 1.3679 | 7.78447E−08 | 5.504586 |
| Citrulline | down | 0.7092 | 1.54646E−07 | −5.39096 |

TABLE 31-continued

List of identified biomarkers in plasma combined with
serum for pancreatic cancer relative to pancreatitis

| | | ANOVA result of pancreatic cancer relative to pancreatitis in plasma combined with serum | | |
|---|---|---|---|---|
| Metabolite | Direction | Estimated fold change | p-value | t-value |
| Proline | down | 0.733 | 1.6096E−06 | −4.89161 |
| Sphingomyelin (d18:2, C19:0) | up | 1.3843 | 3.21488E−06 | 4.74344 |
| Histidine | down | 0.73 | 5.27549E−06 | −4.63458 |
| Sphingomyelin (d18:1, C21:0) | up | 1.3976 | 7.98627E−06 | 4.542348 |
| Sphingomyelin (d18:2, C24:2) | up | 1.2664 | 9.46741E−06 | 4.503961 |
| Sphingomyelin (d17:1, C20:0) | up | 1.3408 | 1.63736E−05 | 4.378543 |
| Sphingomyelin (d18:2, C20:1) | up | 1.3346 | 1.91142E−05 | 4.34259 |
| Cholesterylester C14:1 | down | 0.6228 | 1.91298E−05 | −4.3424 |
| Sphingomyelin (d18:1, C22:1) | up | 1.4467 | 2.17919E−05 | 4.311944 |
| Sphingomyelin (d18:2, C18:1) | up | 1.3626 | 2.35355E−05 | 4.293871 |
| Sphingomyelin (d17:1, C18:0) | up | 1.3162 | 2.39718E−05 | 4.289549 |
| Sphingomyelin (d18:1, C20:1) | up | 1.3684 | 3.11853E−05 | 4.227262 |
| Sphingomyelin (d18:1, C23:1) | up | 1.3444 | 3.21218E−05 | 4.220211 |
| Uric acid | down | 0.7267 | 3.86817E−05 | −4.17551 |
| Sphingomyelin (d17:1, C24:1) | up | 1.3056 | 3.99813E−05 | 4.16775 |
| Sphingomyelin (d18:2, C20:0) | up | 1.2479 | 8.216E−05 | 3.991236 |
| Cholesterylester C16:1 | down | 0.7126 | 0.000108103 | −3.92231 |
| Sphingomyelin (d18:1, C24:2) | up | 1.3787 | 0.000109753 | 3.918481 |
| Sphingomyelin (d18:2, C21:0) | up | 1.3044 | 0.000168479 | 3.808754 |
| Sphingomyelin (d18:1, C18:1) | up | 1.308 | 0.000203348 | 3.759783 |
| Ceramide (d18:1, C18:0) | up | 1.4324 | 0.000256282 | 3.699551 |
| Ceramide (d18:1, C20:0) | up | 1.3539 | 0.000266424 | 3.689242 |
| Coenzyme Q9 | down | 0.6245 | 0.000287189 | −3.66982 |
| TAG (C16:0, C18:1, C18:3) | up | 1.3569 | 0.000333495 | 3.628332 |
| Ceramide (d17:1, C16:0) | up | 1.3396 | 0.000361905 | 3.607059 |
| Sphingomyelin (d18:2, C23:1) | up | 1.2724 | 0.000379362 | 3.593627 |
| Ceramide (d18:1, C21:0) | up | 1.3549 | 0.000424963 | 3.563354 |
| Ceramide (d18:1, C22:1) | up | 1.4368 | 0.000572374 | 3.481166 |
| Coenzyme Q10 | down | 0.7456 | 0.000588711 | −3.4726 |
| Sphingomyelin (d18:1, C20:0) | up | 1.2642 | 0.00085526 | 3.367243 |
| Ceramide (d18:2, C20:0) | up | 1.3193 | 0.00091215 | 3.349325 |
| Sphingomyelin (d17:1, C22:0) | up | 1.2883 | 0.000980573 | 3.327957 |
| Sphingomyelin (d18:1, C18:0) | up | 1.2683 | 0.001083125 | 3.299143 |
| Sphingomyelin (d18:2, C18:0) | up | 1.2626 | 0.001263734 | 3.254065 |
| FFA_Palmitoleic acid (C16:cis[9]1) | down | 0.6627 | 0.001417392 | −3.2202 |
| Sphingomyelin (d18:2, C18:0) | up | 1.16 | 0.001537581 | 3.195909 |
| Ceramide (d18:2, C18:0) | up | 1.3166 | 0.00179923 | 3.149319 |
| Threonine | down | 0.8345 | 0.001967265 | −3.12175 |
| 1-Hydroxy-2-amino-(cis,trans-3,5-octadecadiene (from sphingolipids) | up | 1.2773 | 0.00232077 | 3.071216 |
| Quinic acid | down | 0.5812 | 0.00248201 | −3.05666 |
| epsilon-Acetyllysine | down | 0.8578 | 0.002493692 | −3.04904 |
| N,N-Dimethylarginine (ADMA) | down | 0.8707 | 0.002703501 | −3.02395 |
| Ornithine | down | 0.8249 | 0.002843004 | −3.00824 |
| 1-Methylhistidine | down | 0.8479 | 0.002870091 | −3.00527 |
| Mannose | up | 1.5127 | 0.003417068 | 2.950549 |
| Sphingomyelin (d18:2, C24:1) | up | 1.2451 | 0.003825905 | 2.914237 |
| Phosphatidylcholine (C18:0, C22:6) | up | 1.1432 | 0.00420093 | 2.88411 |
| Sphingomyelin (d16:1, C22:1) | up | 1.237 | 0.004558849 | 2.857561 |
| O-Acetylcarnitine | down | 0.7814 | 0.005213329 | −2.81351 |
| Ceramide (d18:2, C16:0) | up | 1.2359 | 0.005307354 | 2.808007 |
| trans-4-Hydroxyproline | down | 0.8022 | 0.005763094 | −2.78029 |
| Sarcosine | down | 0.8308 | 0.006247795 | −2.75367 |
| TAG_Linoleic acid (C18:cis[9,12]2) | up | 1.3779 | 0.006461217 | 2.742073 |
| Ceramide (d18:1, C24:2) | up | 1.2516 | 0.00679935 | 2.725164 |
| Palmitoleic acid (C16:cis[9]1) | down | 0.7481 | 0.00731918 | −2.69985 |
| Sphingomyelin (d18:2, C22:0) | up | 1.2164 | 0.007829807 | 2.676796 |
| Androstenedione | down | 0.7803 | 0.008343756 | −2.65515 |
| Pseudouridine | down | 0.8123 | 0.008413055 | −2.65201 |
| LPC_cis-Vaccenic acid | up | 0.5936 | 0.008467674 | −2.64988 |
| Cholesterol, free | up | 1.1667 | 0.00852677 | 2.647368 |
| Ribonic acid | down | 0.8135 | 0.00876408 | −2.63825 |
| Phenylalanine | down | 0.8676 | 0.00965423 | −2.60413 |
| 1,5-Anhydrosorbitol | down | 0.6798 | 0.010300725 | −2.58171 |
| 3-Indoxylsulfate | down | 0.6483 | 0.011122739 | −2.5542 |
| TAG_Arachidonic acid (C20:cis[5,8,11,14]4) | up | 1.2921 | 0.011985354 | 2.527525 |
| Sphingomyelin (d17:1, C16:0) | up | 1.1445 | 0.012593038 | 2.513154 |
| Ceramide (d18:1, C16:0) | up | 1.2193 | 0.013870643 | 2.47495 |

TABLE 31-continued

List of identified biomarkers in plasma combined with
serum for pancreatic cancer relative to pancreatitis

|  | | ANOVA result of pancreatic cancer relative to pancreatitis in plasma combined with serum | | |
|---|---|---|---|---|
| Metabolite | Direction | Estimated fold change | p-value | t-value |
| PC__Docosahexaenoic acid (C22:cis[4,7,10,13,16,19]6) | up | 1.2025 | 0.01435588 | 2.462252 |
| Ceramide (d18:1, C23:1) | up | 1.2355 | 0.016177455 | 2.418375 |
| Sphingomyelin (d18:2, C16:0) | up | 1.1045 | 0.016312122 | 2.415036 |
| LPC__Arachidonic acid (C20:cis[5,8,11,14]4) | up | 0.6567 | 0.016469289 | −2.41156 |
| Tyrosine | down | 0.8753 | 0.017548104 | −2.3878 |
| MAG__Stearic acid (C18:0) | down | 0.8222 | 0.017821754 | −2.38217 |
| DAG (C18:1, C18:2) | up | 1.165 | 0.018480708 | 2.368391 |
| Ceramide (d18:1, C24:0) | up | 0.8905 | 0.020190923 | −2.33506 |
| Sphingomyelin (d18:0, C18:0) | up | 1.2639 | 0.022606384 | 2.291511 |
| Cortisol | up | 1.1875 | 0.024029553 | 2.267869 |
| Cholesterylester C16:3 | up | 0.8322 | 0.025712947 | −2.24135 |
| FS__Cholesterol, free | up | 1.1769 | 0.026355845 | 2.231743 |
| Cholesterylester C18:1 | up | 0.8902 | 0.02669165 | −2.22664 |
| Sphingomyelin (d16:1, C18:1) | up | 1.1946 | 0.02691608 | 2.223337 |
| erythro-Sphingosine (d18:1) | up | 1.1554 | 0.027447936 | 2.215561 |
| MAG__Oleic acid (C18:cis[9]1) | down | 0.6993 | 0.027614056 | −2.21331 |
| DAG__Palmitic acid (C16:0) | down | 0.5831 | 0.027750028 | −2.21129 |
| Uridine | down | 0.8641 | 0.029177631 | −2.19181 |
| Furoylglycine | down | 0.5188 | 0.029504259 | −2.18818 |
| 3-O-Methylsphingosine (d18:1) | up | 1.1987 | 0.030012003 | 2.179966 |
| Ceramide (d17:1, C22:0) | up | 1.1831 | 0.031048649 | 2.166514 |
| Ceramide (d17:1, C24:1) | up | 1.1639 | 0.032866637 | 2.143495 |
| gamma-Tocopherol | down | 0.8141 | 0.033443133 | −2.1363 |
| TAG__dihomo-gamma-Linolenic acid (C20:cis[8,11,14]3) | up | 1.3628 | 0.033669386 | 2.133521 |
| PS__Palmitic acid (C16:0) | down | 0.3966 | 0.033859432 | −2.13874 |
| Erythrol | down | 0.8606 | 0.034747545 | −2.12062 |
| Docosahexaenoic acid (C22:cis[4,7,10,13,16,19]6) | up | 1.189 | 0.035833069 | 2.108004 |
| Cystine | down | 0.7942 | 0.03612422 | −2.10471 |
| Ceramide (d16:1, C18:0) | up | 1.1999 | 0.037901529 | 2.085021 |
| Sphingomyelin (d18:2, C16:0) | up | 1.1671 | 0.038667107 | 2.076574 |
| 5-O-Methylsphingosine (d18:1) | up | 1.1617 | 0.039884223 | 2.063637 |
| Dehydroepiandrosterone sulfate | up | 0.7436 | 0.042036936 | −2.04213 |
| Sphingomyelin (d18:1, C24:1) | up | 1.1165 | 0.0430598 | 2.0315 |
| Campesterol | down | 0.8026 | 0.044955946 | −2.01335 |
| FFA__cis-Vaccenic acid | down | 0.7776 | 0.046127998 | −2.00228 |
| Aspartate | down | 0.8513 | 0.046850764 | −1.99561 |
| Heptadecanoic acid (C17:0) | up | 1.129 | 0.048667413 | 1.979294 |
| TAG (C16:0, C18:1, C18:2) | up | 1.1894 | 0.04880215 | 1.978557 |
| MAG__Palmitic acid (C16:0) | down | 0.647 | 0.050530745 | −1.96318 |
| myo-Inositol | down | 0.8636 | 0.05510547 | −1.92531 |
| Glycerol, polar fraction | down | 0.8274 | 0.055474539 | −1.92238 |
| Nervonic acid (C24:cis[15]1) | up | 1.1217 | 0.059026207 | 1.894973 |
| Sphingomyelin (d18:1, C22:0) | up | 1.1236 | 0.061872822 | 1.874008 |
| Ceramide (d16:1, C20:0) | up | 1.1676 | 0.066086059 | 1.84448 |
| Octadecanoylcarnitine | down | 0.8846 | 0.068465313 | −1.8283 |
| threo-Sphingosine (d18:1) | up | 1.1184 | 0.072102549 | 1.804633 |
| Hexadecanoylcarnitine | down | 0.8822 | 0.073707452 | −1.7945 |
| Phosphate (inorganic and from organic phosphates) | up | 0.8717 | 0.073926374 | −1.79321 |
| 7-Methylguanosine | down | 0.8895 | 0.076842023 | −1.77522 |
| Glycerol-3-phosphate, polar fraction | up | 0.8272 | 0.087133931 | −1.71774 |
| PC__Arachidonic acid (C20:cis[5,8,11,14]4) | up | 1.1162 | 0.099668389 | 1.651454 |
| Creatine | down | 0.8779 | 0.107084585 | −1.61612 |
| Tetradecanoylcarnitine | down | 0.8816 | 0.110346804 | −1.60122 |
| Ceramide (d18:2, C24:0) | up | 0.885 | 0.110465605 | −1.60077 |
| Sphingomyelin (d18:1, C16:0) | up | 1.0465 | 0.110682387 | 1.599725 |
| Sphingomyelin (d16:1, C21:0) | up | 1.1488 | 0.114900639 | 1.581002 |
| PS__Stearic acid (C18:0) | down | 0.5738 | 0.116878026 | −1.57589 |
| Corticosterone | up | 1.3002 | 0.124798298 | 1.539148 |
| FFA__Palmitic acid (C16:0) | down | 0.8775 | 0.126394868 | −1.53261 |
| Ceramide (d18:1, C24:1) | up | 1.0937 | 0.126592813 | 1.531877 |
| Pantothenic acid | down | 0.8834 | 0.135644564 | −1.4961 |
| Ceramide (d18:1, C22:0) | up | 1.0883 | 0.140321488 | 1.478455 |
| Lignoceric acid (C24:0) | up | 0.9147 | 0.151000349 | −1.43959 |
| Ceramide (d18:2, C22:0) | up | 1.1126 | 0.156759059 | 1.419565 |

TABLE 31-continued

List of identified biomarkers in plasma combined with serum for pancreatic cancer relative to pancreatitis ANOVA result of pancreatic cancer relative to pancreatitis in plasma combined with serum

| Metabolite | Direction | Estimated fold change | p-value | t-value |
|---|---|---|---|---|
| FFA__Myristoleic acid (C14:cis[9]1) | down | 0.7209 | 0.160847349 | −1.4056 |
| PI__Linoleic acid (C18:cis[9,12]2) | up | 0.729 | 0.161090757 | −1.40478 |
| FFA__Linolenic acid (C18:cis[9,12,15]3) | up | 0.8051 | 0.177342977 | −1.35207 |
| Glycochenodeoxycholic acid | down | 1.3563 | 0.179541868 | 1.345277 |
| Arachidonic acid (C20:cis[5,8,11,14]4) | up | 1.0983 | 0.18049037 | 1.342271 |
| Sphingomyelin (d16:1, C20:0) | up | 1.1131 | 0.18475197 | 1.329232 |
| Methionine | down | 0.935 | 0.190912747 | −1.31075 |
| Eicosanoic acid (C20:0) | up | 1.0705 | 0.192183894 | 1.306993 |
| Ceramide (d7:1, C24:0) | up | 0.8982 | 0.197610342 | −1.29121 |

TABLE 32

List of identified biomarkers in serum for pancreatic cancer relative to control (blood donors)

ANOVA result of pancreatic cancer relative to control (blood donors) in serum

| Metabolite | Direction | Estimated fold change | p-value | t-value |
|---|---|---|---|---|
| Lysophosphatidyl-ethanolamine (C18:2) | down | 0.577 | 0.00156622 | −3.25511 |
| Sphingomyelin (d17:1, C16:0) | up | 1.3587 | 0.01407457 | 2.50108847 |
| Lysophosphatidyl-choline (C18:0) | up | 1.268 | 0.02237293 | 2.30771756 |
| Sphingomyelin (d17:1, C16:0) | up | 2.0372 | 0.19534056 | 1.30403267 |

TABLE 33

List of identified biomarkers in plasma combined with serum for pancreatic cancer relative to control (blood donors)

ANOVA results of pancreatic cancer relative to control (blood donors) in plasma combined with serum

| Metabolite | Direction | Estimated fold change | p-value | t-value |
|---|---|---|---|---|
| Lysophosphatidyl-ethanolamine (C18:2) | down | 0.5082 | 1.2246E−05 | −4.50 |
| Sphingomyelin (d17:1, C16:0) | up | 1.5107 | 0.00012772 | 3.91937588 |
| Lysophosphatidyl-choline (C18:0) | up | 1.2576 | 0.02410202 | 2.27065088 |
| Sphingomyelin (d18:2, C24:0) | up | 1.1914 | 0.06618025 | 1.84605689 |
| Sphingomyelin (d17:1, C16:0) | up | 1.8984 | 0.07358616 | 1.80010609 |
| Sphingomyelin (d18:2, C17:0) | up | 2.2114 | 0.10399739 | 1.63438039 |
| Sphingomyelin (d17:1, C18:0) | up | 2.0599 | 0.18632206 | 1.32680428 |

TABLE 33a

List of identified biomarkers in plasma for pancreatic cancer relative to non-pancreatic control ANOVA result of pancreatic cancer relative to non-pancreatic control in plasma

| Metabolite | Direction | Estimated fold change | p-value | t-value |
|---|---|---|---|---|
| Glutamate | up | 1.52 | 1.11502E−05 | 4.54 |
| Allantoin | down | 0.93 | 0.010084541 | −2.61 |
| Butyrylcarnitine | down | 0.83 | 0.027773999 | −2.22 |
| Sedoheptulose-7-phosphate | up | 1.17 | 0.05257924 | 1.97 |
| Hexanoylcarnitine | down | 0.85 | 0.124472537 | −1.54 |

TABLE 34

List of identified biomarkers in serum for pancreatic cancer relative to critical controls (pancreatitis and liver cirrhosis)

ANOVA results of pancreatic cancer relative to critical controls (pancreatitis and liver cirrhosis) in serum

| Metabolite | Direction | Estimated fold change | p-value | t-value |
|---|---|---|---|---|
| Sphingomyelin (d17:1, C16:0) | up | 1.186 | 0.02362018 | 2.28738611 |
| Sphingomyelin (d18:2, C24:0) | up | 1.0907 | 0.07053766 | 1.81676671 |
| Sphingomyelin (d18:2, C17:0) | up | 1.1699 | 0.08867187 | 1.71396562 |
| TAG (C18:1, C18:2, C18:3) | up | 1.1762 | 0.1013912 | 1.6456486 |
| Sphingomyelin (d17:1, C16:0) | up | 1.3842 | 0.168661 | 1.38342438 |

TABLE 35

List of identified biomarkers in plasma combined with serum for pancreatic cancer relative to critical controls (pancreatitis and liver cirrhosis)

| Metabolite | Direction | ANOVA results of pancreatic cancer relative to critical controls (pancreatitis and liver cirrhosis) in plasma combined with serum | | |
|---|---|---|---|---|
| | | Estimated fold change | p-value | t-value |
| Lysophosphatidyl-ethanolamine (C18:2) | down | 0.7658 | 5.0955E−05 | −4.11054 |
| Sphingomyelin (d17:1, C16:0) | up | 1.1646 | 0.00110089 | 3.29524321 |
| Sphingomyelin (d18:2, C17:0) | up | 1.1677 | 0.00232646 | 3.07122831 |
| Sphingomyelin (d18:2, C24:0) | up | 1.1038 | 0.0089445 | 2.62739206 |
| Sphingomyelin (d17:1, C16:0) | up | 1.3229 | 0.02096003 | 2.32090324 |
| TAG (C18:1, C18:2, C18:3) | up | 1.1551 | 0.0430041 | 2.03089577 |
| Sphingomyelin (d17:1, C18:0) | up | 1.2607 | 0.16566411 | 1.3896436 |

TABLE 36

List of identified biomarkers in serum for pancreatic cancer relative to liver cirrhosis

| Metabolite | Direction | ANOVA results of pancreatic cancer relative to liver cirrhosis in serum | | |
|---|---|---|---|---|
| | | Estimated fold change | p-value | t-value |
| Sphingomyelin (d18:2, C17:0) | up | 1.2627 | 0.01580708 | 2.45790679 |
| Sphingomyelin (d17:1, C16:0) | up | 1.1815 | 0.02797472 | 2.2322297 |
| Lysophosphatidyl-choline (C18:0) | up | 1.136 | 0.06093446 | 1.88779624 |
| TAG (C18:1, C18:2, C18:3) | up | 1.2232 | 0.06630851 | 1.85178193 |
| Sphingomyelin (d17:1, C16:0) | up | 1.5759 | 0.15737731 | 1.42531836 |

TABLE 37

List of identified biomarkers in plasma combined with serum for pancreatic cancer relative to liver cirrhosis

| Metabolite | Direction | ANOVA results of pancreatic cancer relative to liver cirrhosis in plasma combined with serum | | |
|---|---|---|---|---|
| | | Estimated fold change | p-value | t-value |
| Sphingomyelin (d18:2, C17:0) | up | 1.3174 | 0.00025755 | 3.73327693 |
| Sphingomyelin (d17:1, C16:0) | up | 1.2193 | 0.00352438 | 2.95922082 |
| Lysophosphatidyl-choline (C18:0) | up | 1.1418 | 0.04297793 | 2.0350991 |
| Sphingomyelin (d17:1, C16:0) | up | 1.5795 | 0.04479279 | 2.02153544 |
| TAG (C18:1, C18:2, C18:3) | up | 1.2124 | 0.045452 | 2.01248629 |
| Sphingomyelin (d17:1, C18:0) | up | 1.5184 | 0.07057557 | 1.81962329 |
| Sphingomyelin (d18:2, C24:0) | up | 1.0908 | 0.10179664 | 1.64271456 |

Example 4: Patients and Sample Preparation

From a retrospective case control study, plasma samples of 79 patients suffering from resectable (i.e. stage T1 or T2) PDAC, plasma samples of 80 patients suffering from chronic pancreatitis, and plasma samples of 80 non-pancreatic controls (hernia repair and thyroid resection) were included. Exclusion criteria were a concomitant malignant disease, curative treatment of malignant disease less than 2 years of recruitment to the trial, concomitant cystic diseases of the pancreas, pregnancy or patients unable to give informed consent. After blood drawing and centrifugation, plasma samples were collected in Eppendorf tubes and stored at −80° C. for further analysis as described in example 2. Statistical analysis was done by ANOVA as described in example 3.

Results are shown in Tables 38 and 39.

TABLE 38

List of identified biomarkers in plasma for resectable pancreatic cancer relative to pancreatitis

| Metabolite | Direction | ANOVA result of resectable pancreatic cancer relative to pancreatitis in plasma | | |
|---|---|---|---|---|
| | | Estimated fold change | p-value | t-value |
| Coenzyme Q9 | down | 0.48 | 0.000262364 | −3.77 |
| Sphingomyelin (d17:1, C18:0) | up | 1.39 | 0.000619396 | 3.52 |
| gamma-Tocopherol | down | 0.64 | 0.000811368 | −3.44 |
| Ceramide (d18:1, C18:0) | up | 1.58 | 0.001649611 | 3.22 |
| Sphingomyelin (d18:2, C18:0) | up | 1.23 | 0.001968032 | 3.17 |
| Sphingomyelin (d18:0, C18:0) | up | 1.62 | 0.002649038 | 3.07 |
| Sphingomyelin (d18:2, C20:1) | up | 1.28 | 0.003106771 | 3.02 |
| Sphingomyelin (d18:2, C18:1) | up | 1.28 | 0.003233019 | 3.01 |
| Citrulline | down | 0.79 | 0.004234786 | −2.92 |
| Ceramide (d18:2, C18:0) | up | 1.42 | 0.004602512 | 2.89 |

TABLE 38-continued

List of identified biomarkers in plasma for resectable
pancreatic cancer relative to pancreatitis

| | | ANOVA result of resectable pancreatic cancer relative to pancreatitis in plasma | | |
|---|---|---|---|---|
| Metabolite | Direction | Estimated fold change | p-value | t-value |
| Sphingomyelin (d18:2, C22:1) | up | 1.26 | 0.005588704 | 2.82 |
| Sphingomyelin (d18:1, C20:1) | up | 1.28 | 0.006349118 | 2.78 |
| Threonine | down | 0.79 | 0.006433821 | −2.78 |
| Proline | down | 0.78 | 0.006467529 | −2.77 |
| Sphingomyelin (d18:1, C18:0) | up | 1.24 | 0.007565255 | 2.72 |
| Sphingomyelin (d17:1, C18:0) | up | 1.21 | 0.008129047 | 2.69 |
| Ceramide (d16:1, C18:0) | up | 1.40 | 0.010129721 | 2.62 |
| Sphingomyelin (d18:1, C18:1) | up | 1.21 | 0.010386287 | 2.61 |
| Creatine | down | 0.76 | 0.011095461 | −2.58 |
| Sphingomyelin (d18:2, C19:0) | up | 1.33 | 0.013250651 | 2.52 |
| Sphingomyelin (d18:1, C22:1) | up | 1.26 | 0.015581643 | 2.46 |
| N,N-Dimethylarginine (ADMA) | down | 0.81 | 0.016604005 | −2.43 |
| Lysophosphatidylcholine (C18:0) | down | 0.82 | 0.018123417 | −2.40 |
| Sphingomyelin (d18:1, C23:1) | up | 1.24 | 0.018256964 | 2.39 |
| Sphingomyelin (d18:1, C24:2) | up | 1.24 | 0.018768704 | 2.38 |
| Sphingomyelin (d17:1, C24:1) | up | 1.21 | 0.018972758 | 2.38 |
| Ceramide (d17:1, C16:0) | up | 1.33 | 0.019194063 | 2.38 |
| Histidine | down | 0.83 | 0.019390345 | −2.37 |
| Octadecanoylcarnitine | down | 0.79 | 0.020960917 | −2.34 |
| Coenzyme Q10 | down | 0.71 | 0.020994194 | −2.34 |
| Sphingomyelin (d18:2, C17:0) | up | 1.17 | 0.022448489 | 2.31 |
| Allantoin | down | 0.90 | 0.024000876 | −2.29 |
| Sphingomyelin (d17:1, C20:0) | up | 1.27 | 0.024115295 | 2.29 |
| Ceramide (d18:2, C20:0) | up | 1.31 | 0.024965844 | 2.27 |
| Lysophosphatidylethanolamine (C18:2) | down | 0.79 | 0.02591185 | −2.26 |
| Sphingomyelin (d18:2, C24:2) | up | 1.19 | 0.028176764 | 2.22 |
| trans-4-Hydroxyproline | down | 0.79 | 0.031352163 | −2.18 |
| Sphingomyelin (d18:2, C23:1) | up | 1.19 | 0.036399458 | 2.12 |
| Ceramide (d18:1, C20:0) | up | 1.27 | 0.037976539 | 2.10 |
| Ornithine | down | 0.85 | 0.042421242 | −2.05 |
| Dodecanoylcarnitine | down | 0.74 | 0.042954903 | −2.05 |
| Sphingomyelin (d18:2, C18:0) | up | 1.08 | 0.045868882 | 2.02 |
| Oleoylcarnitine | down | 0.83 | 0.048667316 | −1.99 |
| Hexadecanoylcarnitine | down | 0.86 | 0.063680802 | −1.87 |
| Sphingomyelin (d18:1, C20:0) | up | 1.13 | 0.064916271 | 1.86 |
| Glutamate | up | 1.31 | 0.068014282 | 1.84 |
| Sphingomyelin (d18:1, C21:0) | up | 1.19 | 0.075358056 | 1.79 |
| Sphingomyelin (d18:1, C24:1) | up | 1.10 | 0.077758649 | 1.78 |
| Ceramide (d16:1, C20:0) | up | 1.26 | 0.0833007 | 1.75 |
| Cholesterol, free | up | 1.14 | 0.087042975 | 1.73 |
| TAG (C18:1, C18:2, C18:3) | up | 1.13 | 0.097051705 | 1.67 |
| Dodecanoylcarnitine | down | 0.77 | 0.099946654 | −1.66 |
| Sphingomyelin (d16:1, C18:1) | up | 1.15 | 0.100118304 | 1.66 |
| Sphingomyelin (d17:1, C16:0) | up | 1.14 | 0.105283297 | 1.63 |
| Sphingomyelin (d16:1, C22:1) | up | 1.17 | 0.115030296 | 1.59 |
| Octanoylcarnitine | down | 0.77 | 0.118134842 | −1.57 |
| Ceramide (d18:1, C22:1) | up | 1.31 | 0.127530329 | 1.54 |
| Sphingomyelin (d17:1, C16:0) | up | 1.07 | 0.127925459 | 1.53 |
| Sphingomyelin (d16:1, C18:0) | up | 1.18 | 0.141744114 | 1.48 |
| Sphingomyelin (d18:2, C20:0) | up | 1.10 | 0.152012301 | 1.44 |
| Aspartate | down | 0.91 | 0.153850266 | −1.44 |
| Erythrol | down | 0.89 | 0.154985801 | −1.43 |
| 3-Indoxylsulfate | down | 0.71 | 0.155611929 | −1.43 |
| Sphingomyelin (d18:1, C19:0) | up | 1.24 | 0.157096387 | 1.42 |
| Ceramide (d18:1, C21:0) | up | 1.19 | 0.157392177 | 1.42 |
| Ceramide (d18:1, C23:1) | up | 1.23 | 0.165132835 | 1.40 |
| Ceramide (d18:1, C16:0) | up | 1.17 | 0.168749843 | 1.39 |
| Methionine | down | 0.91 | 0.175505142 | −1.36 |
| Ceramide (d18:1, C24:2) | up | 1.26 | 0.178243698 | 1.35 |
| Uric acid | down | 0.88 | 0.181936467 | −1.34 |
| Sphingomyelin (d18:2, C21:0) | up | 1.13 | 0.187953909 | 1.32 |
| Quinic acid | down | 0.70 | 0.195229999 | −1.30 |
| Ceramide (d17:1, C24:1) | up | 1.17 | 0.198340202 | 1.29 |

TABLE 39

List of identified biomarkers in plasma for resectable
pancreatic cancer relative to non-pancreatic control

| Metabolite | Direction | Estimated fold change | ANOVA result of resectable pancreatic cancer relative to non-pancreatic control in plasma | |
|---|---|---|---|---|
| | | | p-value | t-value |
| Glutamate | up | 1.60 | 1.12894E−05 | 4.60 |
| Lysophosphatidyl-ethanolamine (C18:2) | down | 0.75 | 0.000282104 | −3.75 |
| Sphingomyelin (d18:1, C24:1) | up | 1.13 | 0.00264958 | 3.07 |
| Sphingomyelin (d17:1, C18:0) | up | 1.15 | 0.010065976 | 2.62 |
| Butyrylcarnitine | down | 0.78 | 0.014064671 | −2.49 |
| Allantoin | down | 0.92 | 0.024458386 | −2.28 |
| Dodecanoylcarnitine | down | 0.85 | 0.140987832 | −1.48 |
| Sedoheptulose-7-phosphate | up | 1.14 | 0.165293308 | 1.41 |

The invention claimed is:

1. A method for treating a subject in need of a pancreas cancer therapy, comprising:
   (a) obtaining a sample of a subject suspected to suffer from pancreas cancer, wherein said sample is a blood, plasma, or serum sample, and then subjecting the sample to total lipids extraction;
   (b) determining, using mass spectrometry, from the sample of step (a) the amounts of a group of biomarkers said group comprising (i) at least the biomarkers of one of the combinations shown in Table 1a, wherein the sphingomyelin(s), ceramide(s), and/or phosphorylated sphingobase(s) of Table 1a is/are selected from Table 1b or comprising (ii) at least the biomarkers shown in any one of Tables 17 to 26;
   (c) comparing the said amounts of the biomarkers with references, whereby pancreas cancer is diagnosed;
   (d) identifying a subject in need of a pancreas cancer therapy if said subject is diagnosed to suffer from pancreas cancer; and
   (e) treating the subject with a cancer therapy selected from the group consisting of surgery, radiotherapy, or drug treatment.

2. The method of claim 1, wherein said references are derived from a sample of a subject or a group of subjects known to suffer from pancreatic cancer.

3. The method of claim 1, wherein said references are derived from a sample of a subject or a group of subjects known not to suffer from pancreatic cancer.

4. The method of claim 1, wherein said group of biomarkers comprises at least one further biomarker selected from Table 16.

5. The method of claim 1, wherein said group of biomarkers is the group shown in any one of Tables 2 to 15.

6. The method of claim 1, wherein the said group of biomarkers further comprises CA19-9.

7. The method of claim 1, wherein said diagnosing comprises differentiating between pancreatic cancer and pancreatitis.

8. The method of claim 1, wherein said pancreas cancer is pancreas adenocarcinoma.

9. The method of claim 1, wherein steps (b) and (c) are performed using a device comprising:
   (a) an analyzing unit for the said sample of the subject comprising a detector for the amounts of a group of biomarkers said group comprising (i) at least the biomarkers of one of the combinations shown in Table 1a, wherein the sphingomyelin(s), ceramide(s), and/or phosphorylated sphingobase(s) of Table 1a is/are selected from Table 1b or comprising (ii) at least the biomarkers shown in any one of Tables 17 to 26, said detector comprising a mass spectrometry device and allowing for the determination of the amounts of the biomarkers of the said group of biomarkers in the sample; and operatively linked thereto,
   (b) an evaluation unit comprising a data processing unit and a data base, said data base comprising a stored reference and said data processing unit having tangibly embedded an algorithm for carrying out a comparison of the amounts of the biomarkers of the group of biomarkers determined by the analyzing unit and the stored reference and for generating an output information based on which the diagnosis can be established.

* * * * *